US010036044B2

(12) United States Patent
Graf et al.

(10) Patent No.: US 10,036,044 B2
(45) Date of Patent: Jul. 31, 2018

(54) GENETIC ENGINEERING OF *PSEUDOMONAS PUTIDA* KT2440 FOR RAPID AND HIGH YIELD PRODUCTION OF VANILLIN FROM FERULIC ACID

(71) Applicant: BASF SE, Ludwigshafen (DE)

(72) Inventors: Nadja Graf, Freiberg (DE); Josef Altenbuchner, Nufringen (DE)

(73) Assignee: BASF SE, Ludwigshafen (DE)

( * ) Notice: Subject to any disclaimer, the term of this patent is extended or adjusted under 35 U.S.C. 154(b) by 130 days.

(21) Appl. No.: 14/906,429

(22) PCT Filed: Jul. 22, 2014

(86) PCT No.: PCT/EP2014/065659
§ 371 (c)(1),
(2) Date: Jan. 20, 2016

(87) PCT Pub. No.: WO2015/011112
PCT Pub. Date: Jan. 29, 2015

(65) Prior Publication Data
US 2016/0168599 A1 Jun. 16, 2016

(30) Foreign Application Priority Data

Jul. 22, 2013 (EP) ..................................... 13177401

(51) Int. Cl.
C12P 7/24 (2006.01)
C07K 14/21 (2006.01)
C12N 9/02 (2006.01)
C12N 9/88 (2006.01)
C12N 9/00 (2006.01)
C12N 15/78 (2006.01)

(52) U.S. Cl.
CPC ................ *C12P 7/24* (2013.01); *C07K 14/21* (2013.01); *C12N 9/0008* (2013.01); *C12N 9/88* (2013.01); *C12N 9/93* (2013.01); *C12N 15/78* (2013.01)

(58) Field of Classification Search
None
See application file for complete search history.

(56) References Cited

FOREIGN PATENT DOCUMENTS

| CA | 2 348 962 A1 | 5/2000 |
| JP | H05-227980 A | 9/1993 |
| WO | WO-00/26355 A2 | 5/2000 |

OTHER PUBLICATIONS

International Search Report for PCT/EP2014/065659 dated Oct. 6, 2014.

Achterholt, S., et al., "Identification of *Amycolatopsis* sp. Strain HR167 Genes, Involved in the Bioconversion of Ferulic Acid to Vanillin", Appl. Microbiol. Biotechnol., 2000, vol. 54, pp. 799-807.
Altenbuchner, J., et al., "Positive Selection Vectors Based on Palindromic DNA Sequences", Methods in Enzymology, 1992, vol. 216, pp. 457-466.
Arkin, A. P., et al., "An Algorithm for Protein Engineering: Simulations of Recursive Ensemble Mutagenesis", Proc. Natl. Acad. Sci. USA, 1992, vol. 89, pp. 7811-7815.
Barghini, P., et al., "Vanillin Production Using Metabolically Engineered *Escherichia coli* under Non-Growing Conditions", Microbial Cell Factories, 2007, vol. 6:13, 11 pages.
Berger, R. G., "Biotechnology of Flavours—the Next Generation", Biotechnol. Lett., 2009, vol. 31, pp. 1651-1659.
Bertani, G., "Studies on Lysogenesis. I. The Mode of Phage Liberation by Lysogenic *Escherichia coli*", J. Bacteriol., 1951, vol. 62, pp. 293-300.
Blaschke, M., et al., "Molybdenum-Dependent Degradation of Quinoline by *Pseudomonas putida* Chin IK and Other Aerobic Bacteria", Archives of Microbiology, 1991, vol. 155, pp. 164-169.
Bonnin, E., et al., "Enhanced Bioconversion of Vanillic Acid into Vanillin by the Use of 'Natural' Cellobiose", Journal of the Science of Food and Agriculture, 1999, vol. 79, pp. 484-486.
Calisti, C., et al., "Regulation of Ferulic Catabolic Genes in *Pseudomonas fluorescens* BF13: Involvement of a MarR Family Regulator", Appl. Microbiol. Biotechnol., 2008, vol. 80, pp. 475-483.
Chenna, R., et al., "Multiple Sequence Alignment with the Clustal Series of Programs", Nucleic Acids Research, 2003, vol. 31, No. 13, pp. 3497-3500.
Chung, C. T., et al., "One-Step Preparation of Competent *Escherichia coli*: Transformation and Storage of Bacterial Cells in the Same Solution", Proc. Natl. Acad. Sci. USA, 1989, vol. 86, pp. 2172-2175.
Civolani, C., et al., "Bioconversion of Ferulic Acid into Vanillic Acid by Means of a Vanillate-Negative Mutant of *Pseudomonas fluorescens* strain BF13", Applied and Environmental Microbiology, 2000, vol. 66, pp. 2311-2317.
Clarke, P. H.,, "The Metabolic Versatility of Pseudomonads", Antonie van Leeuwenhoek, 1982, vol. 48, pp. 105-130.
Davidonis, G., et al., "Callus Formation and Shoot Regeneration in *Vanilla planifolia*", Food Biotechnology, 1991, vol. 5, No. 1, pp. 59-66.
Delagrave, S., et al., "Recursive Ensemble Mutagenesis", Protein Engineering, 1993, vol. 6, No. 3, pp. 327-331.
Escott-Watson, P. L., et al., "Determination of Alkali-Soluble Phenolic Monomers in Grasses after Separation by Thin-Layer Chromatograph", Journal of Chromatography, 1992, vol. 604, pp. 290-293.
Fleige, C., et al., "Investigation of the *Amycolatopsis* sp. Strain ATCC 39116 Vanillin Dehydrogenase and Its Impact on the Biotechnical Production of Vanillin", Applied and Environmental Microbiology, 2013, vol. 79, No. 1, pp. 81-90.
Frunzke, K., et al., "Molybdopterin Guanine Dinucleotide Is the Organic Moiety of the Molybdenum Cofactor in Respiratory Nitrate Reductase from *Pseudomonas stutzeri*", FEMS Microbiology Letters, 1993, vol. 113, pp. 241-245.

(Continued)

*Primary Examiner* — Anand U Desai
(74) *Attorney, Agent, or Firm* — Drinker Biddle & Reath LLP

(57) ABSTRACT

The present invention relates to an improved biocatalytic process for producing vanillin from ferulic acid based on a genetically engineered *Pseudomonas* strains, as well as to said *Pseudomonas* strains.

17 Claims, 8 Drawing Sheets

(56) References Cited

OTHER PUBLICATIONS

Gasson, M. J., et al., "Metabolism of Ferulic Acid to Vanillin. A Bacterial Gene of the Enoyl-SCoA Hydratase/Isomerase Superfamily Encodes an Enzyme for the Hydration and Cleavage of a Hydroxycinnamic Acid SCoA Thioester", J. Biol. Chem., 1998, vol. 273, No. 7, pp. 4163-4170.

Graf, N., et al., "Development of a Method for Markerless Gene Deletion in *Pseudomonas putida*", Applied and Environmental Microbiology, 2011, vol. 77, No. 15, pp. 5549-5552.

Greasham, R. L., et al., "Design and Optimization of Growth Media", Chapter 3 in "Applied Microbial Physiology", Rhodes, P. M., et al., Eds., 1997, IRL Press, New York, pp. 53-73.

Hansen, E. H., et al., "De Novo Biosynthesis of Vanillin in Fission Yeast (*Schizosaccharomyces pombe*) and Baker's Yeast (*Saccharomyces cerevisiae*)", Applied and Environmental Microbiology, 2009, vol. 75, No. 9, pp. 2765-2774.

Havkin-Frenkel, D., et al., "Biotechnological Production of Vanillin", Chapter 3 in "Biotechnology in Flavor Production", Havkin-Frenkel, D., et al. Eds., 2008, Blackwell, Oxford, pp. 83-103.

Higgins, D. G., et al., "Fast and Sensitive Multiple Sequence Alignments on a Microcomputer", Comput. Appl. Biosci., 1989, vol. 5, No. 2, pp. 151-153.

Hua, D., et al., "Enhanced Vanillin Production from Ferulic Acid Using Adsorbent Resin", Appl. Microbiol. Biotechnol., 2007, vol. 74, pp. 783-790.

Ike, Y., et al., "Solid Phase Synthesis of Polynucleotides. VIII. Synthesis of Mixed Oligodeoxyribonucleotides by the Phosphotriester Solid Phase Method", Nucleic Acids Res., 1983, vol. 11, No. 2, pp. 477-488.

Itakura, K., et al., "Synthesis and Use of Synthetic Oligonucleotides", Ann. Rev. Biochem., 1984, vol. 53, pp. 323-356.

Itakura, K., et al., "Expression in *Escherichia coli* of a Chemically Synthesized Gene for the Hormone Somatostatin", Science, 1977, vol. 198, pp. 1056-1063.

Ishii, T., "Structure and Functions of Feruloylate Polysaccharides", Plant Science, 1997, vol. 127, pp. 111-127.

Ishikawa, H., et al., "Investigations on Lignins and Lignification. XXVIII. The Degradation by *Polyporus versicolor* and *Fomes fomentarius* of Aromatic Compounds Structurally Related to Softwood Lignin", Archives of Biochemistry and Biophysics, 1963, vol. 100, pp. 140-149.

Koenig, K., et al., "Xanthine Dehydrogenase and 2-Furoly-Coenzyme A Dehydrogenase from *Pseudomonas putida* Fu1: Two Molybdenum-Containing Dehydrogenases of Novel Structural Composition", Journal of Bacteriology, 1990, vol. 172, No. 10, pp. 5999-6009.

Kojima, Y., et al., "Studies on Pyrocatechase. I. Purification and Spectral Properties", J. Biol. Chem., 1967, vol. 242, No. 14, pp. 3270-3278.

Krings, U., et al., "Biotechnological Production of Flavours and Fragrances", Appl. Microbiol. Biotechnol., 1998, vol. 49, pp. 1-8.

Lee, E.-G., et al., "Directing Vanillin Production from Ferulic Acid by Increased Acetyl-CoA Consumption in Recombinant *Escherichia coli*", Biotechnology and Bioengineering, 2008, vol. 102, No. 1, pp. 200-208.

Lesage-Meessen, L., et al., "A Two-Step Bioconversion Process for Vanillin Production from Ferulic Acid Combining *Aspergillus niger* and *Pycnoporus cinnabarinus*", J. Biotechnol., 1996, vol. 50, pp. 107-113.

Martínez-Cuesta, M. del C., et al., "Functional Analysis of the Vanillin Pathway in a vdh-Negative Mutant Strain of *Pseudomonas fluorescens* AN103", Enzyme and Microbial Technology, 2005, vol. 37, pp. 131-138.

Muheim, A., et al., "Towards a High-Yield Bioconversion of Ferulic Acid to Vanillin", Appl. Microbiol. Biotechnol., 1999, vol. 51, pp. 456-461.

Nakazawa, T., "Travels of a *Pseudomonas*, from Japan Around the World", Environmental Microbiology, 2002, vol. 4, No. 12, pp. 782-286.

Narang, S. A., "DNA Synthesis", Tetrahedron, 1983, vol. 39, No. 1, pp. 3-22.

Narbad, A., et al., "Metabolism of Ferulic Acid via Vanillin Using a Novel CoA-Dependent Pathway in a Newly-Isolated Strain of *Pseudomonas fluorescens*", Microbiology, 1998, vol. 144, pp. 1397-1405.

Nelson, K. E., et al., "Complete Genome Sequence and Comparative Analysis of the Metabolically Versatile *Pseudomonas putida* KT2440", Environmental Microbiology, 2002, vol. 4, No. 12, pp. 799-808.

Oddou, J., et al., "Improvement of Ferulic Acid Bioconversion into Vanillin by Use of High-Density Cultures of *Pycnoporus cinnabarinus*", Appl. Microbiol. Biotechnol., 1999, vol. 53, pp. 1-6.

Okeke, B. C., et al., "Construction of Recombinants *Pseudomonas putida* BO14 and *Escherichia coli* QEFCA8 for Ferulic Acid Biotransformation to Vanillin", Journal of Bioscience and Bioengineering, 1999, vol. 88, No. 1, pp. 103-106.

Onaca, C., et al., "Degradation of Alkyl Methyl Ketones by *Pseudomonas veronii* MEK700", J. Bacteriol., 2007, vol. 189, No. 10, pp. 3759-3767.

Oosterveld, A., et al., "Characterization of Arabinose and Ferulic Acid Rich Pectic Polysaccharides and Hemicelluloses from Sugar Beet Pulp", Carbohydrate Research, 2000, vol. 328, pp. 185-197.

Overhage, J., et al., "Biochemical and Genetic Analyses of Ferulic Acid Catabolism in *Pseudomonas* sp. Strain HG199", Appl. Environ. Microbiol., 1999, vol. 65, No. 11, pp. 4837-4847.

Overhage, J., et al., "Highly Efficient Biotransformation of Eugenol to Ferulic Acid and Further Conversion to Vanillin in Recombinant Strains of *Escherichia coli*", Applied and Environmental Microbiology, 2003, vol. 69, No. 11, pp. 6569-6576.

Pearson, W. R., et al., "Improved Tools for Biological Sequence Comparison", Proc. Natl. Acad. Sci. USA, 1988, vol. 85, pp. 2444-2448.

Peng, X., et al., "Isolation and Characterization of Thermophilic Bacilli Degrading Cinnamic, 4-Coumaric, and Ferulic Acids", Applied and Environmental Microbiology, 2003, vol. 69, No. 3, pp. 1417-1427.

Plaggenborg, R., et al., "Potential of *Rhodococcus* Strains for Biotechnological Vanillin Production from Ferulic Acid and Eugenol", Appl. Microbiol. Biotechnol, 2006, vol. 72, pp. 745-755.

Plaggenborg, R., et al., "Functional Analyses of Genes Involved in the Metabolism of Ferulic Acid in *Pseudomonas putida* KT2440", Appl. Microbiol. Biotechnol., 2003, vol. 61, pp. 528-535.

Priefert, H., et al., "Biotechnological Production of Vanillin", Appl. Microbiol. Biotechnol., 2001, vol. 56, pp. 296-314.

Rao, S. R., et al., "Vanilla Flavour: Production by Conventional and Biotechnological Routes", Journal of the Science of Food and Agriculture, 2000, vol. 80, pp. 829-304.

Rosazza, J., et al., "Review: Biocatalytic Transformations of Ferulic Acid: An Abundant Aromatic Natural Product", Journal of Industrial Microbiology, 1995, vol. 15, pp. 457-471.

Simon, R., et al., "A Broad Host Range Mobilization System for In Vivo Genetic Engineering: Transposon Mutagenesis in Gram Negative Bacteria", Bio/Technology, 1983, vol. 1, pp. 784-791.

Sinha, A. K., et al., "Development and Validation of an RP-HPLC Method for Quantitative Determination of Vanillin and Related Phenolic Compounds in *Vanilla planifolia*", J. Sep. Sci., 2007, vol. 30, pp. 15-20.

Stentelaire, C., et al., "Short Communication: By-Passing of Unwanted Vanillyl Alcohol Formation Using Selective Adsorbents to Improve Vanillin Production with *Phanerochaete chrysosporium*", World J. Microbiol. Biotechnol., 1998, vol. 14, pp. 285-287.

Tilay, A., et al., "Production of Biovanillin by One-Step Biotransformation Using Fungus *Pycnoporous cinnabarinus*", J. Agric. Food Chem., 2010, vol. 58, pp. 4401-4405.

Williams, P. A., et al., "Metabolism of Benzoate and the Methylbenzoates by *Pseudomonas putida* (*arvilla*) mt-2: Evidence for the Existence of a TOL Plasmid", J. Bacteriol., 1974, vol. 120, No. 1, pp. 416-423.

Yanisch-Perron, C., et al., "Improved M13 Phage Cloning Vectors and Host Strains: Nucleotide Sequences of the M13mp18 and pUC19 Vectors", Gene, 1985, vol. 33, pp. 103-119.

(56) References Cited

OTHER PUBLICATIONS

Yoon, S.-H., et al., "Enhanced Vanillin Production from Recombinant *E. coli* Using NTG Mutagenesis and Adsorbent Resin", Biotechnol. Prog., 2007, vol. 23, pp. 1143-1148.
Overhage, J., et al., "Biotransformation of Eugenol to Vanillin by a Mutant of *Pseudomonas* sp. Strain HR199 Constructed by Disruption of the Vanillin Dehydrogenase (vdh) Gene", Appl. Microbiol. Biotechnol., 1999, vol. 52, pp. 820-828.
Di Gioia, D., et al., "Metabolic Engineering of *Pseudomonas fluorescens* for the Production of Vanillin from Ferulic Acid", Journal of Biotechnology, 2011, vol. 156, pp. 309-316.
International Preliminary Report on Patentability for PCT/EP2014/065659 dated Jan. 26, 2016.

US 10,036,044 B2

GENETIC ENGINEERING OF *PSEUDOMONAS PUTIDA* KT2440 FOR RAPID AND HIGH YIELD PRODUCTION OF VANILLIN FROM FERULIC ACID

RELATED APPLICATIONS

This application is a national stage application (under 35 U.S.C. § 371) of PCT/EP2014/065659, filed Jul. 22, 2014, which claims benefit of European Application No. 13177401.0, filed Jul. 22, 2013.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074012 0337. The size of the text file is 177 KB, and the text file was created on Jan. 20, 2016.

The present invention relates to an improved biocatalytic process for producing vanillin from ferulic acid based on a genetically engineered *Pseudomonas* strains, as well as to said *Pseudomonas* strains.

TECHNICAL BACKGROUND

Vanillin (4-hydroxy-3-methoxybenzaldehyde), the organoleptic compound of the *vanilla* flavor, is one of the quantitative most widely used flavoring agents worldwide. Its demand has long exceeded the supply by the botanical source *Vanilla planifolia*. At present, most of the vanillin is synthesized chemically from guiacol, which originates from fossile raw materials, and lignin, a component in waste material from the wood pulp industry (Ramachandra Rao and Ravishankar, 2000). However, the demand for this "nature-identical" vanillin, which is mostly used in the food and beverage industry, is shifted towards the "natural" vanillin due to a rising health- and nutrition-consciousness of the costumers. Thus, biotechnological production of "natural" vanillin becomes more and more important (reviewed by Krings and Berger, 1998; Priefert et al., 2001).

Efforts have been made to produce vanillin by in vitro cultured *Vanilla planifolia* cells (Davidonis and Knorr, 1991). A de novo synthesis was also implemented using genetically modified yeast strains (Hansen et al., 2009). The main focus, however, was put on the biotransformation using isolated enzymes or different prokaryotic microorganisms as whole cell biocatalysts (Havkin-Frenkel and Belanger, 2008; Berger, 2009).

Besides lignin and phenolic stilbenes, like eugenol, the biotransformation of ferulic acid to vanillin is the most intensively studied method to produce "natural" vanillin (reviewed by Rosazza et al., 1995; Priefert et al., 2001). The precursor ferulic acid (3-(4-hydroxy-3-methoxy-phenyl) prop-2-enoic acid), a hydroxycinnamic acid, is a highly abundant substance since it is a constituent of many plant cell walls (Ishikawa et al., 1963; Escott-Watson and Marais, 1992; Ishii, 1997; Oosterveld et al., 2000). Many different microorganisms have been evaluated for the production of vanillin from ferulic acid comprising recombinant strains of *E. coli, Pseudomonas* ssp., *Rhodococcus* ssp., *Bacillus subtilis, Aspergillus niger, Pycnoporous cinnabarinus, Amycolatopsis* ssp. and *Streptomyces* ssp. (Lesage-Meessen et al., 1996; Okeke and Venturi, 1999; Muheim and Lerch, 1999; Achterholt et al., 2000; Overhage et al., 2003; Peng et al., 2003; Plaggenborg et al., 2006; Yoon et al., 2007; Barghini et al., 2007; Hua et al., 2007; Di Gioia et al., 2010; Tilay et al., 2010; Fleige et al., 2013). However, in most cases vanillin yields were low and biotransformation reactions slow. The low yields can mostly be ascribed to the high toxicity of vanillin (Krings and Berger, 1998). Enhanced vanillin production with adsorbent resins improved the vanillin levels up to 19.2 gl$^{-1}$, but the molar yield of about 43% was rather low (Hua et al., 2007). Other drawbacks were inefficient heterologous gene expression and plasmid instabilities. A focus was also set on prevention of further degradation of vanillin to vanillyl alcohol or vanillic acid (Stentelaire et al., 1997; Bonnin et al., 1999; Oddou et al., 1999; Civolani et al., 2000; Overhage et al., 2000).

Bacteria from the genus *Pseudomonas* show a broad metabolic versatility as they can use a wide range of aromatic molecules as sole carbon sources (Clarke, 1982). The ferulic acid catabolism in *Pseudomonas* sp. strain HR199, *P. fluorescens* BF13 and *P. putida* KT2440 occurs via a coenzyme A-dependent, non-R-oxidative pathway as depicted in FIG. 1 (Narbad and Gasson, 1998; Gasson et al., 1998; Overhage et al., 1999b; Plaggenborg et al., 2003; Calisti et al., 2008). First, ferulic acid becomes activated to feruloyl-CoA catalyzed by feruloyl-CoA synthetase (EC 6.2.1.34; encoded by fcs). Second, the CoA thioester is hydrated and cleaved to vanillin and acetyl-CoA catalyzed by enoyl-CoA hydratase/aldolase (EC 4.2.1.101; encoded by ech). The vanillin dehydrogenase (EC 1.2.1.67; encoded by vdh), oxidizes vanillin to vanillic acid which is further catabolized to protocatechuic acid by vanillate-O-demethylase (EC 1.14.13.82; encoded by vanAB). Overhage et al. (1999b) also proposed a second route over 4-hydroxy-3-methoxyphenyl-β-ketopropionyl-CoA and vanillyl-CoA catalyzed by enzymes encoded by PP_3355 (aat) and probably PP_3354.

A recent study has used a metabolic engineered strain of *P. fluorescens* for the production of vanillin from ferulic acid (Di Gioia et al., 2010). By deletion of the gene vdh for the vanillin dehydrogenase and by overexpression of the structural genes fcs and ech on a low-copy vector the authors were able to produce up to 8.41 mM vanillin from 10 mM ferulic acid which was the highest final titer of vanillin produced with a *Pseudomonas* strain so far.

The prior art approaches for the microbial production of vanillin still suffer from one or more of the following drawbacks: low conversion rate of ferulic acid, low molar yield of vanillin, significant by-product formation.

The problem underlying the present invention therefore was the provision of a method which avoids at least one of the above-mentioned drawbacks.

SUMMARY OF THE INVENTION

The above-mentioned problem was, surprisingly solved by providing genetically engineering strains of bacteria of the genus *Pseudomoas* which have the ability to catalyse the catabolism of ferulic acid via a coenzyme A-dependent, non-β-oxidative pathway to vanillin.

In a particular embodiment, the non-pathogenic, fully sequenced *Pseudomonas putida* strain KT2440 (ATCC 47054) (Nelson et al., 2002) was used, which is a plasmid-free derivative of the biosafety strain *P. putida* mt-2 (Kojima et al., 1967; Williams and Murray, 1974; Nakazawa, 2002). By genetic modification a highly efficient way for the biotransformation of ferulic acid to vanillin using plasmid-free, resting *P. putida* mutant cells could be established. In particular, genetic manipulation of *P. putida* KT2440 using the upp counterselection system (Graf and Altenbuchner, 2011) led to cells which were able to rapidly convert ferulic acid to vanillin accompanied with molar yields up to 86%, high productivities and only little by-product formation.

Said non-pathogenic *Pseudomonas putida* strain KT2440 was genetically optimized to convert ferulic acid to vanillin in a particular manner. Deletion of the vanillin dehydrogenase gene (vdh) was not sufficient to prevent vanillin degradation. Additional inactivation of a molybdate transporter, identified by transposon mutagenesis, led to a strain incapable to grow on vanillin as sole carbon source. The bioconversion was further optimized by enhanced chromosomal expression of the structural genes for feruloyl-CoA synthetase (fcs) and enoyl-CoA hydratase/aldolase (ech) by introduction of the strong tac promoter system. Further genetic engineering led to high initial conversion rates and molar vanillin yields up to 86% within just 3 h accompanied with very low by-product levels. This represents the highest productivity and molar vanillin yield gained with a *Pseudomonas* strain so far. Together with its high tolerance for ferulic acid the newly developed, plasmid-free *Pseudeomonas* strains represent promising candidates for the biotechnological production of vanillin.

DETAILED DESCRIPTION OF THE INVENTION

A. General Definitions

Figure 1:
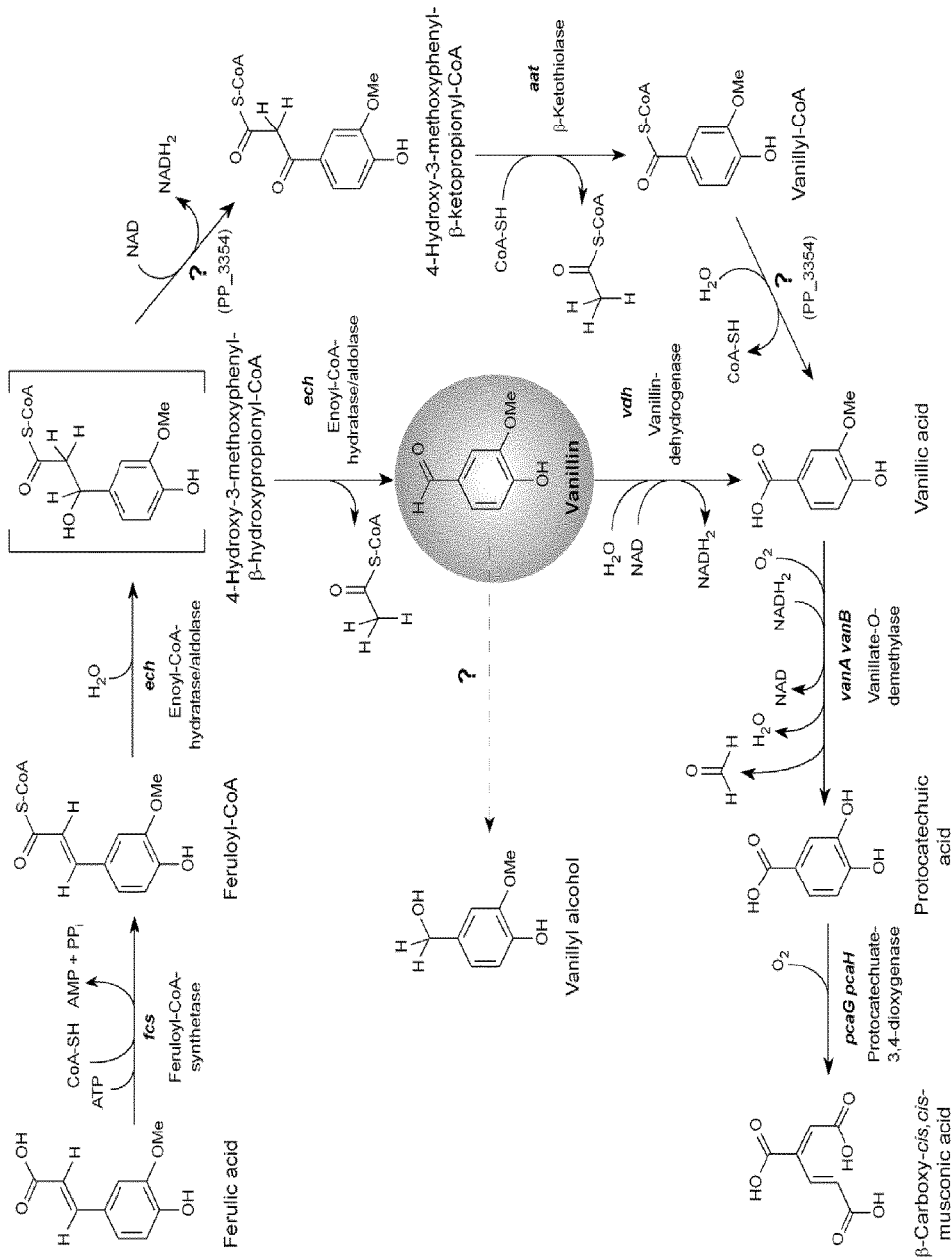
FIG. 1: Proposed route for the catabolism of ferulic acid over vanillin in *Pseudomonas* strains. The alternative route from 4-hydroxy-3-methoxyphenyl-β-hydroxypropionyl-CoA to vanillic acid is shown on the right (proposed by Overhage et al., 1999b). The reduction of vanillin to vanillyl alcohol is depicted by a dashed arrow. Question marks symbolize reactions catalyzed by unknown enzymes.

"Deregulation" has to be understood in its broadest sense (up-regulation or down-regulation, amplification or attenuation, increase or decrease of activity/function), and comprises an increase or decrease or complete switch-off or the switch on of a target, as for example an enzyme (target enzyme) activity or other metabolically active proteins (target protein) activity, by different means well known to those in the art.

Suitable manipulations may occur on the protein/enzyme level altering amino acid sequences or amino acid residues; or may occur on the level of nucleic acids, altering for example genetic information or regulatory genetic element. Suitable methods comprise for example an increase or decrease of the copy number of gene and/or enzyme/protein molecules in a genetically engineered organism, or the modification of another feature of the enzyme affecting its enzymatic activity or of the protein, affecting its biological, as for example metabolic, activity, which then results in the desired effect on the metabolic pathway at issue.

Suitable genetic manipulation can also include, but is not limited to, altering or modifying regulatory sequences or sites associated with expression of a particular gene (e.g., by removing or introducing strong promoters, inducible promoters or multiple promoters), modifying the chromosomal location of a particular gene, altering nucleic acid sequences adjacent to a particular gene such as a ribosome binding site or transcription terminator, decreasing or increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, or other methods to knock-out or block expression of the target protein).

More particularly "deregulate", "deregulated" and "deregulation" refers to alterations or modifications of at least one gene in a microorganism, wherein the alteration or modification results in increasing efficiency of vanillin production in the microorganism relative to vanillin production in absence of the alteration or modification. In some embodiments, a gene that is altered or modified encodes an enzyme in a biosynthetic pathway or a transport protein, such that the level or activity of the biosynthetic enzyme in the microorganism is altered or modified or that the transport specificity or efficiency is altered or modified. In some embodiments, at least one gene that encodes an enzyme in a biosynthetic pathway is altered or modified such that the level or activity of the enzyme is enhanced or increased relative to the level in presence of the unaltered or wild type gene. Deregulation also includes altering the coding region of one or more genes to yield, for example, an enzyme that is feedback resistant or has a higher or lower specific activity. Also, deregulation further encompasses genetic alteration of genes encoding transcriptional factors (e.g., activators, repressors), which regulate expression of genes coding for enzymes or transport proteins. More specifically, deregulation may result in "decreased" enzyme activity, wherein the resulting enzyme activity is less than 100% of enzyme activity as observed in the non-deregulated state, or is "switched-off", i.e. reversibly or irreversibly, no longer present or at least no longer detectable by a conventional analytical tool, like an enzyme activity assay.

A particular way of an up-regulation is the amplification of a target gene, in particular by performing an "up"-mutation which increases the gene activity, e.g. by gene amplification using strong expression signals and/or point mutations which enhance or increase the enzymatic activity or metabolic activity of a protein.

A preferred way of a down-regulation is the attenuation of a target gene, in particular by performing a "down"-mutation which decreases the gene activity e.g. by gene deletion or disruption, using weak expression signals and/or point mutations which destroy or decrease the enzymatic activity or metabolic activity of a protein.

In particular a gene can be manipulated so that one or more nucleotides are being deleted from the chromosome of the host organism. The decreased activity of a gene product can also be obtained by introducing one or more gene mutations which lead to a decreased activity of the gene product. The decreased activity can be a reduction of the enzymatic or other metabolic activity by >50% of the non-mutated or unaltered enzyme activity, or reduction of the activity by >90%, or more preferably a reduction of the activity by >95%, or more preferably a reduction of the activity by >98%, or even more preferably a reduction of the activity by >99% or even more preferably a reduction of the activity by >99.9%.

The increased activity of a gene product can also be obtained by introducing one or more gene mutations which lead to an increased activity of the gene product. The increased activity can be a increase of the enzymatic or other metabolic activity by, for example a factor of 1 to 1.000 of the non-mutated or unaltered enzyme activity, or increase of the activity by a factor of 2 to 100 or more preferably an increase of the activity by a factor of 5 to 50 or 10 to 20.

The term "heterologous" or "exogenous" refers to proteins, nucleic acids and corresponding sequences as described herein, which are introduced into or produced (transcribed or translated) by a genetically manipulated (engineered) microorganism as defined herein and which microorganism prior to said manipulation did not contain or did not produce said sequence. In particular said microorganism prior to said manipulation may not contain or express said heterologous enzyme activity, or may contain or express an endogenous enzyme of comparable activity or specificity, which is encoded by a different coding sequence or by an enzyme of different amino acid sequence, and said endogenous enzyme may convert the same substrate or substrates as said exogenous enzyme.

A "microorganism" refers to eukaryotes and in particular prokaryotes, and more particular bacteria.

A microorganism "derived from a parent microorganism" microorganism refers to a microorganism modified by any type of manipulation, or combination of such manipulations, selected from chemical, biochemical or microbial, in particular genetic engineering techniques. In the latter case they are referred to as "genetically engineered" or "genetically modified" microorganisms. Said manipulation results in at least one change of a biological feature of said parent microorganism. As an example, the coding sequence of a heterologous enzyme may be introduced into said organism or a coding sequence of the parent microorganism may be deleted. By said change at least one feature may be added to, replaced in or deleted from said parent microorganism. Said change may, for example, result in an altered metabolic feature of said microorganism, so that, for example, a substrate of an enzyme expressed by said microorganism (which substrate was not utilized at all or which was utilized with different efficiency by said parent microorganism) is metabolized in a characteristic way (for example, in different amount, proportion or with different efficiency if compared to the parent microorganism), and/or a metabolic final or intermediary product is formed by said modified microorganism in a characteristic way (for example, in different amount, proportion or with different efficiency if compared to the parent microorganism).

A microorganism can be physically or environmentally "altered" or "modified" to express a gene product at an increased or lower level relative to level of expression of the gene product by the starting microorganism. For example, a microorganism can be treated with or cultured in the presence of an agent (chemical or genetic) known or suspected to increase or decrease the transcription and/or translation of a particular gene and/or translation of a particular gene product such that transcription and/or translation are increased or decreased. Alternatively, a microorganism can be cultured at a temperature selected to increase or decrease transcription and/or translation of a particular gene and/or translation of a particular gene product such that transcription and/or translation are increased or de-creased.

"Genetically modified" refers to a microorganism altered in the above sense by means of genetic engineering techniques available in the art, as for example transformation, mutation, homologous recombination.

The term "capable of utilizing" refers to the ability of a microorganism of the invention to convert a substrate, as for example ferulic acid into at least one structurally and/or sterically different chemical product.

An "enzyme activity involved in or associated with the fermentative conversion of ferulic acid to vanillin" means any catalytic or regulatory activity of an enzyme which influences the conversion of ferulic acid into vanillin and or by-products, as may be determined by anyone of the set of parameters as defined herein below.

The different yield parameters ("Yield" or YP/S; "Specific Productivity Yield"; or Space-Time-Yield (STY)) are well known in the art and are determined as described for example by Song and Lee, 2006.

"Yield" and "YP/S" (each expressed in mass of product produced/mass of material consumed) are herein used as synonyms.

The specific productivity-yield describes the amount of a product, like Vanillin, that is produced per h and L fermentation broth per g of biomass. The amount of wet cell weight stated as WCW describes the quantity of biologically active microorganism in a biochemical reaction. The value is given as g product per g WCW per h (i.e. $g/gWCW^{-1}\ h^{-1}$).

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean an aqueous solution which is based on a fermentative process and has not been worked up or has been worked up, for example, as described herein.

A "recombinant host" may be any prokaryotic or eukaryotic cell, which contains either a cloning vector or expression vector. This term is also meant to include those prokaryotic or eukaryotic cells that have been genetically engineered to contain the cloned gene(s) in the chromosome or genome of the host cell.

The term "recombinant microorganism" includes a microorganism (e.g., bacteria, yeast, fungus, etc.) or microbial strain, (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism or "parent" microorganism which it was derived from.

Particular enzymes involved in the vanillin biosynthesis pathway forming basis of the present invention encompass:
Feruloyl-CoA synthetase (EC 6.2.1.34; encoded by fcs).
Enoyl-CoA hydratase/aldolase (EC 4.2.1.101; encoded by ech).
Vanillin dehydrogenase (EC 1.2.1.67; encoded by vdh),
β-Ketothiolase (EC 2.3.1.16 encoded by aat)
Acyl-CoA-Hydrolase (EC 3.1.2.20 encoded by PP_3354
Molybdate transporter (encoded by modABC)
B. Particular Embodiments The present invention refers in particular to the following embodiments:

1. A biocatalytic process for producing vanillin from ferulic acid, wherein
a) a genetically engineered bacterial strain of the genus *Pseudomonas* having the ability to convert ferulic acid to vanillin is cultured in the presence of ferulic acid; and
b) optionally vanillin thereby formed is isolated from the culture medium; wherein said genetically engineered bacterial strain has a reduced, diminished ability, to grow on vanillin as the sole carbon source. Preferably a growth on vanillin as the sole carbon source is not observed for a genetically engineered strain.

2. The process according to embodiment 1, wherein said genetically engineered strain contains at least the following genetic modification:
i) down-regulation, in particular complete or quantitative inhibition, of cellular molybdate uptake, which preferably results in said reduced ability to grow on vanillin 3. The process according to embodiment 2, wherein said genetically engineered stain-contains additionally the following genetic modification:
ii) down-regulation of the vanillin dehydrogenase activity in particular the corresponding gene (vdh), for example by partial or complete deletion of corresponding genetic information.

4. The process of one of the embodiments 1 to 3, wherein the cellular molybdate uptake is down-regulated by down-regulating periplasmatic molybdate binding protein (modA), for example by partial or complete deletion of corresponding genetic information.

5. The process according to any one of embodiments 1 to 4, wherein the cellular molybdate uptake is down-regulated by deletion of the operon modABC.

6. The process according to any one of the preceding embodiments, wherein at least one of the following enzyme activities, and in particular the genes for
iii) feruloyl-CoA synthetase and
iv) enoyl-CoA hydratase
is up-regulated. Up-regulation may for example be accomplished by increasing the copy number of such genes chromosomally or by means of introducing recombinant expression vectors carrying said genetic information, or, by modifying the gene expression, in particular by using a strong promoter.

7. The process according to embodiment 6, wherein chromosomal expression of the genes for feruloyl-CoA synthetase (fcs) and enoyl-CoA hydratase (ech) is up-regulated.

8. The process according to embodiment 7, wherein expression of the genes for feruloyl-CoA synthetase (fcs) and enoyl-CoA hydratase (ech) is under the control of a regulatory element comprising a strong, optionally inducible, promoter, in particular the strong tac promoter, optionally in combination with lad or $lacI^q$ in particular the strong tac promoter in combination with the $lacL^q$ element.

9. The process according to one of the preceding embodiments, wherein additionally at least one of the following enzyme activities, in particular at least one of the corresponding genes is down-regulated:
v) aldehyde dehydrogenase PP_2680 and/or PP_0545 vi) benzaldehyde dehydrogenase PP_1948
In particular, down-regulation may be accomplished by partial or complete chromosomal deletion of corresponding genetic information.

10. The process according to any one of the preceding embodiments, wherein additionally at least one of the following enzyme activities, in particular at least one of the corresponding genes is down-regulated:
vii) beta-ketothiolase PP_3355 (aat)
viii) acyl-CoA dehydrogenase PP_3354.
In particular, down-regulation may be accomplished by partial or complete chromosomal deletion of corresponding genetic information.
11. The process according to any one of the preceding embodiments, wherein the microbial strain to be genetically engineered is a strain of *Pseudomonas putida*.
12. The process according to any one of the preceding embodiments, wherein said stain of *Pseudomonas putida* is genetically engineered by down-regulating the surface adhesion protein (lapA) in particular, by down-regulating of the corresponding gene. In particular, down-regulation may be accomplished by partial or complete deletion of corresponding genetic information.
13. The process of one of the preceding embodiments, which is carried out aerobically and/or at a temperature in the range of 10 to 40° C., or 20 to 30° C. and/or at a pH in the range of 6 to 8 or 6.5 to 7.5.
14. The process of one of the preceding embodiments, wherein the reaction is carried out at an initial ferulic acid concentration of 1 to 50 mM, in particular 5 to 15 or 8 to 12 mM, like about 10 mM, preferably in an aqueous medium.
15. The process of one of the preceding embodiments, wherein the reaction is performed in whole cells of said bacterial strains or a cell homogenate thereof or a fraction obtained from said homogenate.
16. The process of anyone of the preceding embodiments, wherein said bacterial strain is applied in free or immobilized form.
17. The process of one of the preceding embodiments performed continuously or discontinuously.
18. The genetically engineered *Pseudomonas* strain as defined in anyone of the claims 1 to 12.
19. The genetically engineered *Pseudomonas* strain of claim 18, which is obtained by genetic engineering of *Pseudomonas putida*, in particular from *Pseudomonas putida* KT2440, wherein said genetically engineered strain is preferably plasmid-free.
20. The genetically engineered *Pseudomonas* stain of claim 19, selected from GN23, GN235, GN237, GN275, GN276, GN299, GN347, GN440, GN441 and GN442; or a functional variant or mutant strain thereof, which retains the ability to convert ferulic acid to vanillin, and/or which does not grow on vanillin as sole carbon source and/or wherein molybdate uptake is down-regulated.
21. In another embodiment a bioconversion system of the invention, for example with *P. putida* GN442, may comprise suitable adsorbent resins to reduce the toxicity of the product vanillin.

C. Other Embodiments of the Invention

C.1 Deregulation of Further Genes

The fermentative production of Vanillin with a recombinant Pseudomionas strain as described herein may be further improved if it is combined with the deregulation of at least one further gene as involved in the non-beta-oxidative ferulic acid catabolic pathway as depicted in attached FIG. 1.

C.2 Proteins According to the Invention

While the preferred embodiments of the invention are based on an approach which deregulated enzyme or protein activities by gene sequence deletions and/or increasing the expression rates of particular enzymes The invention is not limited thereto.

In addition it may be possible to reach similar improvements by down-regulation of enzyme/protein activities by performing suitable mutations into one or more amino acid sequences identified herein. Up-regulation may be performed by generating protein/enzyme mutants with improved activity.

Therefore the invention in this context also relates to "functional equivalents" or "analogs" or "functional mutations" of the specifically described enzymes/proteins.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more, like 1 to 20, 1 to 15 or 5 to 10 amino acid additions, substitutions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the poly-peptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, (1988).

The % identity values may also be calculated from BLAST alignments, algorithm blastp (protein-protein BLAST) or by applying the Clustal setting as given below.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides ac-cording to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983); Itakura et al. (1984) (a); Itakura et al., (1984) (b); Ike et al. (1983)).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992); Delgrave et al. (1993)).

C.3 Coding Nucleic Acid Sequences

The invention also relates to nucleic acid sequences that code for enzymes/proteins as defined herein and which may be applied to perform the required genetic engineering manipulations.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. ((1989))) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: www(dot)ebi(dot)ac(dot)uk/Tools/clustalw/index.html#and the following settings

| | |
|---|---|
| DNA Gap Open Penalty | 15.0 |
| DNA Gap Extension Penalty | 6.66 |
| DNA Matrix | Identity |

| | |
|---|---|
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above proteins/enzymes and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homo-logues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM tri-sodium citrate), 50 mM sodium phosphate (pH 7.6), 5×Denhardt Solution, 10% dextran sulfate and 20 g/ml denatured, sheared salmon sperm DNA, followed by wash-ing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for ex-ample allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

C.4 Constructs According to the Invention

The invention also relates to constructs like expression constructs, containing, under the genetic control of regulatory nucleic acid sequences, a nucleic acid sequence coding for a polypeptide or fusion protein applicable in the invention; as well as vectors comprising at least one of these constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined.

Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid which, functionally associated with a nucleic acid that is to be transcribed, regulates the transcription of this nucleic acid.

"Functional" or "operative" association means, in this context, for example the sequential arrangement of one of the nucleic acids with promoter activity and of a nu-cleic acid sequence that is to be transcribed and optionally further regulatory elements, for example nu-cleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophy-complementing genes, optionally for selection on the construct.

Examples of suitable regulatory sequences are contained in promoters such as cos-, tac-, trp-, tet-, trp-tet-, lpp-, lac-, lpp-lac-, lacIq-, T7-, T5-, T3-, gal-, trc-, ara-, rhaP (rhaP-BAD)SP6-, lambda-PR- or in the lambda-PL promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III113-B1, Δgt11 or pBdCI; in nocardioform actinomycetes pJAM2; in *Streptomyces* pIJ101, pIJ364, pIJ702 or pIJ361; in *bacillus* pUB110, pC194 or pBD214; in *Corynebacterium* pSA77 or pAJ667; in fungi pALS1, pIL2 or pBB116; in yeasts 2alphaM, pAG-1, YEp6, YEp13 or pEMBLYe23 or in plants pLGV23, pGHlac+, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al.) 1985.

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in J. Sambrook (1989) as well as in T. J. Silhavy, et al. (1984) and in Ausubel, F. M. et al., (1987).

The recombinant nucleic acid construct or gene construct is inserted advant-geously in a host-specific vector for expression in a suitable host organism, to permit optimum expression of the genes in the host. Vectors are well known to a person skilled in the art and will be found for example in "Cloning Vectors" Pouwels P. H. et al., (1985).

C.5 Hosts that can be Used According to the Invention

Depending on the context, the term "microorganism" means the starting micro-organism (wild-type) or a genetically modified microorganism according to the invention, or both.

Genetically engineered Host cells may be modified exclusively on the chromosomal level, may contain vectors, as for example plasmids carrying the required genetic information or may be modified by a combination of both.

Common cloning and transfection methods that are familiar to a person skilled in the art are used, for example co-precipitation, protoplast fusion, electroporation, retroviral transfection and the like, in order to secure expression of a nucleic acids in the respective expression system. Suitable systems are described for example in F. Ausubel et al., (1997), or Sambrook et al., (1989).

The parent microorganisms are typically those which have the ability to produce vanillin, from ferulic acid. Typically these are bacteria of the genus *Pseudomonas*.

Non-limiting examples of suitable strains of the genus *Pseudomonas*, are those, which carry the above-identified genes ech and fcs, like:

P. putida KT2440 ATCC 47054*Pseudomonas* sp. strain HR199, and *P. fluorescens* BF13.

ATCC designates American type strain culture collection, FERM BP designates the collection of National institute of Bioscience and Human-Technology, Agency of Industrial Science and Technology, Japan.

C.6 Fermentative Production of Vanillin

The invention also relates to methods for the fermentative production of vanillin.

A fermentation as used according to the present invention can, for example, be performed in stirred fermentors, bubble columns and loop reactors. A comprehensive overview of the possible method types including stirrer types and geometric designs can be found in "Chmiel: Bioprozesstechnik: Einfuhrung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hy-drogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

The particular composition may be adapted to the type of Microorganism applied. In the fermentation. Media compositions useful for fermentations based of *Pseudomonas* strains are known in the art. For example LB Medium is a typical medium applicable to such strains.

3.6 Vanillin Isolation

The methodology of the present invention can further include a step of recovering Vanillin. The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skilful selection of pressure and temperature levels for a multistage evaporation in particular enables saving of energy.

The following examples only serve to illustrate the invention. The numerous possible variations that will become immediately evident to a person skilled in the art after heaving considered the disclosure provided herein also fall within the scope of the invention.

EXPERIMENTAL PART

A) Materials and Methods
Plasmids, Bacterial Strains and Growth Conditions

The bacterial strains and plasmids used in this invention are shown in Table 1. *P. putida* strains were grown at 30° C. and *E. coli* JM109 (Yanisch-Perron et al., 1985) at 37° C. in LB medium (Bertani, 1951). For selection of plasmids 50 μg ml$^{-1}$ kanamycin (Kan) was added. During the deletion procedure and for the tolerance tests M9 minimal medium was used for growth of *P. putida* strains (48 mM Na$_2$HPO$_4$×7 H$_2$O, 22 mM KH$_2$PO$_4$, 8.6 mM NaCl, 18.7 mM NH$_4$Cl), supplemented with 0.2% glucose, 1 mM MgSO$_4$, 0.1 mM CaCl$_2$, 6 μM thiamine hydrochloride and 20 μg ml$^{-1}$ 5-fluorouracil (5-FU; prepared as a stock solution of 100 mg ml$^{-1}$ in dimethyl sulfoxide [DMSO]).

TABLE 1

Bacterial strains and plasmids used in this invention

| Strain or plasmid | Genotype or relevant characteristics | Reference or source |
|---|---|---|
| Strains | | |
| *E. coli* | | |
| JM109 | recA1, supE44, endA1, hsdR17, gyrA96, relA1, thi, Δ(lac-proAB), F' [traD36 proAB+ lacI$^q$ lacZΔM15] | Yanisch-Perron et al. (1985) |
| S17.1 | recA pro hsdR RP4-2-Tc::Mu-Km::Tn7 | (Simon et al. (1983) |
| *P. putida* | | |
| KT2440 | wild type | ATCC 47054 |
| ΔUPP4 | Δupp | Graf and Altenbuchner (2011) |
| GN23 | Δupp ΔPP_0166-0168 | This invention |
| GN235 | Δupp ΔPP_0166-0168 Δvdh | This invention |
| GN275 | Δupp ΔPP_0166-0168 Δvdh modA::mini-Tn5495 | This invention |
| GN276 | Δupp ΔPP_0166-0168 Δvdh ΔPP_3827-3832 | This invention |
| GN299 | Δupp ΔPP_0166-0168 Δvdh ΔPP_3827-3832 lacI$^q$-P$_{tac}$-ech-fcs | This invention |
| GN347 | Δupp 0166-0168 Δvdh ΔPP_3827-3832 ΔPP_3354 ΔPP_3355 lacI$^q$-P$_{tac}$-ech-fcs | This invention |
| GN440 | Δupp ΔPP_0166-0168 Δvdh ΔPP_3827-3832 ΔPP_2680 lacI$^q$-P$_{tac}$-ech-fcs | This invention |
| GN441 | Δupp ΔPP_0166-0168 Δvdh ΔPP_3827-3832 ΔPP_2680 ΔPP_0545 lacI$^q$-P$_{tac}$-ech-fcs | This invention |
| GN442 | Δupp ΔPP_0166-0168 Δvdh ΔPP_3827-3832 ΔPP_2680 ΔPP_0545 ΔPP_1948 lacI$^q$-P$_{tac}$-ech-fcs | This invention |
| Plasmids | | |
| pCro2a | mini-Tn5495 delivery vector | Onaca et al. (2007) |
| pJOE5304.1 | expression vector with lacI$^q$-P$_{tac}$-eGFP | laboratory stock |
| pJOE6261.2 | pIC20HE (Altenbuchner et al., 1992)backbone with a kanamycin resistance gene and a copy of upp from *P. putida* KT2440 | Graf and Altenbuchner (2011) |
| pNG53.1 | pJOE6261.2 with the upstream region of PP_0166 and downstream region of PP_0168 cloned into BamHI site | This invention |
| pNG173.1 | pJOE6261.2 with the up- and downstream regions of vdh cloned into BamHI site | This invention |
| pNG260.4 | pJOE6261.2 with the upstream region of PP_3827 and downstream region of PP_3832 cloned into BamHI site | This invention |
| pNG276.1 | pJOE6261.2 with the up- and downstream regions of PP_2680 cloned into SalI site | This invention |
| pNG281.1 | pJOE5304.1 derivative with lacI$^q$-P$_{tac}$-ech | This invention |
| pNG283.5 | pJOE6261.2 with 900 bp of ech, P$_{tac}$, lacI$^q$ and the downstream region of ech cloned into BamHI site | This invention |
| pNG338.1 | pJOE6261.2 with the up- and downstream regions of PP_0545 cloned into BamHI site | This invention |
| pNG340.2 | pJOE6261.2 with the upstream region of PP_3354 and downstream region of aat cloned into BamHI site | This invention |
| pNG412.1 | pJOE6261.2 with the up- and downstream regions of PP_1948 cloned into BamHI site | This invention |

Chemicals and Other Materials

Chemicals used in this invention were of analytical grade and purchased from Carl Roth GmbH+Co. KG (Karlsruhe, Germany), Sigma-Aldrich Corporation (Taufkirchen, Germany) and Merck KGaA (Darmstadt, Germany). In particular, 5-FU, ferulic acid, vanillin, vanillic acid and vanillyl alcohol were purchased from Sigma-Aldrich. Synthetic DNA oligonucleotides (Table 2a) were purchased from Eurofins MWG Operon GmbH (Ebersberg, Germany). Restriction enzymes and DNA modifying enzymes were purchased from Roche Diagnostics Deutschland GmbH (Mannheim, Germany), New England Biolabs GmbH (Frankfurt am Main, Germany) and Fermentas GmbH (part of Thermo Fisher Scientific, St. Leon-Rot, Germany). PCRs were run with High Fidelity PCR Enzyme Mix from Fermentas GmbH on a TPersonal Thermocycler from Biometra GmbH (Goettingen, Gemany).

TABLE 2a

Oligonucleotide primers used in this invention

| Primer | SEQ ID NO: | Sequence (5' → 3')[a] |
|---|---|---|
| s6007 | 1 | AAAAAAGGATCCTAAAGCAATGGCGAAACCC |
| s6008 | 2 | AAAAAAAAGCTTACCCAGTACGCCAACAGCCT |
| s6009 | 3 | AAAAAAAAGCTTGACAGTGCCGGCAAGCCA |
| s6010 | 4 | AAAAAAGGATCCGTGGTCTGTCAGCTGTCCTT |
| s6534 | 5 | AAAAAAGGATCCTAAAGCACGATGCCGAGG |
| s6535 | 6 | AAAAAAGAATTCTAGACCTCCGGCAAGATGA |
| s6536 | 7 | AAAAAAGAATTCCATGCTCATTCCTCTTGTTG |
| s6537 | 8 | AAAAAAGGATCCTTATGCGATTCGGCTAGAGA |
| s6882 | 9 | AAAAAAGGATCCCCGCGCTTGTCGATATCC |
| s6883 | 10 | AAAAAACCATGGCATGCGATTCTCCTTGCGT |
| s6884 | 11 | AAAAAACCATGGTGAGCGTCACCCGAGGG |
| s6885 | 12 | AAAAAAGGATCCGGTCAGTCAGCCTGTTGAT |
| s6927 | 13 | AAAAAAGTCCAGACAAGGACGGCGGCAAGG |
| s6928 | 14 | AAAAAATGTACACATGCTGAGCCTCTGCGG |
| s6930 | 15 | AAAAAAGTCCAGAGTAGTCGATACCCTGGGC |
| s6936 | 16 | AAAAAAGGATCCCTCTTGTTGTCGTTATAGAGA |
| s6937 | 17 | AAAAAACATATGAGCAAATACGAAGGCCG |
| s6938 | 18 | AAAAAAGAATTCGGTTCTGCACTCTTGTTGTT |
| s6939 | 19 | AAAAAAGGATCCTGGCCATTATCTGGCTCAG |
| s6946 | 20 | AAAAAATGTACACTGGTGAGCTACGACATCAA |
| s6965 | 21 | AAAAAACAATTGTCACTGCCCGCTTTCCAGT |
| s7343 | 22 | AAAAAAGGATCCACGGCAGGAAGCTGCTGG |
| s7344 | 23 | AAAAAAGAATTCTAGACCGCGTCGCCTTCTT |
| s7345 | 24 | AAAAAAGAATTCCATGGTGTGTCTCCTTGGTA |
| s7346 | 25 | AAAAAAGGATCCCGCGATACGTCGGGGCG |
| s7390 | 26 | AAAAAAGGATCCTTGACGTGCATCCGGTCAC |
| s7391 | 27 | AAAAAAGAATTCCATTCATTGCCGAATCGTTCT |
| s7392 | 28 | AAAAAAGAATTCCATCTGGACGATGGCCGTG |
| s7393 | 29 | AAAAAAGGATCCGCGCTACGCGAGGTGTTC |
| s7982 | 30 | AAAAAAGGATCCTTCCATGCTCAGGACCCTAT |
| s7983 | 31 | AAAAAACAATTGCATGCACTTTTGAT- |

TABLE 2a-continued

Oligonucleotide primers used in this invention

| Primer | SEQ ID NO: | Sequence (5' → 3')[a] |
|---|---|---|
| | | TAATCGATT |
| s7984 | 32 | AAAAAACAATTGTGATTCGGGTGCGAGCTGT |
| s7985 | 33 | AAAAAAGGATCCCGCCGGACAGCATGAGCA |

[a]Restriction sites are indicated in boldface Table 2b Amino acid and nucleotide sequences of genes and regulatory elements used for engineering experiments:

| SEQ ID NO: | Gene name P. putida genome | Short name/Description (NS/AS) |
|---|---|---|
| 34 | PP_0166-PP_0168 | lapABC; NS |
| 35 | PP_0166, incomplete | LapC; AS |
| 36 | PP_0167 | LapB; AS |
| 37 | PP_0168, incomplete | LapA; AS |
| 38 | PP_3357 | Vanillin dehydrogenase; NS |
| 39 | PP_3357 | Vanillin dehydrogenase; AS |
| 40 | PP_3827-3832 | including modABC; NS |
| 41 | PP_3828 | ModA; AS |
| 42 | PP_3829 | ModB; AS |
| 43 | PP_3830 | ModC; AS |
| 44 | PP_2680 | Aldehyde Dehydrogenase; NS |
| 45 | PP_2680 | Aldehyde Dehydrogenase; AS |
| 46 | PP_0545 | Aldehyde Dehydrogenase; NS |
| 47 | PP_0545 | Aldehyde Dehydrogenase; AS |
| 48 | PP_1948 | Benzaldehyde Dehydrogenase; NS |
| 49 | PP_1948 | Benzaldehyde Dehydrogenase; AS |
| 50 | | $P_{tac}$-lacI[a] (integrated between base pairs 3798896 and 3798897); NS |
| 51 | PP_3354-3355 | β-ketothiolase/acyl-CoA hydrolase; NS |
| 52 | PP_3354 | β-ketothiolase; AS |
| 53 | PP_3355 | acyl-CoA hydrolase, AS |

NS = nucleotide sequence

AS = amino acid sequence

Vector Construction and Genetic Manipulation of P. putida Strains

Cloning steps were performed with E. coli JM109 (Yanisch-Perron et al., 1985) using standard recombinant DNA techniques (Sambrook et al., 1989). Transformation of E. coli with plasmid DNA occurred via the TSS (Transformation and Storage Solution) method (Chung et al., 1989). P. putida strains were transformed with plasmid DNA via electroporation (Sambrook et al., 1989). Construction of the plasmids and strains is summarized in Table 3.

TABLE 3

Overview of the strain constructions

| Gene/region | PP_0166-PP_0168 (lapABC) | PP_3357 (vdh) | PP_3827-PP_3832 (modABC) | $P_{tac}$-lacI$^q$ | PP_3354 + PP_3355 | PP_2680 | PP_0545 | PP_1948 |
|---|---|---|---|---|---|---|---|---|
| Deletion/integration region (bp)$^a$ | 190765-219759 | 3796527-3797987 | 4352876-4358100 | between 3798896 and 3798897 | 3791583-3794516 | 3068912-3070390 | 631921-633435 | 2203324-2204796 |
| Primers upstream region | s6007/s6008 | s6534/s6535 | s6882/s6883 | s6937/s6936 | s7390/s7391 | s6927/s6928 | s7343/s7344 | s7982/s7983 |
| (fragment length) | (808 bp) | (936 bp) | (955 bp) | (897 bp) | (782 bp) | (950 bp) | (876 bp) | (823 bp) |
| Primers downstream region | s6009/s6010 | s6536/s6537 | s6884/s6885 | s6938/s6939 | s7392/s7393 | s6946/s6930 | s7345/s7346 | s7984/s7985 |
| (fragment length) | (791 bp) | (1053 bp) | (1072 bp) | (952 bp) | (923 bp) | (953 bp) | (820 bp) | (829 bp) |
| Cloned via | BamHI/HindIII | BamHI/EcoRI | BamHI/NcoI | BamHI/EcoRI/MfeI | BamHI/EcoRI | SalI/BsrGI | BamHI/EcoRI | BamHI/MfeI |
| Integration vector | pNG53.1 | pNG173.1 | pNG260.4 | pNG283.5 | pNG340.2 | pNG276.1 | pNG338.1 | pNG412.1 |
| P. putida target strain | ΔUPP4 | GN23 | GN235 | GN276 | GN299 | GN299 | GN440 | GN441 |
| Resulting strain | GN23 | GN235 | GN276 | GN299 | GN347 | GN440 | GN441 | GN442 |

$^a$bp numbers are derived from the sequenced P. putida KT2440 genome (GenBank accession number AE015451)

For chromosomal deletions and integrations in *P. putida* KT2440 the upp/5-FU counterselection system was used as described previously (Graf and Altenbuchner, 2011). First, the up- and downstream regions including the start and stop codons of the target gene were PCR amplified using chromosomal DNA of *P. putida* KT2440 (GenBank accession number AE015451) as template. These fragments were cloned via 3-fragment ligation into pJOE6261.2. The resulting integration vector was then used for electroporation of *P. putida* ΔUPP4 or other upp deleted strains. One of the Kan$^r$5-FU$^s$ clones obtained, was incubated in LB medium for 24 h at 30° C. under shaking conditions (200 rpm). Afterwards, different dilutions were plated on minimal plates containing 20 μg ml$^{-1}$ 5-FU and 0.2% glucose. Ten 5-FU$^r$ and Kan$^s$ clones were checked by colony PCR, using oligonucleotides binding to the up- and downstream sequences of the gene to be deleted.

Construction of the lacI$^q$-P$_{tac}$ integration vector pNG283.5 started with the PCR amplification of ech using oligonucleotide primers s6936/s6937 and chromosomal DNA of *P. putida* KT2440 as template. The purified PCR fragment (897 bps) was cloned via NdeI/BamHI into pJOE5304.1 resulting in pNG281.1, a vector with a lacI$^q$-P$_{tac}$-ech cassette. Next, this cassette was PCR amplified with s6936/s6965 (fragment A; 2376 bps). Also, the upstream region of ech was PCR amplified with s6938/s6939 (fragment B; 952 bps). Fragment A and B were cut with BamHI/MfeI and EcoRI/BamHI, respectively, and cloned via 3-fragment ligation into BamHI cut pJOE6261.2, giving pNG283.5.

Mating and Transposon Mutagenesis

Overnight cultures of *E. coli* S17.1/pCro2a (contains mini-Tn5495) (Onaca et al., 2007) and *P. putida* GN235 grown in LB with kanamycin and without kanamycin, respectively, were mixed equally (200 μl each) and 100 μl of that mixture was dropped onto a LB agar plate without antibiotics. After incubation for 24 h at 30° C. grown cells were scraped off the plate with 3 ml LB liquid medium. In each case 100 μl of a 10$^{-2}$ dilution (giving about 50-100 colonies) were plated on a total of 50 LB agar plates containing 50 μg ml$^{-1}$ kanamycin and μg ml$^{-1}$ μM nalidixic acid (for counterselection of the *E. coli* donor). The plates were then incubated for 40 h at 30° C. From each plate the colonies were replica plated on M9 minimal agar plates, one with 0.2% (w/v) glucose and the other one with 0.1% (w/v) vanillin. Incubation occurred overnight at 30° C. Colonies which were grown on M9 plates with glucose but not on M9 plates with vanillin were toothpicked on a LB agar plate with 50 μg ml$^{-1}$ kanamycin and μg ml$^{-1}$ nalidixic acid, on a M9 agar plate with 0.1% vanillin and on a M9 agar plate with 0.1% vanillic acid and incubated overnight at 30° C. The chromosomal DNA from clones which had grown on LB$_{kan/nal}$ and on M9 with vanillic acid but not on M9 with vanillin was isolated (DNeasy Blood and Tissue Kit, Qiagen, Hilden, Germany) and digested with restriction enzymes BsrGI, EcoRI and SalI, respectively. The chromosomal fragments were purified (NucleoSpin Extract II Kit, Macherey-Nagel, Düren, Germany), ligated overnight at 4° C., precipitated with isopropanol for 2 h on ice, washed with ethanol and resuspended in 10 μl H$_2$O (bidest.). *E. coli* JM109 was transformed with the ligated chromosomal fragments. Selection occurred on LB agar plates containing 50 μg ml$^{-1}$ kanamycin.

Plasmids were isolated from kanamycin resistant clones and checked by restriction enzyme digestion. After sequencing of the plasmids with primers s4052 and s4037 (Onaca et al., 2007) (GATC Biotech, Constance, Germany) the obtained sequences were finally subjected to a BLAST search.

Bioconversion Assay of Ferulic Acid to Vanillin

Overnight cultures of *P. putida* strains were diluted 1:50 in fresh LB medium and grown for 2 h at 30° C. in shaking flasks (200 rpm). Induction of the ferulic acid metabolic genes occurred by addition of 5 mM ferulic acid or 5 mM IPTG depending on the strain. After further growth for 6 h at 30° C. under shaking conditions 25×10$^9$ cells were harvested by centrifugation (10 min, 3,500 g, room temperature), washed and resuspended with 5 ml of 50 mM sodium phosphate buffer (pH 7.2). A total of 10 mM of ferulic acid (1 M stock solution in DMSO) was added to the cell suspension. The bioconversion was conducted in long glass culture tubes at 30° C. under shaking conditions (200 rpm). Samples of 200 μl were taken after 1, 2, 3, 4, 5 and 18 h conversion time. After a centrifugation step (10 min, 16,000 g, room temperature) to pellet the cells 100 μl of the supernatant was collected and stored at −70° C. until analysis through HPLC.

Analytical Methods

Samples from the bioconversion assay were diluted 1:10 with 0.2% acetic acid prior to HPLC application. Ferulic acid, vanillin, vanillic acid and vanillyl alcohol were quantified with a Merck-Hitachi HPLC system (Merck, Darmstadt, Germany) equipped with a RP Purospher®-Star RP-18e column (250 mm×4.6 mm, 5 µm), a LiChroCART® guard column (4 mm×4 mm, 5 µm), an L7612 degasser, an L6200A gradient pump, a D6000A interface module, an L4200 UV-visible detector, a Rheodyne injection valve 7125 with a 100-µl sample loop, and D7000 HPLC System Manager software. For measurements a modified procedure was used as described previously (Sinha et al., 2007): Methanol, acetonitrile and 0.2% acetic acid (3:3:14) were used as the mobile phase. The flow rate was 1 ml min$^{-1}$ and the absorbance was measured at 231 nm for 20 min. Solutions of ferulic acid, vanillin, vanillic acid and vanillyl alcohol with seven different concentrations (0.05, 0.1, 0.2, 0.3, 0.4, 0.5 and 1 mM) were used for calibration.

B. Experiments

Example 1

Construction and Characterization of a P. putida KT2440 Mutant Unable to Grow on Vanillin as Sole Carbon Source As reported previously (Overhage et al., 1999b; Plaggenborg et al., 2003), P. putida KT2440 is able to grow on ferulic acid as sole carbon source. Ferulic acid is metabolized in a few steps to vanillin, catalyzed by feruloyl-CoA-synthetase (PP_3356, fcs) and enoyl-CoA-hydratase/aldolase (PP_3358, ech). Vanillin in turn gets further degraded to vanillic acid by the vanillin dehydrogenase (PP_3357, vdh). The last step has to be prevented, if vanillin accumulation is desired. The chromosomal organization of these genes in P. putida KT2440 and other strains constructed in this invention is shown in FIG. 2.

With respect to industrial applications, we constructed P. putida strain GN23 with a deletion in the lapABC operon including the gene for the surface adhesion protein (PP_0168, lapA) using the previously described upp counterselection method (Graf and Altenbuchner, 2011). The surface adhesion protein is responsible and essential for the formation of biofilms as previously shown for another P. putida KT2440 ΔlapA mutant strain (Graf and Altenbuchner, 2011).

Figure 2:
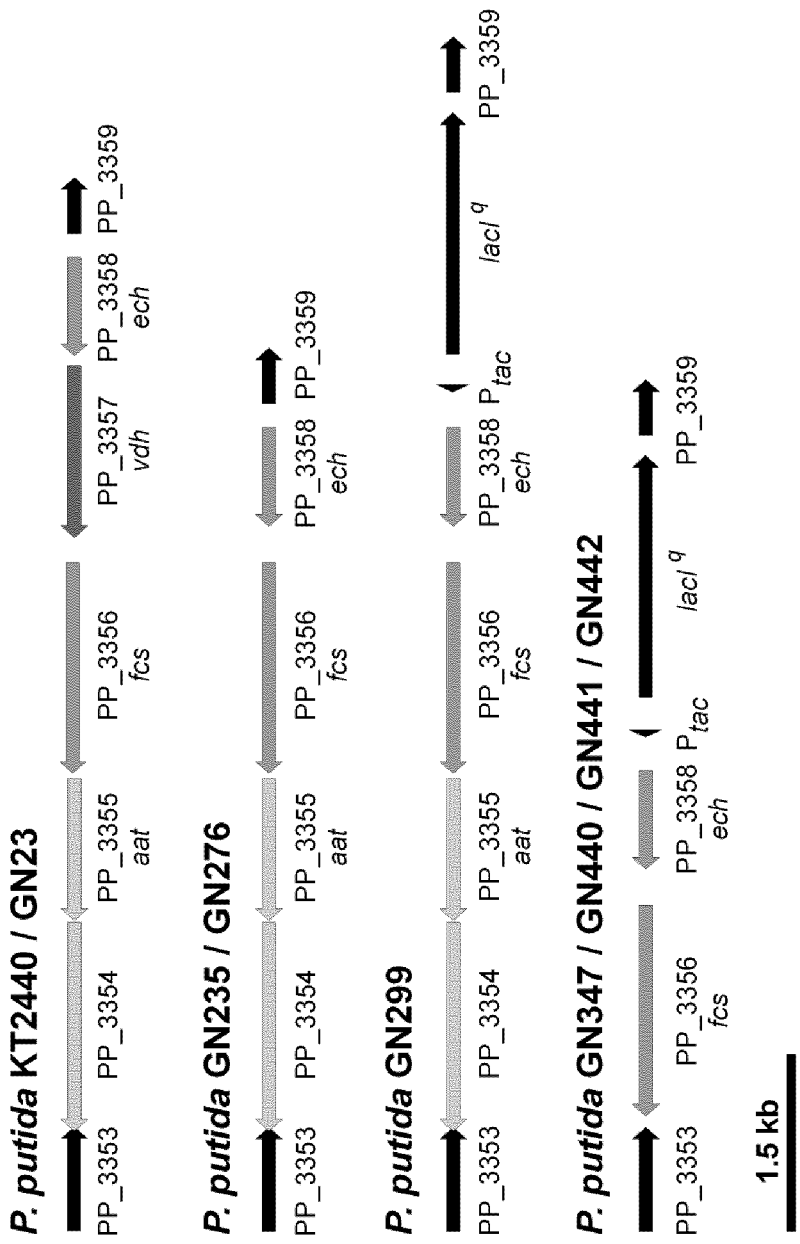
FIG. 2: Organization of the structural genes of the enoyl-CoA hydratase/aldolase (ech), feruloyl-CoA synthetase (fcs), and vanillin dehydrogenase (vdh), β-ketothiolase (aat) and acyl-CoA dehydrogenase (PP_3354) in the *P. putida* mutant strains used in this invention. The integration site of the tac promoter region including the lac operator ($P_{tac}$) and the gene for the lac repressor ($lacI_q$) is depicted.
Figure 3:
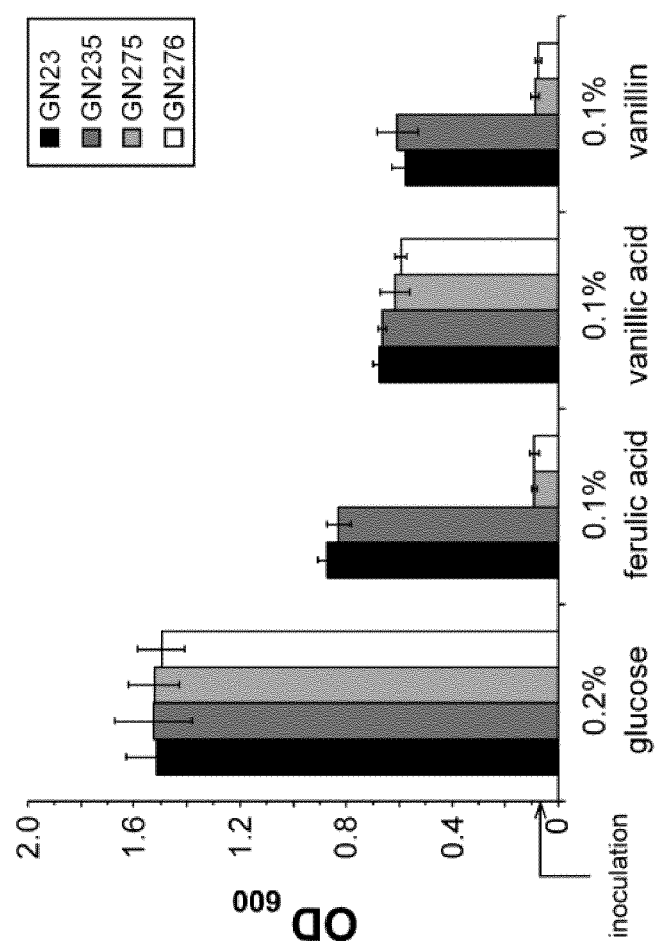
FIG. 3: Growth of *P. putida* mutant strains GN23, GN235, GN275 and GN276 in M9 minimal medium with different carbon sources. Strains were inoculated with 0.05 $OD_{600}$ as indicated by an arrow. Growth was documented by measuring the $OD_{600}$. The $OD_{600}$ after 24 h at 30° C. is presented to show the ability of the strains to grow on glucose, ferulic acid, vanillic acid and vanillin, respectively, as sole carbon source.

In a second step, the chromosomal vdh gene of P. putida GN23 was deleted leaving just the start and stop codon of vdh (FIG. 2). The resulting strain, designated as GN235, was still able to grow on ferulic acid as sole carbon source demonstrating functional expression of fcs. GN235 also retained the ability to grow on vanillin and vanillic acid (FIG. 3).

Using transposon mutagenesis of GN235, we found a mutant (GN275) which was unable to grow on ferulic acid or vanillin as sole carbon sources. However, growth on vanillic acid was retained (FIG. 3). Identification of the gene disrupted by the transposon revealed modA (PP_3828), which encodes a periplasmic molybdate-binding protein, which is part of a molybdate ABC transporter. The whole operon including modABC (PP_3827-PP_3832) was deleted markerlessly with the upp counterselection method resulting in strain GN276. The phenotype of this strain was the same as the transposon mutant (FIG. 3).

Example 2

Bioconversion Assays of Strains GN23, GN235 and GN276

Figure 4:
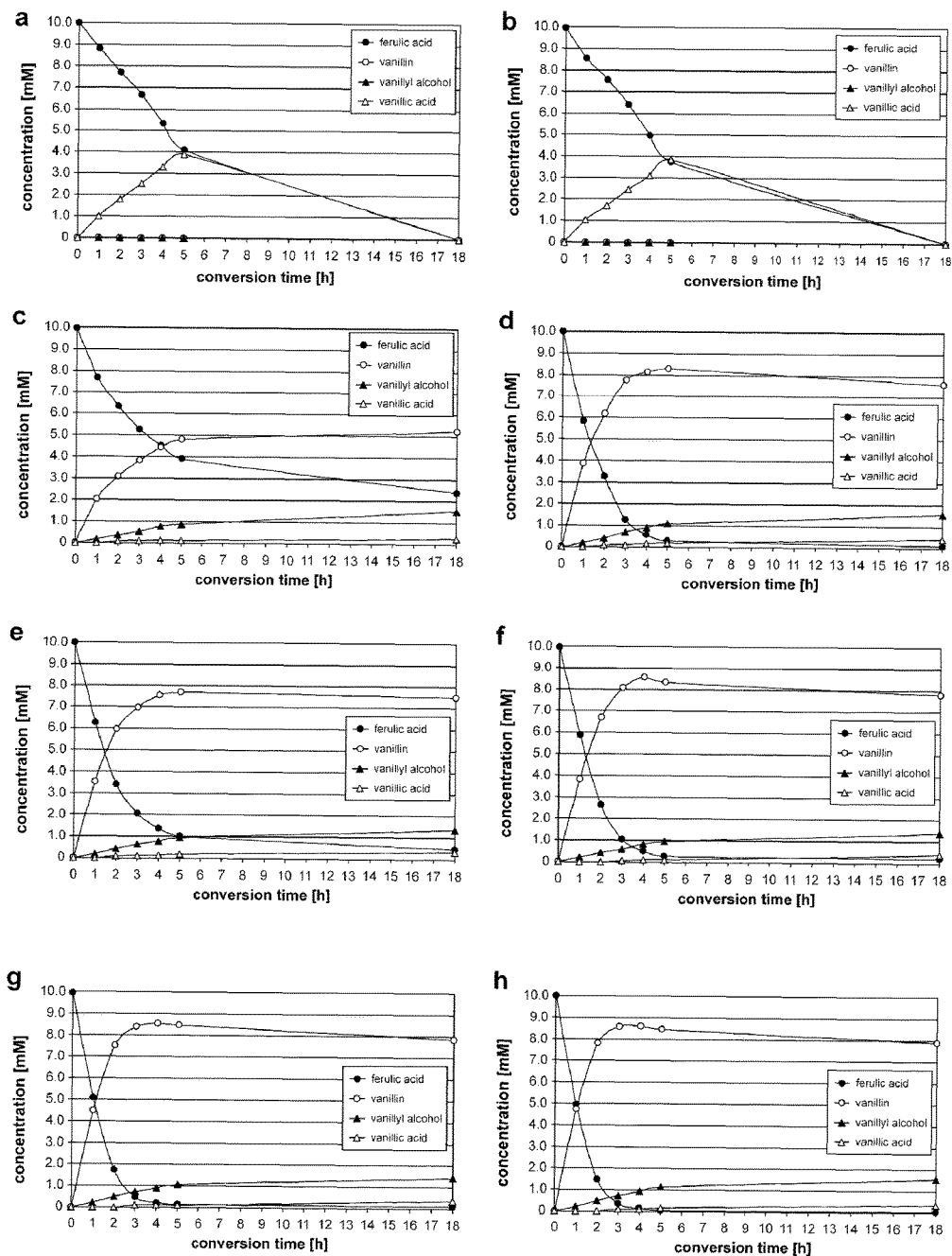
FIG. 4: Bioconversion assays of ferulic acid to vanillin. Metabolic genes ech and fcs were induced for 6 h with 5 mM IPTG before bioconversion of ferulic acid to vanillin was started with $5\times10^9$ resting cells $ml^{-1}$ of *P. putida* strains (a) GN23, (b) GN235, (c) GN276, (d) GN299, (e) GN347, (f) GN440, (g) GN441 and (h) GN442. Concentrations of ferulic acid (black circles), vanillin (white circles), vanillyl alcohol (black triangle) and vanillic acid (white triangle) were measured by HPLC and plotted over the conversion time. The figure shows the mean values of at least three independently repeated assays. The standard deviation was less than 10%.

Resting cells of strains GN23 and GN235 were used for bioconversion assays. 10 mM of ferulic acid were added to the resting cells and the concentrations of ferulic acid, vanillin, vanillyl alcohol and vanillic acid were measured by HPLC taking samples at regular intervals during reaction time. The assay was stopped after 18 h conversion time. Both strains, GN23 and GN235, showed a rapid conversion of ferulic acid accompanied with a temporary accumulation of vanillic acid in the first 5 h (FIG. 4a,b). Furthermore, accumulation of vanillin, vanillyl alcohol and vanillic acid could not be observed in either of them.

A bioconversion assay of ferulic acid with GN276 (FIG. 4c) showed a decreased conversion rate of ferulic acid. Whereas with GN23 all of the applied ferulic acid (10 mM) was converted after 18 h, 2.4 mM could still be measured using GN276. In contrast to GN23 and GN235, GN276 accumulated 4.8 mM vanillin after 5 h conversion time. Vanillin concentration slightly increased to 5.2 mM after further 13 h conversion. At the end of the conversion (18 h) also vanillyl alcohol and vanillic acids were accumulated up to 1.5 mM and 0.3 mM, respectively. To improve the ferulic acid conversion rate further steps were necessary.

Example 3

Increase of Chromosomal Ech-Fcs Expression Leads to High Conversion Rates and High Vanillin Molar Yields Feruloyl-CoA-synthetase (fcs) and enoyl-CoA-hydratase/aldolase (ech) catalyze the conversion of ferulic acid to vanillin. We assumed that the conversion rate of ferulic acid should be directly proportional to the number of these two metabolic enzymes in the cell, if the required cofactors, ATP and CoA-SH, are available in excess or regenerated. Using the upp counterselection system, the strong tac promoter ($P_{tac}$) and lacI$^q$ were integrated immediately upstream of ech and fcs in the chromosome of GN276 in order to control the expression of these two genes (FIG. 2).

The resulting strain was designated GN299. After induction of ech and fcs expression with IPTG, bioconversion assays were conducted with this strain. After 5 h, nearly all of the 10 mM ferulic acid were converted to 1.1 mM vanillyl alcohol, 0.2 mM vanillic acid and 8.3 mM of vanillin, corresponding to a molar yield of 83% (FIG. 4d). After 18 h conversion, the vanillin concentration slightly decreased to 7.6 mM accompanied with an increase of vanillyl alcohol and vanillic acid to 1.6 mM and 0.4 mM, respectively.

Example 4

Optimization of the Bioconversion Assay Revealed a Threshold for Vanillin

Resting cells of P. putida GN299 were used for bioconversion experiments. Several parameters were varied aiming a high and reproducible product yield combined with a high initial conversion rate.

Figure 5:
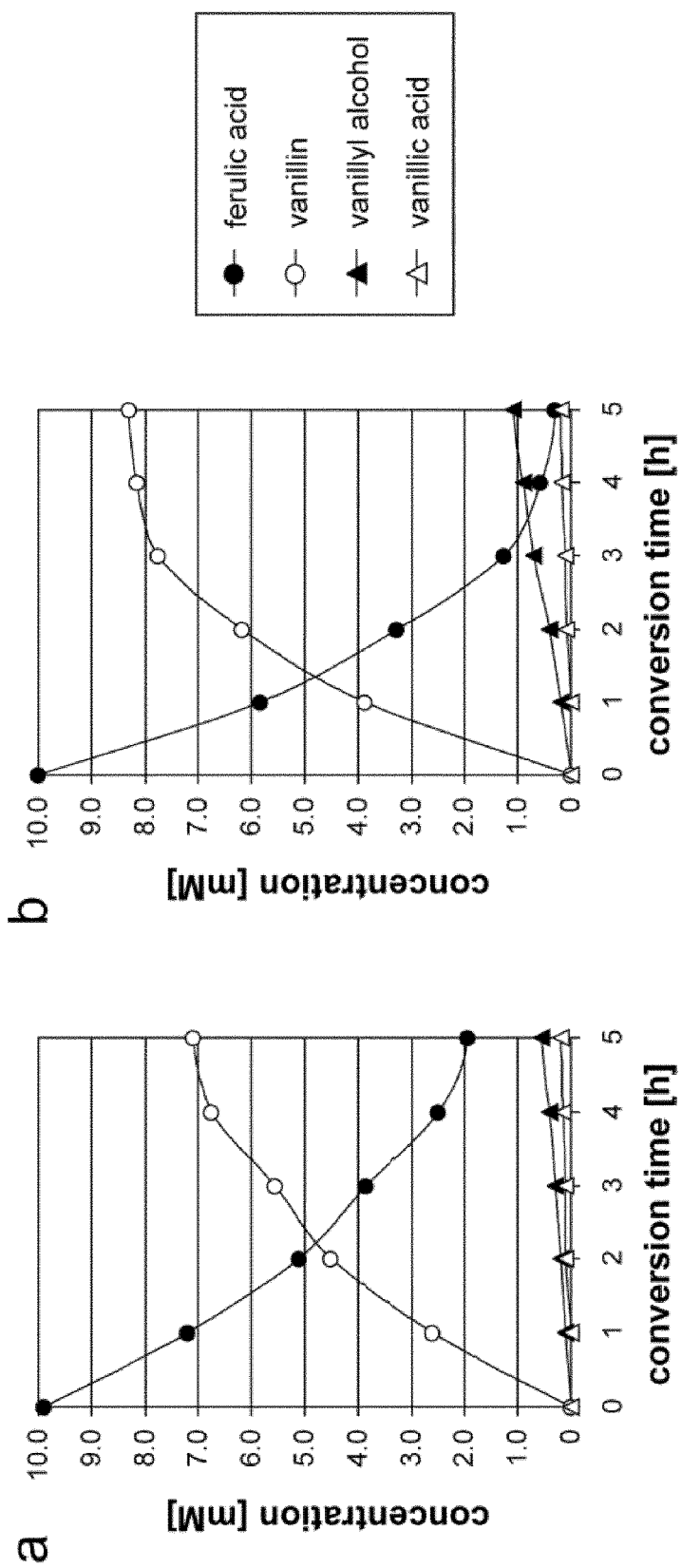
FIG. 5: Influence of the amount of inducer IPTG on the bioconversion of ferulic acid to vanillin. Cells of *P. putida* GN299 were induced for 6 h with (a) 1 mM IPGT and (b) 5 mM IPTG before bioconversion of ferulic acid to vanillin was started with $5\times10^9$ resting cells $ml^{-1}$. Concentrations of ferulic acid (black circles), vanillin (white circles), vanillyl alcohol (black triangle) and vanillic acid (white triangle) were measured by HPLC and plotted over the conversion time. The figure shows the mean values of at least three independently repeated assays. The standard deviation was less than 10%.

First, we analyzed the influence of the inducer concentration (1 and 5 mM IPTG) and of the induction time (2, 4, and 6 h) for the expression of the metabolic enzymes needed for the bioconversion of ferulic acid to vanillin (FIG. 5+6a). We found that conversion of ferulic acid was much slower using less than 5 mM IPTG (FIG. 5). However, the vanillin yields after 18 h conversion time were similar (not shown). Regarding the influence of the induction time (FIG. 6a), the highest conversion rates and vanillin yields were found after 6 h induction of the metabolic enzymes.

Figure 6:
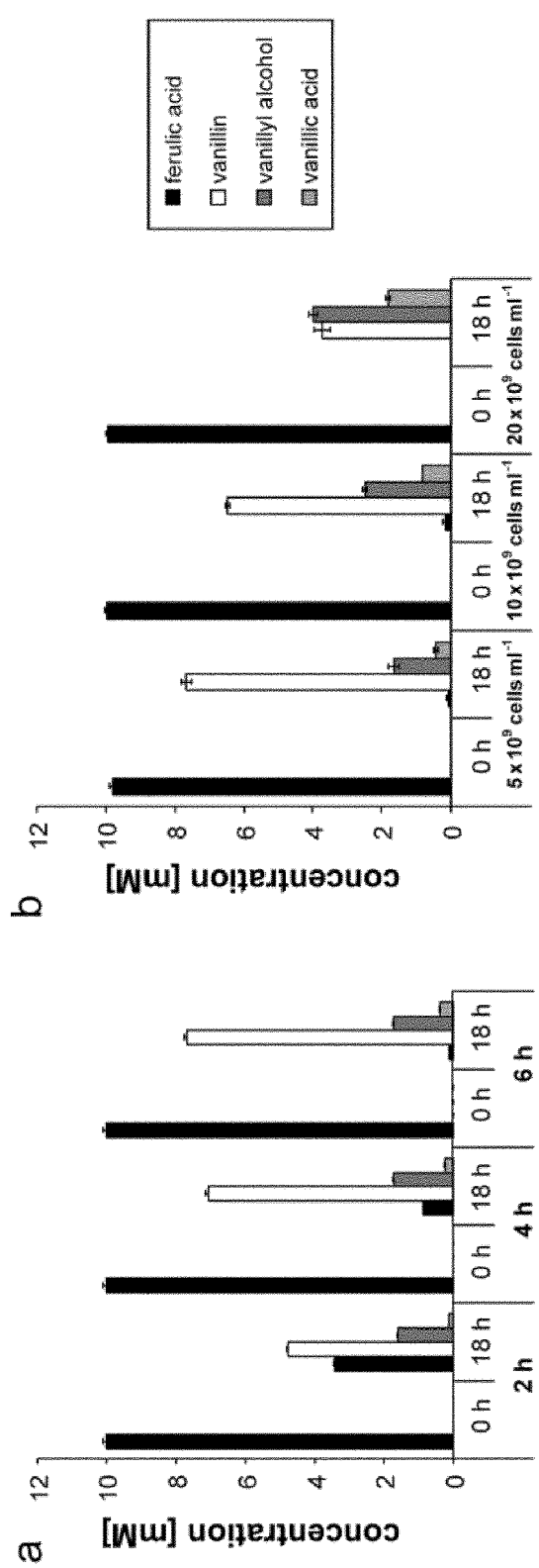
FIG. 6: Influence of the (a) induction time and (b) amount of resting cells of *P. putida* GN299 on the bioconversion of ferulic acid to vanillin. (a) Cells were induced for 2, 4, and 6 h with 5 mM IPTG before bioconversion of ferulic acid to vanillin was started with $5\times10^9$ resting cells $ml^{-1}$. (b) Cells were induced for 6 h with 5 mM IPTG before bioconversion of ferulic acid to vanillin was started with varying amounts of resting cells (5, 10, and $20\times10^9$ cells $ml^{-1}$). Concentrations of ferulic acid (black bars), vanillin (white bars), vanillyl alcohol (dark gray bars) and vanillic acid (light gray bars) were measured by HPLC and shown at the beginning (0 h) and at the end (18 h) of the bioconversion assay. The figure shows the mean values of at least three independently repeated assays. The standard deviation is represented by error bars.

Furthermore, the amount of resting cells was also varied (5, 10, and 20×10$^9$ cells ml$^{-1}$). The best results were aimed with the lowest concentration of 5×10$^9$ cells ml$^{-1}$ (FIG. 6b). Higher cell concentrations led to raised levels of vanillyl alcohol and vanillic acid accompanied with a decrease in the vanillin molar yield after prolonged conversion (18 h).

Figure 7:
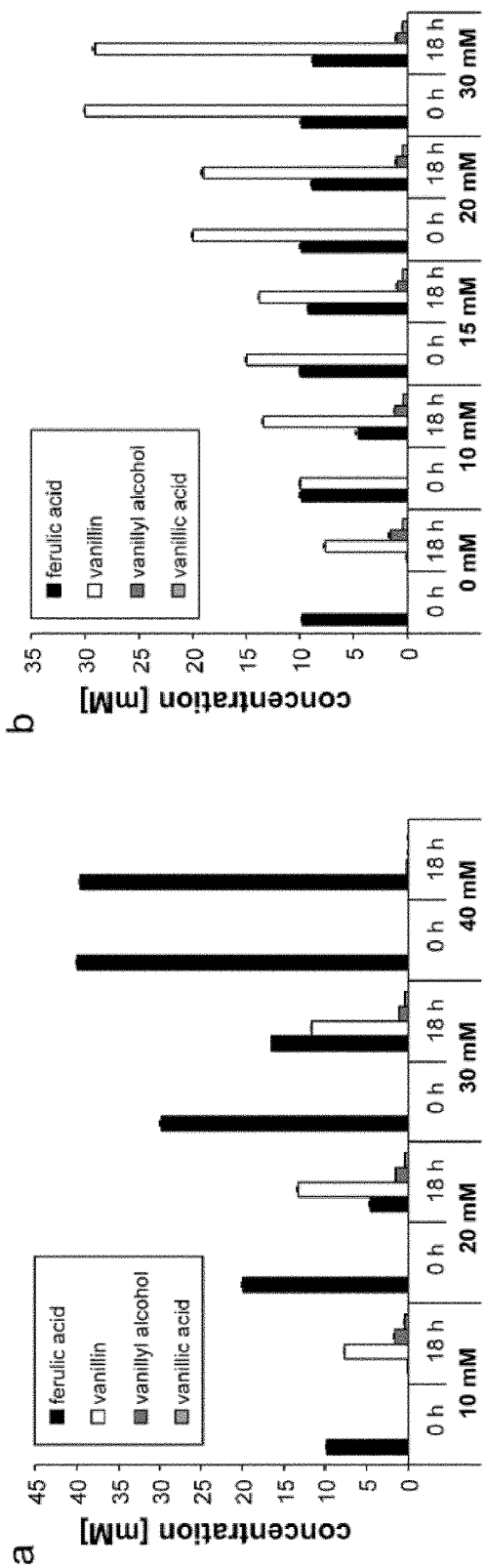
FIG. 7: Influence of (a) ferulic acid and (b) vanillin concentration on the bioconversion. Metabolic genes ech and fcs were induced for 6 h with 5 mM IPTG before bioconversion of ferulic acid to vanillin was started with $5\times10^9$ resting cells $ml^{-1}$ of *P. putida* GN299. (a) Increasing concentrations of ferulic acid (10, 20, 30, and 40 mM) were used for the conversion to vanillin. (b) Increasing concentrations of vanillin (0, 10, 15, 20, and 30 mM) were added at the beginning of the bioconversion assay with 10 mM ferulic acid. Concentrations of ferulic acid (black bars), vanillin (white bars), vanillyl alcohol (dark gray bars) and vanillic acid (light gray bars) were measured by HPLC and shown at the beginning (0 h) and at the end (18 h) of the bioconversion assay. The figure shows the mean values of at least three independent assays. The standard deviation is represented by error bars.
Figure 8:
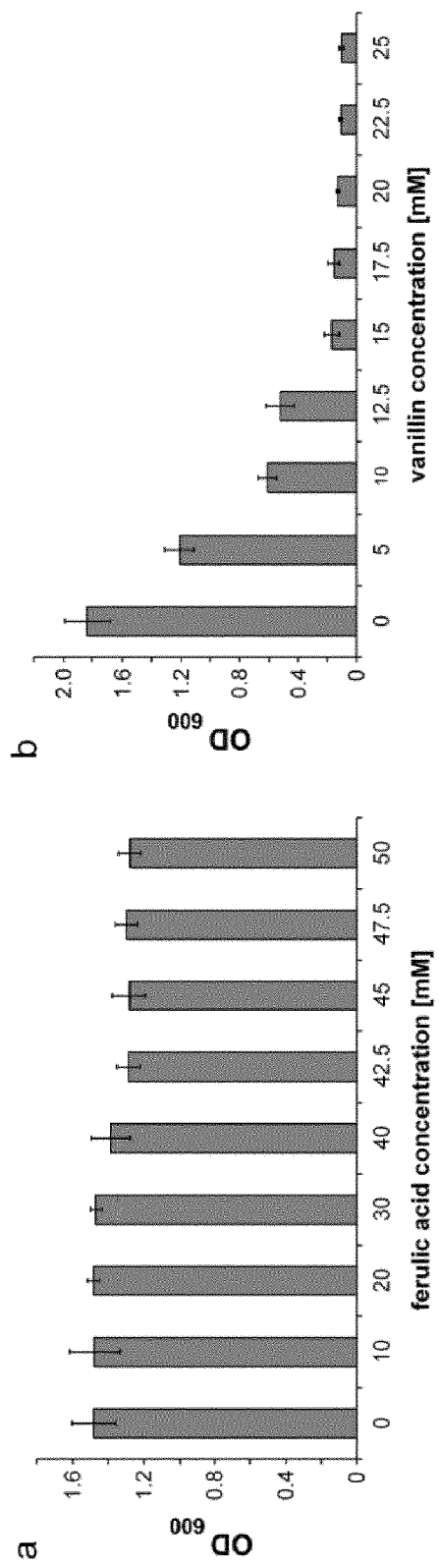
FIG. 8: Tolerance of *P. putida* mutant strain GN299 towards different (a) ferulic acid and (b) vanillin concentrations in M9 minimal medium. After inoculation with 0.1 $OD_{600}$ in M9 minimal medium with 0.4% glucose and increasing concentrations of (a) ferulic acid and (b) vanillin, growth was documented by measuring the $OD_{600}$. The $OD_{600}$ after 24 h at 30° C. is presented to show the tolerance of GN299 towards different concentrations of ferulic acid and vanillin, respectively. The figure shows the mean values of at least three independent assays. The standard deviation is represented by error bars.

In this invention, we found that there is a threshold for vanillin production. Induced and resting cells were incubated with increasing amounts of ferulic acid in the bioconversion broth (10, 20, 30, and 40 mM). Using up to 30 mM ferulic acid, strains did not produce more than 13.5 mM vanillin (FIG. 7a). With 40 mM ferulic acid, no vanillin was produced at all. The best yields were achieved using 10 mM ferulic acid for the bioconversion assay. Growth kinetics of *P. putida* KT2440 mutant strains in buffered M9 minimal medium (pH 7.0) with glucose and increasing amounts of ferulic acid (0-50 mM) showed no influence of the ferulic acid concentration (FIG. 8a).

The vanillin threshold effect was confirmed by incubation of resting cells with 10 mM ferulic acid and additional increasing amounts of vanillin (10, 15, 20 and 30 mM). The cells incubated with additional 10 mM vanillin produced only further 3.2 mM vanillin after 18 h (FIG. 7b). On the other hand, higher amounts of vanillin resulted in a slight decrease of vanillin concentration and an increase of vanillyl alcohol and vanillic acid concentrations. Growth kinetics of *P. putida* KT2440 mutant strains in M9 minimal medium with glucose and increasing amounts of vanillin (0-25 mM) showed significant influence of the vanillin concentration (FIG. 8b). With up to 12.5 mM vanillin the strains showed moderate growth. With over 15 mM vanillin, growth was strongly impaired.

Example 5

Deletion of Further Genes and Consequences on Vanillin Production and by-Product Formation The bioconversion assays conducted with GN299 showed formation of vanillyl alcohol and vanillic acid which inevitably reduce the product yield. Therefore, the effect of the inactivation of several genes potentially involved in the ferulic acid metabolism was analyzed. The genes chosen for this analytical approach were PP_3354 (β-ketothiolase) and PP_3355 (acyl-CoA dehydrogenase), PP_2680 and PP_0545 (aldehyde dehydrogenases), and PP_1948 (benzaldehyde dehydrogenase).

First, a second pathway from ferulic to vanillic acid (FIG. 1) proposed by (Overhage et al., 1999b) was interrupted in strain GN299 by combined deletion of PP_3354 and PP_3355 coding for an acyl-CoA dehydrogenase and a β-ketothiolase (aat) as depicted in FIG. 2. The resulting strain GN347 was used for bioconversion assays (FIG. 4e). After 5 h 9 mM ferulic acid were converted to 7.7 mM vanillin, 1 mM vanillyl alcohol and 0.2 mM vanillic acid. After 18 h further 0.5 mM ferulic acid were converted. The vanillin concentration decreased to 7.5 mM, whereas vanillyl alcohol and vanillic acid slightly increased to 1.4 mM and 0.3 mM, respectively. Compared to GN299 the conversion rate and vanillin yield within the first 5 h decreased.

Since deletion of vdh could not prevent degradation of vanillin to vanillic acid, other aldehyde dehydrogenases may catalyze this reaction. From a proteomics approach it could be shown that two aldehyde dehydrogenases (encoded by PP_2680 and PP_0545) and the benzaldehyde dehydrogenase (PP_1948) were upregulated in *P. putida* KT2440 growing on vanillin (Simon, Pfannstiel and Huber, unpublished raw data, manuscript in preparation). Sequential inactivation of PP_2680 and PP_0545 in GN299 by markerless deletion resulted in strains GN440 and GN441, respectively. The benzaldehyde dehydrogenase may also accept vanillin as a substrate, since it is a derivative of benzaldehyde. Therefore, the corresponding gene (PP_1948) was deleted in GN441, resulting in strain GN442. The mutant strains GN440, GN441 and GN442 were used in bioconversion assays (FIG. 4f-h). The strains showed very similar results. After 4 h about 9.5 mM ferulic acid were converted to 8.6 mM vanillin with resting cells of GN440 and GN441. The measured vanillyl alcohol and vanillic acid concentrations were about 0.8 mM and 0.1 mM, respectively. Strain GN442 showed the same results, however, already after 3 h conversion. After 18 h conversion, nearly all of the ferulic acid was converted with all three strains. Again, vanillin concentration decreased to 7.9 mM, whereas vanillyl alcohol and vanillic acid increased to about 1.5 mM and 0.4 mM, respectively.

B. Discussion of Experiments

In contrast to *P. fluorescens* strains AN103 and BF13 (Martinez-Cuesta et al., 2005; Di Gioia et al., 2010), our findings with *P. putida* GN235 confirm that simple inactivation of vdh is not sufficient to prevent vanillin degradation. This was reported previously with a vdh knockout mutant of *Pseudomonas* sp. HR199 strain and a *Pseudomonas* KT2440vdhΩKm mutant (Overhage et al., 1999a; Plaggenborg et al., 2003). KT2440vdhΩKm and GN235 were still able to grow on vanillin as sole carbon source. The main difference, however, was that *P. putida* GN235 was also able to grow on ferulic acid, due to a functional expression of the adjacent genes of vdh, namely ech and fcs. The clean deletion of vdh sustained expression of ech and fcs, which was most probably not the case in the KT2440vdhΩKm mutant. A random transposon mutagenesis conducted with GN235 revealed a mutant with a transposon in the gene locus of modA, which encodes for a periplasmic molybdate-binding protein. Molybdate ions are known to play a role as cofactors in oxidoreductases in *Pseudomonas* species (Koenig and Andreesen, 1990; Blaschke et al., 1991; Frunzke et al., 1993). Since the ΔmodABC strain GN276 was not able to grow on vanillin as sole carbon source, it can be assumed that unknown molybdate depending oxidoreductases may accept vanillin as a substrate complementing the vdh inactivation. The inhibition of the molybdate uptake could inactivate these enzymes and vanillin is not oxidized to vanillic acid, which is further degraded. Since ferulic acid was not completely converted with GN276, further improvements were necessary.

A concurrent expression of the structural genes ech and fcs on a low-copy plasmid in a vdh negative *P. fluorescens* strain led to a vanillin molar yield of 63% within 5 h using resting cells from shaken flask experiments and up to 84% within 24 h using resting cells from a stirred tank reactor (Di Gioia et al., 2010). To circumvent possible problems of plasmid instabilities and usage of antibiotics, the strong tac promoter was introduced into the chromosome of *P. putida* GN276 to control expression of ech and fcs (GN299). This improved the vanillin molar yield up to 83% within just 5 h. We assume that raising the expression rate of ech and fcs through induction with IPTG led to higher concentrations of the encoded metabolic enzymes than using the original promoter system. In contrast to ferulic acid, the inducer IPTG gets not metabolized and the expression rates can stay on a high level. Lowering the amount of inducer led to a decrease in product yield and productivity, which can be explained by lower enzyme concentrations. We also checked the effect of induction time, showing that less than 6 h resulted in lower product yields, probably due to lower enzyme levels. Longer induction times were also checked, but did not improve the product yields (data not shown). Raising the cell concentration in the assay led to higher levels of the by-products vanillic acid and vanillyl alcohol and did not accelerate the conversion time. We assume that higher cell densitites are accompanied with higher levels of reduction equivalents which in turn may favor the formation of vanillyl alcohol.

Further improvements of the conversion process showed that raising the concentration of ferulic acid in the bioconversion broth results in a reduction of the vanillin molar yield, if higher concentrations than 10 mM of ferulic acid are used. A ferulic acid concentration of 40 mM even inhibited any conversion to vanillin. A toxic effect of ferulic acid, however, could be excluded, as growth experiments with increasing amounts of ferulic acid with up to 50 mM have shown.

On the other hand, P. putida GN299 showed a vanillin threshold of about 13.5 mM in the bioconversion assays. Raising the vanillin concentration above this threshold led to formation of more vanillyl alcohol and vanillic acid and inhibited conversion of ferulic acid. Such a product inhibition was also observed with recombinant E. coli strains converting ferulic acid to vanillin (Overhage et al., 2003). The toxic character of vanillin was confirmed with growth experiments of P. putida GN299 in the presence of increasing vanillin concentrations, where only up to 12.5 mM vanillin were tolerated. In contrast to P. fluorescens BF13, however, which showed a 98% reduction of the molar yield by increasing the ferulic acid concentration from 5 mM to 12.5 mM (Di Gioia et al., 2010), P. putida did not show such sensible reductions. Indeed, resting cells of P. putida GN442 could be reused after conversion for 18 h. Distracting vanillin by resuspending cells in new buffer with 10 mM ferulic acid and further incubation at 30° C. for 18 h resulted in production of 5 mM vanillin (4.5 mM ferulic acid, 0.5 mM vanillyl alcohol, 0 mM vanillic acid). Therefore, immediate distraction of the toxic product vanillin by adsorbent resins would allow P. putida cells to convert more ferulic acid as it could be shown previously for other systems (Yoon et al., 2007; Hua et al., 2007; Lee et al., 2009).

Inactivation of the alternative pathway from ferulic to vanillic acid proposed by Overhage et al. (1999b) by deletion of PP_3355 (aat) and PP_3354 in GN299 had no positive effect on formation of the unwanted formation of the by-products vanillyl alcohol and vanillic acid. It was observed that the conversion rate even decreased. A possible explanation for this behaviour could be a shorter half-life of the mRNA provoked by the deletion of the two genes and therefore a diminished level of the metabolic enzymes. However, inactivation of the up-regulated aldehyde dehydrogenases, encoded by PP_2680 and PP_0545, and the benzaldehyde dehydrogenase (PP_1948) in GN299 led to higher initial conversion rates and high molar yields. The results with this strain (GN442) represent the highest productivity of a Pseudomonas strain in bioconversion of ferulic acid to vanillin found in the literature so far. However, the deletions had no significant effect on formation of the by-products compared to GN299. In stirred tank reactor experiments it could previously be shown that raising the dissolved oxygen concentrations did not result in formation of more vanillic acid excluding a chemical oxidation process (Di Gioia et al., 2010). It was proposed that other broad substrate specificity dehydrogenases may act in Pseudomonas strains that have to be determined yet (Overhage et al., 1999b).

All our bioconversion experiments showed that prolonged bioconversion times up to 18 h reduced the vanillin molar yield due to formation of the by-products. Therefore, a fast and complete as possible conversion of ferulic acid to vanillin is desirable in the first few hours. The reduction of vanillin to vanillyl alcohol seems to represent a detoxification mechanism like it was also observed with recombinant E. coli cells converting ferulic acid to vanillin (Overhage et al., 2003). Another approach to reduce the formation of vanillyl alcohol was to lower the amount of $NADH_2$ by deletion of the genes PP_4011 and PP_4012, encoding the isocitrate dehydrogenase, like it was proposed for recombinant E. coli (Lee et al., 2009).

The surprisingly improved (fast and almost complete) conversion of ferulic acid as observed according to the present invention if compared to the results of (Di Gioia et al., 2010) is illustrated by the productivity data summarized in the subsequent Table 4:

TABLE 4

Comparison of productivities

| | Di Gioia (shaking flask) | Di Gioia (3L-Bio reactor) | GN442 (Invention) |
|---|---|---|---|
| Specific Produktivity [g(Vanillin)/(g(cell wet weight) · h)] | 0.01 | 0.02 | 0.09 |
| Volumetric Produktivity [g(Vanillin)/(L · h)] | 0.04 | 0.05 | 0.44 |

REFERENCE LIST

Achterholt S, Priefert H, Steinbüchel A (2000) Identification of Amycolatopsis sp. strain HR167 genes, involved in the bioconversion of ferulic acid to vanillin. Appl Microbiol Biotechnol 54:799-807

Altenbuchner J, Viell P, Pelletier I (1992) Positive selection vectors based on palindromic DNA sequences. Methods Enzymol 216:457-466

Barghini P, Di G D, Fava F, Ruzzi M (2007) Vanillin production using metabolically engineered Escherichia coli under non-growing conditions. Microb Cell Fact 6:13

Berger R G (2009) Biotechnology of flavours—the next generation. Biotechnol Lett 31:1651-1659

Bertani G (1951) Studies on lysogenesis. I. The mode of phage liberation by lysogenic Escherichia coli. J Bacteriol 62:293-300

Blaschke M, Kretzer A, Schafer C, Nagel M, Andreesen J R (1991) Molybdenum-dependent degradation of quinoline by Pseudomonas putida Chin IK and other aerobic bacteria. Arch Microbiol 155:164-169

Bonnin E, Lesage-Meessen L, Asther M, Thibault J F (1999) Enhanced bioconversion of vanillic acid into vanillin by the use of "natural" cellobiose. J Sci Food Agric 79:484-486

Calisti C, Ficca A G, Barghini P, Ruzzi M (2008) Regulation of ferulic catabolic genes in Pseudomonas fluorescens BF13: involvement of a MarR family regulator. Appl Microbiol Biotechnol 80:475-483

Chung C T, Niemela S L, Miller R H (1989) One-step preparation of competent Escherichia coli: transformation and storage of bacterial cells in the same solution. Proc Natl Acad Sci USA 86:2172-2175

Civolani C, Barghini P, Roncetti A R, Ruzzi M, Schiesser A (2000) Bioconversion of ferulic acid into vanillic acid by means of a vanillate-negative mutant of *Pseudomonas fluorescens* strain BF13. Appl Environ Microbiol 66:2311-2317

Clarke P H (1982) The metabolic versatility of pseudomonads. Antonie van Leeuwenhoek 48:105-130

Davidonis G, Knorr D (1991) Callus formation and shoot regeneration in *vanilla planifolia*. Food Biotechnol 5:59-66

Di Gioia D, Luziatelli F, Negroni A, Ficca A G, Fava F, Ruzzi M (2010) Metabolic engineering of *Pseudomonas fluorescens* for the production of vanillin from ferulic acid. J Biotechnol 156:309-316

Escott-Watson P L, Marais J P (1992) Determination of alkali-soluble phenolic monomers in grasses after separation by thin-layer chromatography. J Chromatgr 604: 290-293

Fleige C, Hansen G, Kroll J, Steinbüchel A (2013) Investigation of the *Amycolatopsis* sp. Strain ATCC 39116 vanillin dehydrogenase and its impact on the biotechnical production of vanillin. Appl Environ Microbiol 79:81-90

Frunzke K, Heiss B, Meyer O, Zumft W G (1993) Molybdopterin guanine dinucleotide is the organic moiety of the molybdenum cofactor in respiratory nitrate reductase from *Pseudomonas stutzeri*. FEMS Microbiol Lett 113: 241-245

Gasson M J, Kitamura Y, McLauchlan W R, Narbad A, Parr A J, Parsons E L, Payne J, Rhodes M J, Walton N J (1998) Metabolism of ferulic acid to vanillin. A bacterial gene of the enoyl-SCoA hydratase/isomerase superfamily encodes an enzyme for the hydration and cleavage of a hydroxycinnamic acid SCoA thioester. J Biol Chem 273: 4163-4170

Graf N, Altenbuchner J (2011) Development of a method for markerless gene deletion in *Pseudomonas putida*. Appl Environ Microbiol 77:5549-5552

Hansen E H, Moller B L, Kock G R, Bunner C M, Kristensen C, Jensen O R, Okkels F T, Olsen C E, Motawia M S, Hansen J (2009) De novo biosynthesis of vanillin in fission yeast (*Schizosaccharomyces pombe*) and baker's yeast (*Saccharomyces cerevisiae*). Appl Environ Microbiol 75:2765-2774

Havkin-Frenkel D, Belanger F C (2008). Biotechnological Production of Vanillin. In: Havkin-Frenkel D, Belanger F C (ed) Biotechnology in Flavor Production, 1st edn. Blackwell, Oxford, pp 83-103

Hua D, Ma C, Song L, Lin S, Zhang Z, Deng Z, Xu P (2007) Enhanced vanillin production from ferulic acid using adsorbent resin. Appl Microbiol Biotechnol 74:783-790

Ishii T (1997) Structure and functions of feruloylated polysaccharides. Plant Sci 127:111-127

Ishikawa H, Schubert W J, Nord F F (1963) Investigations on lignins and lignification. 28. The degradation by *Polyporus versicolor* and Fomes fomentarius of aromatic compounds structurally related to softwood lignin. Arch Biochem Biophys 100:140-149

Koenig K, Andreesen J R (1990) Xanthine dehydrogenase and 2-furoyl-coenzyme A dehydrogenase from *Pseudomonas putida* Ful: two molybdenum-containing dehydrogenases of novel structural composition. J Bacteriol 172:5999-6009

Kojima Y, Fujisawa H, Nakazawa A, Nakazawa T, Kanetsuna F, Taniuchi H, Nozaki M, Hayaishi O (1967) Studies on pyrocatechase. I. Purification and spectral properties. J Biol Chem 242:3270-3278

Krings U, Berger R G (1998) Biotechnological production of flavours and fragrances. Appl Microbiol Biotechnol 49:1-8

Lee E G, Yoon S H, Das A, Lee S H, Li C, Kim J Y, Choi M S, Oh D K, Kim S W (2009) Directing vanillin production from ferulic acid by increased acetyl-CoA consumption in recombinant *Escherichia coli*. Biotechnol Bioeng 102:200-208

Lesage-Meessen L, Delattre M, Haon M, Thibault J F, Ceccaldi B C, Brunerie P, Asther M (1996) A two-step bioconversion process for vanillin production from ferulic acid combining *Aspergillus niger* and *Pycnoporus cinnabarinus*. J Biotechnol 50:107-113

Martinez-Cuesta M C, Payne J, Hanniffy S B, Gasson M J, Narbad A (2005) Functional analysis of the vanillin pathway in a vdh-negative mutant strain of *Pseudomonas fluorescens* AN103. Enzym Microb Technol 37:131-138

Muheim A, Lerch K (1999) Towards a high-yield bioconversion of ferulic acid to vanillin. Appl Microbiol Biotechnol 51:456-461

Nakazawa T (2002) Travels of a *Pseudomonas*, from Japan around the world. Environ Microbiol 4:782-786

Narbad A, Gasson M J (1998) Metabolism of ferulic acid via vanillin using a novel CoA-dependent pathway in a newly-isolated strain of *Pseudomonas fluorescens*. Microbiol 144:1397-1405

Nelson K E, Weinel C, Paulsen I T, Dodson R J, Hilbert H, Martins d S, V, Fouts D E, Gill S R, Pop M, Holmes M, Brinkac L, Beanan M, DeBoy R T, Daugherty S, Kolonay J, Madupu R, Nelson W, White O, Peterson J, Khouri H, Hance I, Chris L P, Holtzapple E, Scanlan D, Tran K, Moazzez A, Utterback T, Rizzo M, Lee K, Kosack D, Moestl D, Wedler H, Lauber J, Stjepandic D, Hoheisel J, Straetz M, Heim S, Kiewitz C, Eisen J A, Timmis K N, Dusterhoft A, Tummler B, Fraser C M (2002) Complete genome sequence and comparative analysis of the metabolically versatile *Pseudomonas putida* KT2440. Environ Microbiol 4:799-808

Oddou J, Stentelaire C, Lesage-Meessen L, Asther M, Colonna Ceccaldi B (1999) Improvement of ferulic acid bioconversion into vanillin by use of high-density cultures of *Pycnoporus cinnabarinus*. Appl Microbiol Biotechnol 53:1-6

Okeke B C, Venturi V (1999) Construction of recombinants *Pseudomonas putida* B014 and *Escherichia coli* QEFCA8 for ferulic acid biotransformation to vanillin. J Biosci Bioeng 88:103-106

Onaca C, Kieninger M, Engesser K H, Altenbuchner J (2007) Degradation of alkyl methyl ketones by *Pseudomonas veronii* MEK700. J Bacteriol 189:3759-3767

Oosterveld A, Beldman G, Schols H A, Voragen A G (2000) Characterization of arabinose and ferulic acid rich pectic polysaccharides and hemicelluloses from sugar beet pulp. Carbohyd Res 328:185-197

Overhage J, Priefert H, Rabenhorst J, Steinbüchel A (1999a) Biotransformation of eugenol to vanillin by a mutant of *Pseudomonas* sp. strain HR199 constructed by disruption of the vanillin dehydrogenase (vdh) gene. Appl Microbiol Biotechnol 52:820-828

Overhage J, Priefert H, Rabenhorst J, Steinbüchel A (2000) Construction of production strains for producing substituted phenols by specifically inactivating genes of the eugenol and ferulic acid catabolism. Patent application WO 0026355

Overhage J, Priefert H, Steinbüchel A (1999b) Biochemical and genetic analyses of ferulic acid catabolism in *Pseudomonas* sp. Strain HR199. Appl Environ Microbiol 65:4837-4847

Overhage J, Steinbüchel A, Priefert H (2003) Highly efficient biotransformation of eugenol to ferulic acid and further conversion to vanillin in recombinant strains of *Escherichia coli*. Appl Environ Microbiol 69:6569-6576

Peng X, Misawa N, Harayama S (2003) Isolation and characterization of thermophilic bacilli degrading cinnamic, 4-coumaric, and ferulic acids. Appl Environ Microbiol 69:1417-1427

Plaggenborg R, Overhage J, Loos A, Archer J A, Lessard P, Sinskey A J, Steinbüchel A, Priefert H (2006) Potential of *Rhodococcus* strains for biotechnological vanillin production from ferulic acid and eugenol. Appl Microbiol Biotechnol 72:745-755

Plaggenborg R, Overhage J, Steinbüchel A, Priefert H (2003) Functional analyses of genes involved in the metabolism of ferulic acid in *Pseudomonas putida* KT2440. Appl Microbiol Biotechnol 61:528-535

Priefert H, Rabenhorst J, Steinbüchel A (2001) Biotechnological production of vanillin. Appl Microbiol Biotechnol 56:296-314

Ramachandra Rao S, Ravishankar G A (2000) *Vanilla* flavour: production by conventional and biotechnological routes. J Sci Food Agric 80:289-304

Rosazza J P, Huang Z, Dostal L, Volm T, Rousseau B (1995) Review: biocatalytic transformations of ferulic acid: an abundant aromatic natural product. J Ind Microbiol 15:457-471

Sambrook J, Fritsch E F, Maniatis T (1989) Molecular cloning: a laboratory manual, 2nd edn. Cold Spring Harbor Laboratory, Cold Spring Harbor, N.Y.

Simon R, Priefer U, Pühler A (1983) A broad host range mobilization system for in vivo genetic engineering: transposon mutagenesis in gram negative bacteria. Nat Biotech 1:784-791

Sinha A K, Verma S C, Sharma U K (2007) Development and validation of an RP-HPLC method for quantitative determination of vanillin and related phenolic compounds in *Vanilla planifolia*. J Sep Sci 30:15-20

Stentelaire C, Lesage-Meessen L, Delattre M, Haon M, Sigoillot J C, Ceccaldi B C, Asther M (1997) By-passing of unwanted vanillyl alcohol formation using selective adsorbents to improve vanillin production with *Phanerochaete chrysosporium*. World J Microbiol Biotechnol 14:285-287

Tilay A, Bule M, Annapure U (2010) Production of biovanillin by one-step biotransformation using fungus *Pycnoporous cinnabarinus*. J Agric Food Chem 58:4401-4405

Williams P A, Murray K (1974) Metabolism of benzoate and the methylbenzoates by *Pseudomonas putida* (*arvilla*) mt-2: evidence for the existence of a TOL plasmid. J Bacteriol 120:416-423

Yanisch-Perron C, Vieira J, Messing J (1985) Improved M13 phage cloning vectors and host strains: nucleotide sequences of the M13mp18 and pUC19 vectors. Gene 33:103-119

Yoon S H, Lee E G, Das A, Lee S H, Li C, Ryu H K, Choi M S, Seo W T, Kim S W (2007) Enhanced vanillin production from recombinant *E. coli* using NTG mutagenesis and adsorbent resin. Biotechnol Prog 23:1143-1148

Narang, S. A. (1983) Tetrahedron 39:3;

Itakura et al. (1984) (a) Annu. Rev. Biochem. 53:323;

Itakura et al., (1984) (b) Science 198:1056;

Ike et al. (1983) Nucleic Acids Res. 11:477

Arkin and Yourvan (1992) PNAS 89:7811-7815;

Delgrave et al. (1993) Protein Engineering 6(3):327-331

Higgins D G, Sharp P M. Fast and sensitive multiple sequence alignments on a microcomputer. Comput Appl. Biosci. (1989) April; 5(2):151-1

Chenna, Ramu, et al (2003) Nucleic Acids Res 31 (13): 3497-500, Ausubel et al. (eds), 1985, Current Protocols in Molecular Biology, John Wiley & Sons, New York;

Hames and Higgins (eds), 1985, Nucleic Acids Hybridization: A Practical Approach, IRL Press at Oxford University Press, Oxford;

Brown (ed), 1991, Essential Molecular Biology: A Practical Approach, IRL Press at Oxford University Press, Oxford Goeddel, Gene Expression Technology: Methods in Enzymology 185, Academic Press, San Diego, Calif. (1990)

Cloning Vectors (Eds. Pouwels P. H. et al. Elsevier), Amsterdam-New York-Oxford, 1985, ISBN 0 444 904018)

T. J. Silhavy, et al. Experiments with Gene Fusions, Cold Spring Harbor Laboratory, Cold Spring Harbor, N.Y. (1984)

Pearson and Lipman, Proc. Natl. Acad, Sci. (USA) 85(8), 1988, 2444-2448.

Applied Microbiol. Physiology, "A Practical Approach" (Publ. P. M. Rhodes, P. F. Stanbury, IRL Press (1997) p. 53-73, ISBN 0 19 963577 3).

Documents referred to herein are incorporated by reference.

The invention claimed is:

1. A biocatalytic process for producing vanillin from ferulic acid, comprising:
   a) culturing a genetically engineered bacterial strain of the genus *Pseudomonas* having the ability to convert ferulic acid to vanillin in the presence of ferulic acid; and
   b) optionally isolating vanillin thereby formed from the culture medium;
   wherein said genetically engineered bacterial strain has a reduced ability to grow on vanillin as the sole carbon source; and
   wherein said genetically engineered bacterial strain contains at least the following genetic modification:
   i) down-regulation of cellular molybdate uptake by down-regulating a gene encoding a periplasmatic molybdate binding protein (modA); and
   ii) down-regulation of the enzyme activity encoded by the vanillin dehydrogenase gene (vdh).

2. The process of claim 1, wherein down-regulating a gene encoding a periplasmatic molybdate binding protein (modA) is by deletion of a nucleotide sequence comprising the operon modABC.

3. The process of claim 1, wherein at least one of the enzyme activities encoded by the genes for
   iii) feruloyl-CoA synthetase (fcs) and
   iv) enoyl-CoA hydratase (ech)
   is up-regulated.

4. The process of claim 3, wherein chromosomal expression of the genes for feruloyl-CoA synthetase (fcs) and enoyl-CoA hydratase (ech) is upregulated.

5. The process of claim 4, wherein expression of the genes for feruloyl-CoA synthetase (fcs) and enoyl-CoA hydratase (ech) is under the control of a regulatory element comprising a strong promoter.

6. The process of claim 1, wherein additionally at least one of the following enzyme activities encoded by the genes
   v) aldehyde dehydrogenase PP_2680 and/or PP_0545 and
   vi) benzaldehyde dehydrogenase PP_1948
   is down-regulated.

7. The process of claim 1, wherein additionally at least one of the following enzyme activities encoded by the genes
   vii) beta-ketothiolase PP_3355 (aat) and
   viii) acyl-CoA dehydrogenase PP_3354
   is down-regulated.

8. The process of claim 1, wherein the *Pseudomonas* strain is a strain of *Pseudomonas putida*.

9. The process of claim 8, wherein said strain of *Pseudomonas putida* is genetically engineered by down-regulating a protein activity encoded by the gene for the surface adhesion protein (lapA).

10. The process of claim 1, which is carried out aerobically and/or at a temperature in the range of 10 to 40° C., and/or at a pH in the range of 6 to 8; and/or wherein the reaction is carried out at an initial ferulic acid concentration of 1 to 50 mM.

11. The process of claim 1, wherein the reaction is performed in whole cells of said bacterial strains.

12. The process of claim 1, wherein said bacterial strain is applied in free or immobilized form.

13. The process of claim 1 performed continuously or discontinuously.

14. The genetically engineered *Pseudomonas* strain as defined in claim 1.

15. The process of claim 4, wherein expression of the genes for feruloyl-CoA synthetase (fcs) and enoyl-CoA hydratase (ech) is under the control of a regulatory element comprising a strong inducible promoter.

16. The process of claim 4, wherein expression of the genes for feruloyl-CoA synthetase (fcs) and enoyl-CoA hydratase (ech) is under the control of the strong tac promoter.

17. The process of claim 4, wherein expression of the genes for feruloyl-CoA synthetase (fcs) and enoyl-CoA hydratase (ech) is in combination with lacI or lacI$^q$.

* * * * *

SEQUENCE LISTING

<160> NUMBER OF SEQ ID NOS: 53

<210> SEQ ID NO 1
<211> LENGTH: 31
<212> TYPE: DNA
<213> ORGANISM: Artificial Sequence
<220> FEATURE:
<223> OTHER INFORMATION: PCR primer

<400> SEQUENCE: 1
aaaaaaggat cctaaagcaa tggcgaaacc c                          31

<210> SEQ ID NO 2

```
<211> LENGTH: 32
<212> TYPE: DNA
<213> ORGANISM: Artificial Sequence
<220> FEATURE:
<223> OTHER INFORMATION: PCR timer

<400> SEQUENCE: 2
aaaaaaaagc ttacccagta cgccaacagc ct                                  32

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3
aaaaaaaagc ttgacagtgc cggcaagcca                                     30

<210> SEQ ID NO 4
<211> LENGTH: 32
<212> TYPE: DNA
<213> ORGANISM: Artificial Sequence
<220> FEATURE:
<223> OTHER INFORMATION: PCR primer

<400> SEQUENCE: 4
aaaaaaggat ccgtggtctg tcagctgtcc tt                                  32

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
aaaaaaggat cctaaagcac gatgccgagg                                     30

<210> SEQ ID NO 6
<211> LENGTH: 31
<212> TYPE: DNA
<213> ORGANISM: Artificial Sequence
<220> FEATURE:
<223> OTHER INFORMATION: PCR primer

<400> SEQUENCE: 6
aaaaaagaat tctagacctc cggcaagatg a                                   31

<210> SEQ ID NO 7
<211> LENGTH: 32
<212> TYPE: DNA
<213> ORGANISM: Artificial Sequence
<220> FEATURE:
<223> OTHER INFORMATION: PCR primer

<400> SEQUENCE: 7
aaaaaagaat tccatgctca ttcctcttgt tg                                  32

<210> SEQ ID NO 8
<211> LENGTH: 32
<212> TYPE: DNA
<213> ORGANISM: Artificial Sequence
<220> FEATURE:
<223> OTHER INFORMATION: PCR primer

<400> SEQUENCE: 8
```

| | |
|---|---|
| aaaaaaggat ccttatgcga ttcggctaga ga | 32 |

<210> SEQ ID NO 9
<211> LENGTH: 31
<212> TYPE: DNA
<213> ORGANISM: Artificial Sequence
<220> FEATURE:
<223> OTHER INFORMATION: PCR primer

<400> SEQUENCE: 9

| | |
|---|---|
| aaaaaaggat cccccgcgct tgtcgatatc c | 31 |

<210> SEQ ID NO 10
<211> LENGTH: 31
<212> TYPE: DNA
<213> ORGANISM: Artificial Sequence
<220> FEATURE:
<223> OTHER INFORMATION: PCR primer

<400> SEQUENCE: 10

| | |
|---|---|
| aaaaaaccat ggcatgcgat tctccttgcg t | 31 |

<210> SEQ ID NO 11
<211> LENGTH: 29
<212> TYPE: DNA
<213> ORGANISM: Artificial Sequence
<220> FEATURE:
<223> OTHER INFORMATION: PCR primer

<400> SEQUENCE: 11

| | |
|---|---|
| aaaaaaccat ggtgagcgtc acccgaggg | 29 |

<210> SEQ ID NO 12
<211> LENGTH: 31
<212> TYPE: DNA
<213> ORGANISM: Artificial Sequence
<220> FEATURE:
<223> OTHER INFORMATION: PCR primer

<400> SEQUENCE: 12

| | |
|---|---|
| aaaaaaggat ccggtcagtc agcctgttga t | 31 |

<210> SEQ ID NO 13
<211> LENGTH: 29
<212> TYPE: DNA
<213> ORGANISM: Artificial Sequence
<220> FEATURE:
<223> OTHER INFORMATION: PCR primer

<400> SEQUENCE: 13

| | |
|---|---|
| aaaaaagtcc agacaggacg gcggcaagg | 29 |

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14

| | |
|---|---|
| aaaaaatgta cacatgctga gcctctgcgg | 30 |

<210> SEQ ID NO 15
<211> LENGTH: 31
<212> TYPE: DNA

<213> ORGANISM: Artificial Sequence
<220> FEATURE:
<223> OTHER INFORMATION: PCR primer

<400> SEQUENCE: 15
aaaaaagtcc agagtagtcg atacccgggg c                                31

<210> SEQ ID NO 16
<211> LENGTH: 33
<212> TYPE: DNA
<213> ORGANISM: Artificial Sequence
<220> FEATURE:
<223> OTHER INFORMATION: PCR primer

<400> SEQUENCE: 16
aaaaaaggat ccctcttgtt gtcgttatag aga                              33

<210> SEQ ID NO 17
<211> LENGTH: 29
<212> TYPE: DNA
<213> ORGANISM: Artificial Sequence
<220> FEATURE:
<223> OTHER INFORMATION: PCR primer

<400> SEQUENCE: 17
aaaaaacata tgagcaaata cgaaggccg                                   29

<210> SEQ ID NO 18
<211> LENGTH: 32
<212> TYPE: DNA
<213> ORGANISM: Artificial Sequence
<220> FEATURE:
<223> OTHER INFORMATION: PCR primer

<400> SEQUENCE: 18
aaaaaagaat tcggttctgc actcttgttg tt                               32

<210> SEQ ID NO 19
<211> LENGTH: 31
<212> TYPE: DNA
<213> ORGANISM: Artificial Sequence
<220> FEATURE:
<223> OTHER INFORMATION: PCR primer

<400> SEQUENCE: 19
aaaaaaggat cctggccatt atctggctca g                                31

<210> SEQ ID NO 20
<211> LENGTH: 32
<212> TYPE: DNA
<213> ORGANISM: Artificial Sequence
<220> FEATURE:
<223> OTHER INFORMATION: PCR primer

<400> SEQUENCE: 20
aaaaaatgta cactggtgag ctacgacatc aa                               32

<210> SEQ ID NO 21
<211> LENGTH: 31
<212> TYPE: DNA
<213> ORGANISM: Artificial Sequence
<220> FEATURE:
<223> OTHER INFORMATION: PCR primer

<400> SEQUENCE: 21
aaaaaacaat tgtcactgcc cgctttccag t                                31

<210> SEQ ID NO 22
<211> LENGTH: 30
<212> TYPE: DNA
<213> ORGANISM: Artificial Sequence
<220> FEATURE:
<223> OTHER INFORMATION: PCR primer

<400> SEQUENCE: 22
aaaaaaggat ccacggcagg aagctgctgg                                      30

<210> SEQ ID NO 23
<211> LENGTH: 31
<212> TYPE: DNA
<213> ORGANISM: Artificial Sequence
<220> FEATURE:
<223> OTHER INFORMATION: PCR primer

<400> SEQUENCE: 23
aaaaaagaat tctagaccgc gtcgccttct t                                    31

<210> SEQ ID NO 24
<211> LENGTH: 32
<212> TYPE: DNA
<213> ORGANISM: Artificial Sequence
<220> FEATURE:
<223> OTHER INFORMATION: PCR primer

<400> SEQUENCE: 24
aaaaaagaat tccatggtgt gtctccttgg ta                                   32

<210> SEQ ID NO 25
<211> LENGTH: 29
<212> TYPE: DNA
<213> ORGANISM: Artificial Sequence
<220> FEATURE:
<223> OTHER INFORMATION: PCR primer

<400> SEQUENCE: 25
aaaaaaggat cccgcgatac gtcggggcg                                       29

<210> SEQ ID NO 26
<211> LENGTH: 31
<212> TYPE: DNA
<213> ORGANISM: Artificial Sequence
<220> FEATURE:
<223> OTHER INFORMATION: PCR primer

<400> SEQUENCE: 26
aaaaaaggat ccttgacgtg catccggtca c                                    31

<210> SEQ ID NO 27
<211> LENGTH: 33
<212> TYPE: DNA
<213> ORGANISM: Artificial Sequence
<220> FEATURE:
<223> OTHER INFORMATION: PCR primer

<400> SEQUENCE: 27
aaaaaagaat tccattcatt gccgaatcgt tct                                  33

<210> SEQ ID NO 28
<211> LENGTH: 31
<212> TYPE: DNA
<213> ORGANISM: Artificial Sequence
<220> FEATURE:

<223> OTHER INFORMATION: PCR primer

<400> SEQUENCE: 28
aaaaaagaat tccatctgga cgatggccgt g                                      31

<210> SEQ ID NO 29
<211> LENGTH: 30
<212> TYPE: DNA
<213> ORGANISM: Artificial Sequence
<220> FEATURE:
<223> OTHER INFORMATION: PCR primer

<400> SEQUENCE: 29
aaaaaaggat ccgcgctacg cgaggtgttc                                        30

<210> SEQ ID NO 30
<211> LENGTH: 32
<212> TYPE: DNA
<213> ORGANISM: Artificial Sequence
<220> FEATURE:
<223> OTHER INFORMATION: PCR primer

<400> SEQUENCE: 30
aaaaaaggat ccttccatgc tcaggaccct at                                     32

<210> SEQ ID NO 31
<211> LENGTH: 35
<212> TYPE: DNA
<213> ORGANISM: Artificial Sequence
<220> FEATURE:
<223> OTHER INFORMATION: PCR primer

<400> SEQUENCE: 31
aaaaaacaat tgcatgcact tttgattaat cgatt                                  35

<210> SEQ ID NO 32
<211> LENGTH: 31
<212> TYPE: DNA
<213> ORGANISM: Artificial Sequence
<220> FEATURE:
<223> OTHER INFORMATION: PCR primer

<400> SEQUENCE: 32
aaaaaacaat tgtgattcgg gtgcgagctg t                                      31

<210> SEQ ID NO 33
<211> LENGTH: 30
<212> TYPE: DNA
<213> ORGANISM: Artificial Sequence
<220> FEATURE:
<223> OTHER INFORMATION: PCR primer

<400> SEQUENCE: 33
aaaaaaggat cccgccggac agcatgagca                                        30

<210> SEQ ID NO 34
<211> LENGTH: 28995
<212> TYPE: DNA
<213> ORGANISM: Pseudomonas putida

<400> SEQUENCE: 34
gcgtttggag ctgtattcgc gcagctcctg ctggcgttgg accaactgct gttgcaggcc       60
gccaatttcg tcctgcagtt gctggcgccg gctctggtac agcgactcct cactggccgc     120
ctggtttggc gcggctttac gcagcttttc gtcgataatc agcgggcggt cctctacctc     180

```
ggcactcaaa cgttcgactc gcagggccat ggccaggcgg tcagcctcgg tttcaccaac    240
gttggaggcg aagcgggttt catccaggcg cagcaatggc tggcccactt cgacgatctg    300
cccctccttg gcgaagattt cggcgacgat gccgccctcc aggttctgga tcttctgcac    360
cttggaagac ggaatggcct tgccttcacc ccgcgtaact tcgtcgatgg gcgcgacgct    420
ggcccataca atcaagaaca cgaagaacag gatcacgccc cagatggtca gccgcaccac    480
gcgcggtgca tcttcgatca gggccttgtt cacctcgggc agcggctggc cgccaagcga    540
gtcgctgcct ttgaaatagc gccgcaggcc gtccttgaac tgccccatat ccagcttatg    600
caacactgat ctgccccttc ttcagtgcat ccatgaccgc ggctttcggg ccgtcggcga    660
caatctgccc gcgatcgatc acgatcagcc ggtctaccag cgacagcaat gaggcacggt    720
gcgtgaccag cagtaccgtc ttgccctcca ccaccgcttg caggcgctgc ttgaggcgtt    780
cttcaccggt gttgtccatg gcgctggtcg gctcgtccag cagcaggatc tgcgggttga    840
gcagcagcgc acggcccaag gcgacgttct gccgctggcc gccggacagg ttttgccccgc    900 gttcacccac ttgcagctcg tagccgtcgg ggtgcagccg ggcgaattca tgtacgcccg    960
ccagttcagc ggcctgcagg atcaattcgt cctcgatgta gcgggcgccg ctgaccaggt    1020
tgtcacgcaa ggtgccggcc agcagctgga tatcctgggg gacgtagccg atgttgtggc    1080
gcagttcgct gacatcgatc tggcgaatgt cgacgccatc aaccagcagc gagccaccat    1140
cggcctcgta caggccgacg atgagcttgg ccagcgagct cttgccggag ccgctgcggc    1200
cgatgatgcc gaccttctcg ccagggcgga tggtcaggtt gatattcttc agggccaggt    1260
tctgctggtt cggataagtg aagtcgaccc cgcggaactc gacgctgccc tgcagcacct    1320
tgcggctcag cgggcgttct tcgaagttgc gctcttgcgg tagatccatc atgtggtcgg    1380
tggagaccat ggtcaccttg gcttgctggt agcgggccag caggccgttg agctggccca    1440
acgggccgag ggcacggccg ctgagcatgt agcaagccac caggccgccc atgctcaggt    1500
tgccgtcgat gatcaggtac acgccgacgc agatcattgc cacgcctgcc agttgctgga    1560
tcagcagggt gatgttcatc gccaggctcg acagcacttt cacgcgcagt tccagccggc    1620
tcagggtgcc gagggtttgc tcccacatat actggcgttc gctttcggcg ttgttgacct    1680
ttaccgcatc cagacccgcc agggtttcga tcaggctgga ctggcgctct gatgccaaag    1740
ccatggtccg ctccatggtc gccatcagtg gccgctgcag ggcgtagccg atgcccagag    1800
ccagcgggaa ggcgatgatc ggtatccaca ccaggtgccc gccaatgatg gcgatgacga    1860
tcaaaatcag gatggtaaag gcaggtcga tcaggctggt cagggtcagc gaggcgagga    1920
agtcgcgcag gccctggaac tcgtgaatgt tctgggcaaa gctgcctacc cgcgccggcc    1980
ggtacttcat cgacatgccg acgatacgtt caaacagcgt tgccgagatg atcaggtcgg    2040
tcttcttgcc ggccaggtcc aggcacaggc cgcgaaggcc tttgaggatc aggtcgaaga    2100
tatacgcgcc ggcgataccg atggccagta cccagagcgt cgaggtggcc tggtttggca    2160
ccactcggtc atacacgttc atcacgaaca gcggcgcggc caaggcgatc aggttgatca    2220
ccaggctggc ggcgatggcg tcgatataca accacttgct gcgcagcagg gtgtcgcgga    2280
accacgactt cgctcgtggg atgaggttgc cgtggttgac atcgaacttg tgctgcggct    2340
gcgcgaagaa cacgcggccg ctgtagtcgc ttagcagggc ttcgcggctg acatgcacct    2400
cgccaccgtc gctctcgctg agtagcaggc gcgcggtgtc atcgttctcc cagccgagca    2460
ggacggcgct gcggccctcc ttgagcagca gcatggccgg catggcgata ctcgggatct    2520
```

```
gctccagctt tcgctgaagc aggcgcccct gcaggccagc ccgggccgcg gcgcgcggca    2580
gcagttcagg gctcaggcgc tgggcgggta gcggtaggcc tgttgtcagc atgacccggc    2640
tggcgggctt ctggtgcagg acacacaggc tcagcagact atccagcagg ggatcgtcat    2700
gctgactgcg tggatcgtgg ctgagttgga ctcgactgac ttcggattcc acgcggcgct    2760
ctcttcatcc ttgtggtggg tggggtgggt gtgccgtcgt taaggtcagg ccggctcacc    2820
ctggcattct ttggtgctgc aaagctgtgc tgataagggt tatcacgccc tggtgctgga    2880
gcagctggcc aatgttcgcc ttgaatcggt gttgagtaaa caattctacg tgcttcattt    2940
tcaccagact tagcggggca atgattgttt cattttttgat ccagccatca tccggcttgt    3000
tgcagcatag cctgccactc agccaaggca tgcaagggct ttgggttcca gcttagtcac    3060
tgtcagtaaa caggcgctgg tttgttggcg catatctgtg gcttgttagt caaaattcat    3120
ctatagagtg cggattcttg ccttcttgca ttcaatatcc gcaagcgatt ttcaatgatc    3180
gggataccat tattcacgca ctcgtcggtc atctctttga tttgcgacac atagctgctt    3240
gtgactcgcg cagcgttgat agccgcaagc gcccccggct ctggctggct atcgacctct    3300
gcctggccgc attccggcaa ggtttgtgct tatttggcaa tcagtgtccg ggcgattgac    3360
agtgacctga atattgacgc cagtaacgct gacattgtcg agtaagtcgg tcgcgccgcg    3420
tgatttacgg ctgctgaggt gtatgaaaaa gtgctaggac tgatggctta acaccttttt    3480
gatgatgtaa gacatttgtc ctcaggaaac gcttggctaa ggtacaaata tcaatgtgac    3540
attacattgc cgattgttta ggatggcatg tataaggtca atagtttggc agtcaggcaa    3600
ttccaaaaag ttatagacgg aatattgacg tcaaaaacgt caagagatca tcgacatagt    3660
tccgcctgaa gtggctagca agcgccgctc tggcagggaa gtaccccatc gggtcacacg    3720
gagagtccaa tgagcagcgt tgtagccatc gtcaaaagca ttgtcggcca ggttattgcg    3780
gtatccccag agggcatccg gcgtgtactt atcgaaggtg accgctgtt ggccggtgag    3840 gaagtgctca ccggtccggg tggcgcagtt actttggagc tggctgatgg ccgactgctc    3900
gatcttggac gtgacagcca atggagcgcc gatgcgcctg acagtagcac cgacctgagc    3960
caggcggcag cccaggccgc gccttcggtg gaagagttgc agcaggcaat tgctgctggt    4020
gttgacccga ctactgagct tgaagctacc gccgctggcc cgtcatcagc gggtggtggt    4080
gcgctgggcg gtgccacag cttcgtgatg ctcgaagaga cggctggccg agttgacacg    4140
acggttggct tcccgactga cgggctgggc tttgcgggcg tacccgataa ccaagaagtg    4200
ggcctgctgg acactaacgg caacaacctg gtgaccacac cgacggatac caccgtcgct    4260
actgagctga cgcttggcgc aaccccttct atcagtgaag cgggtggcgt aatcgtttat    4320
accgccaccg ttggtcaggc gccgaccacc aacctggtaa ttactctgtc caatggtgcc    4380
gtgatcgtca ttccggctgg gcagaccagt ggtagcgtca acgtcgcagt tccggcaaac    4440
gacacacctt acatcgacgg tggccagatt tcggccaccg tgacaggtag taccggtggt    4500
ggcgggctga cggtgacatt gccgcaaacg ccagcggtta cccaagtgac cgatacaatc    4560
gacactacaa ccgcgaccct gaccgcctcg ccaagcgtga ccgaaggtgg cgtgatcacc    4620
tacaccgtga ccctgagcaa ccctgcccag acgccggtga ccgtgaccct gtccaacggc    4680
caggtcatca ctgttgaagc cggcaaaacc cagggcagcg tcgatttcca gaccccggcc    4740
aatgacgtct acaacaacgg ttcgaccgtc agcgtcacca tcgagaacgc caccggcggt    4800
aatttcgagc aactgacccc gaatccgacc ccggctcaga ccacgatcaa cgactcggtc    4860
gacaccacca ccgcgaccct gacggcgagc ccgtcggtca ccgaaggcgg cgtgatcact    4920
```

```
tacaccgtga ccctgagcaa ccctgcccag acgccggtaa ccgtgaacct gtccaacggc    4980
caaacgatta ccgttgaagc gggtaaaacc cagggcagcg tcgatttcca gaccccggcc    5040
aatgacgtct acaacaacgg ctcgaccgtc agcgtcacca tcgagagcgc cactggcggc    5100
aacttcgaac agctgacccc gaacccgacg ccggctcaga ccacgatcaa cgactcggtc    5160
gacaccacca ccgcgaccct gacggcgagc cgtcggtca ccgaaggcgg cgtgatcacc     5220
tacaccgtga ccctgagcaa tcctgcccag acgccggtaa ctgtgaccct gtccaacggc    5280
caaacgatta ccgttgaagc gggtaaaacc cagggcagcg tcgatttcca gaccccggcc    5340
aatgacgtct acaacaacgg ttcgacggtc agcgtcacca tcgagaacgc cacgggcggt    5400
aatttcgagc aactgacccc gaacccgacg ccggctcaga ccacgatcaa cgactcggtc    5460
gacaccacta ccgcgaccct gacggcgagc cgtcggtca ccgaaggcgg cgtgatcact     5520
tacaccgtga ccctgagcaa tcctgcccag acgccggtga cagtgaccct gtccaacggc    5580
caaaccatta ccgttgaagc cggcaaaacc cagggcagcg tcgatttcca gaccccggcg    5640
aatgacgtct acaacaacgg ttcgactgtc agtgtcacca tcgagaacgc caccggcggt    5700
aatttcgagc aactgacccc gaatccgacg ccggctcaga ccacgatcaa cgactcggtc    5760
gatgccacca ccgcgaccct gacggcgagc cgtcggtca ccgaaggcgg cgtgatcacc     5820
tacaccgtga ccctgagcaa tcctgcccag acgccggtga cagtgaccct gtccaacggc    5880
caaaccatta ccgttgaagc cggcaagacc cagggcagcg tcgatttcca gaccccggcg    5940
aatgacgtct acaacaacgg ttcgaccgtc agcgtcacca tcgagaacgc cactggcggc    6000
aacttcgaac agctgacccc gaacccgacg ccggctcaga ccacgatcaa cgactcggtc    6060
gatgccacca ccgcgaccct gacggcgagc cgtcggtca ccgaaggcgg cgtgatcacc     6120
tacaccgtga ccctgagcaa tcctgcccag acgccggtga cagtgaccct gtccaacggc    6180
caaaccatta ccgttgaagc cggcaagacc cagggcagcg tcgatttcca gaccccggcg    6240
aatgacgtct acaacaacgg ttcgaccgtc agcgtcacca tcgagaacgc cacaggcggt    6300
aatttcgagc aactgacccc gaatccgacc ccggctcaga ccacgatcaa cgactcggtc    6360
gatgccacca ccgcgaccct gacggcgagc cgtcggtca ccgaaggcgg cgtaatcacc     6420
tacaccgtga ccctgagcaa tcctgcccag acgccggtaa ccgtgaccct gtccaacggc    6480
caggtcatca ctgttgaagc cggcaaaacc cagggcagcg tcgatttcca gaccccggcc    6540
aatgacgtct acaacaacgg ttcgaccgtc agcgtcacca tcgagaacgc caccggcggc    6600
aacttcgaac agctgacccc gaacccgacg ccggctcaga ccacgatcaa cgactcggtc    6660
gatgccacca ccgcgaccct gacggcgagc cgtcggtca ccgaaggcgg cgtgatcacc     6720
tacaccgtga tcctgagcaa tcctgcccag acgccggtaa ccgtgaccct gtccaacggc    6780
caaaccatta ccgttgaagc cggcaagacc cagggcagcg tcgatttcca gaccccggcg    6840
aatgacgtct acaacaacgg ttcgactgtc agcgtcacca tcgagaacgc cacaggcggt    6900
aatttcgagc aactgacccc gaacccgacg ccggctcaga ccacgatcac cgactcggtc    6960
gacaccacta ctgcgaccct gaccgcctcg ccaagcgtga ccgaaggcgg cgtgatcacc    7020
tacaccgtga ccctgagcaa tcctgcccag acgccggtaa ccgtgaccct tgtccaacggc   7080 caaaccatta ccgttgaagc gggtaaaacc cagggcagcg tcgatttcca gaccccggcc    7140
aatgacgtct acaacaacgg ctcgaccgtc agcgtcacca tcgagagcgc cacgggcggc    7200
aacttcgaac atctgactcc gaatccgacc ccagcctcga ctgtcatcaa tgacagcatc    7260
```

-continued

```
gataccgtca ccgtaagtat tgtcagcaat ggcaatgtga ccgaagacca gcagccttcc    7320
tttactgtga agtaagcca ggcgctggac cgtccgttga cggtaaccct gtctaacggc     7380
gacaccgtga cgatcgaagc cggtaagacc gaagtcgagt acaagacctc ggttcagggc    7440
gatgacgtct atcttgatgc aggctccatc acgctcagtg ttaccgacgc tacagttccg    7500
ggtgccacct tcgagaagct ggccttgggt ggcccggcta ccgttgagat ctcggacact    7560
atcagtgaag tggtggccaa actgactgcc accccttcgg tgaccgaagg cggtgagatc    7620
acctacacca tcaccctgac caacaaagac ggtctgccga tcaataacca ctcggagctg    7680
tacttcaagc tgaccgatgg cactactgtc gtcgtggcag ccaacagcac caccggttcg    7740
gccactgtag ccgccccgga caacgtctat gtcggcacca accagccggt ggtcaatgcc    7800
atcgacgcgg tcagcggcgc agatgcatgg aagttcgaaa acctgaacct ggacaagacc    7860
ccggtcagca ccgaggtcac cgacgagcca ggtacgccag gcaacgaagg cgatatcgtc    7920
aaggtcacca tcacggccga ccagacttcg gtagccgaga cgtcaaaacc gaccttcact    7980
gtgcacatca acaccgccct ggctcacgac ctggtcgtga ccctgagcaa caacgctcag    8040
gtcaccatca aggccggcga aaccagcgca ccgtacactc acgacgcgca gggcgatgac    8100
gtctatcagg atgcgggcca gatcagcctg gcatcaact cggcggtgga cgccactggt     8160
gctgcgttcg agaacctcga gttgggcggt gccgcgaaag tggatgtcac cgacaccctc    8220
gacgaggtgg tggccaagct gactgccact ccgtcggtca ccgaaggcgg cgagatcacc    8280
tacaccatca cgctgaccaa caaagacggt ctgccgatca ataaccactc ggagctgtac    8340
ttcaagctga ccgatggcac tactgtcgtc gtggcagcca acagcaccac cggttcggcc    8400
actgtagccg ccccggacaa cgtctatgtc ggcaccaacc agccggtggt caatgccatc    8460
gacgcggtca gcggcgcaga tgcatggaag ttcgaaaacc tgaacctgga caagaccccg    8520
gtcagcaccg aggtcaccga cgagccaggc actccaggca acgaaggcga catcgtcaag    8580
gtcaccatca cggctgacca gacttcggta gccgagaacg tcaagccgac cttcaccgtg    8640
cacgtcaacc agccgctggc ccacgacctg gtcgtgaccc tgagcaacaa cgcccaggtc    8700
accatcaagc tggtgagac cagcgcgccg tacacccacg acgcgcaagg cgatgacgtc     8760
tatcaggacg ctggccagat cagcttgggc atcaactcgg cggtggacgc cactggtgct    8820
gcattcgaga accttgagct gggcggtgct gcttcggttc aagtcaccga caccctcgac    8880
gaagtggtgg ccaagctgac tgccaccct tcggtgaccg aaggcggtga gatcacctac     8940
accatcaccc tgaccaacaa agacggtctg ccgatcaata accatcgga gctgtacttc     9000
aagctgaccg acggcaccac tgtcgtcgtg gcagccaaca gcaccacggg ctcggcgact    9060
gcaaccgcac cagacaacgt ctatgtcggc accaacgcgc cggtgatcaa tgccatcgac    9120
gcggtcagcg gcgcagatgc gtggaagttt gaaaacctga acctggacaa gaccccggtc    9180
agcaccgagg tcaccgacga gccaggcact ccaggcaacg aaggcgacat cgtcaaggtc    9240
accatcacgg ccgaccagac ttcggtggcc gagaacgtca accgaccttt caccgtgcac    9300
gtcaaccagc cgctggccca cgacctggtc gtgaccctga gcaacaatgc tcaggtcacc    9360
atcaaggctg gcgaaaccag cgcgccgtac acccacgatg cgcaaggcga tgacgtctat    9420
caggacgctg gccagatcag cctgggcatc aactcggcag tagacgccac tggtgctgcg    9480
ttcgagaacc ttgagctggg cggttccgct tcggttcaag tcaccgacac cctcgacgaa    9540
gtggtggcca agctgactgc cacccctcg gtgaccgaag cggtgagat cacctacacc      9600
atcaccctga ccaacaaaga cggtctgccg atcaacaacc actcggagct gtacttcaag    9660
```

```
ctgaccgacg gcaccaccgt cgtcgtggca gccaacagca ccaccggttc ggccactgca    9720
accgcaccag acaacgtcta tgtcggcacc aacgcgccgg tggtcaatgc catcgacgcg    9780
gtcagcggcg cagatgcgtg gaagttcgaa aacctgaacc tggacaagac cccggtcagc    9840
accgaggtga ccgacgagcc aggcacacca ggtaacgaag gcgatatcgt caaggtcacc    9900
atcaccgccg accaggcttc ggtggccgag aacgtcaaac cgaccttcac cgtgcacgtc    9960
aaccagccgc tggcccacga cctggtcgtg accctgagca caacgctca ggtcaccatc    10020 aaggctggcg aaaccagcgc gccgtacacc cacgacgcgc aaggcgatga cgtctatcag    10080
gatgcgggcc agatcagcct cggcatcacg tccgctgtgg atgtagacgg tcacaccttc    10140
gagaacctgc aactgggcgg caacgcttcg gttcaagtga ccgacaccct cgacgaggtg    10200
gtggcgaagc tgaccgcgac cccttcagtc accgaaggcg gtgagatcac ctacaccatc    10260
accctgacca caaagatgg tctgccgatc aacaaccact cggagctgta cttcaagctg    10320
accgacggca ccactgtcgt cgtggcagcc aacagcacca cgggctcggc cactgcaacc    10380
gcaccagaca acgtctatgt cggcactaat gcgccggtgg tcaatgccat cgacgccgtc    10440
agcggcgcag atgcgtggaa gttcgaaaac ctgaacctgg acaagacccc ggtcagcact    10500
accgtcactg acgagccagg cactccaggc aacgaaggcg acatcgtcaa ggtcaccatc    10560
acggccgacc agacctcggt agccgagaac gtcaaaccga ccttcactgt gcacgtcaat    10620
cagccgctgg cccacgacct gatcgtgacc ctgagcaaca acgctcaggt caccatcaag    10680
gccggtgaaa ccagcgcgcc gtacacccac gacgcgcaag gcgatgacgt ctatcaggac    10740
gctggccaga tcagcttggg catcaactcg gcggtggacg ccactggtgc tgcgttcgag    10800
aacctgcaac tgggcggcaa cgcttcggtt caagtgaccg acaccctcga cgaagtcgtg    10860
gcgaagctga ccgcgacccc ttcggtgacc gaaggcggcg agatcaccta ccatcacg    10920 ctgaccaaca aagacggtct gccgatcaat aaccactcgg agctgtactt caagctgacc    10980
gatggcacta ctgtcgtcgt ggcagccaac agcaccaccg gttcggccac tgtagccgcc    11040
ccggacaacg tctatgtcgg caccaacgcg ccggtggtca atgccatcga cgcggtcagc    11100
ggcgcagatg cgtggaagtt cgaaaacctg aacctggaca agaccccggt cagcactacc    11160
gtcactgacg agccaggcac tccaggcaac gaaggcgaca tcgtcaaggt caccatcacg    11220
gccgaccaga cttcggtagc cgagaacgtc aagccaacct tcaccgtgca cgtcaaccag    11280
ccgctggctc acgacctggt cgtgaccctg agcaacaacg ctcaggtcac catcaaggcc    11340
ggtgagacca gtgcgccgta cacccacgac gcgcaaggcg atgacgtcta ccaggacgct    11400
ggccagatca gcctgggcat cacgtccgct gtggatgtag acggtcacac cttcgagaac    11460
ctgcaactgg gcgcaacgc ttcggttcaa gtgaccgaca cctcgacga ggtggtggcg    11520 aagctgaccg cgaccccttc ggtcaccgaa ggcggtgaga tcacctacac catcaccctg    11580
accaacaaag acggtctgcc gatcaacaac cactcggagc tgtacttcaa gctgaccgac    11640
ggcaccaccg tcgtcgtggc agccaacagc accaccggtt cggccactgc aaccgccccg    11700
gacaacgtct atgtcggcac caacgcgccg tggtcaatg ccatcgacgc cgtcagcggc    11760
gcagatgcgt ggaagttcga aaacctgaat ctggacaaga cccggtcag caccgaggtc    11820 actgacgagc caggcactcc aggcaacgaa ggcgatatcg tcaaagtcac tattactgct    11880
gaccagacct cggtggccga gaacgtcaaa ccgaccttca ccgtacatat caacaccgcc    11940
ttggcccacg acctggtcgt gaccctgagc aacaacgccc aggtcaccat caaggccggc    12000
```

```
gaaaccagcg cgccgtacac ccacgctgcg cagggtgatg acgtttacaa cgacgctggc   12060
cagatcagcc tgggcatcac ctcggcggtg acgccactg  gtgcaacctt cgagaacctg   12120
gcgctgggcg gtgccgcgaa ggtggatgtc accgacacca ccgacgaagt cgtggccaag   12180
ttgaccgcca ccccgtcggt caccgaaggc ggcgagatca cctacaccat cacgctgacc   12240
aacaaagacg gtctgccaat caacaaccac agtgcattga ccttcacgct gagcgacggc   12300
aaaaccgtca tcaccgtgcc ggctaatggc accgtgggta ctgccactgt cactgccccg   12360
gacaacgtct acgtcggcac caacgaccct gtgatcaaat cgatcgcaac cgttgaaggt   12420
gcggatgtcg gcaagttcga gcaactgacg ctggacaaga ccccggtcag cacgtcggtc   12480
accgacgagc cgggcacccc aggcaacgaa ggcgacttgg tcaaggtcac catcacagcc   12540
gaccagacct cggtggctga aacgtcaaa  ccgaccttca ccgtgcacgt caaccagccg   12600
ctggcccacg acctggtcgt gaccctgagc aacaatgccc aggtcaccat caaggctggc   12660
gaaaccagcg cgccgtacac ccacgctgcg cagggtgatg acgtttacaa cgacgctggc   12720
cagatcagcc tgggcatcac ctcggcggtg acgccactg  gtgcgaccttc gagaacctg    12780 gagctgggcg gtgccgcgaa ggtggatgtc accgacacca ccgacgaagt cgtggccaag   12840
ttgaccgcca ccccgtcggt caccgaaggc ggcgagatca cttacaccat caccctgacc   12900
aacaaagatg gtctgccgat caacaaccac agtgcattga ccttcacgct gagcgacggc   12960
aaaaccgtca tcaccgtgcc ggccaacggc accgtgggac tgcaaccgt  gactgccccg   13020 gacaacgtct acgtcggtac caacgaccct gtgatcaaat cgatcgcaac cgttgaaggt   13080
gcggacgtcg gtaagttcga gcaactgacg ctggacaaga cgccggtcag cactaccgtc   13140
accgacgagc ctggtacccc aggcaacccg ggcggcagca acgaaggcga cctggtcaag   13200
gtcaccatca cggccgacca gacttcggta gccgagaacg tcaaaccgac cttcactgtt   13260
cacgtcaacc agccgctggc tcacgacctg gtcgtgaccc tgagcaacaa tgcccaggtc   13320
accatcaagg ccggtgaaac cagcgcgccg tacccccacg ctgctcaggg tgatgacgtc   13380
tacaacgacg ctggccagat cagcctgggt atcaactcgg cggtggacgc cactggtgcg   13440
accttcgaga acctcgagtt gggcggtgcc gcgaaggtgg atgtcaccga caccaccgac   13500
gaagtggtgg ccaagttgac cgcgacccct tcggtgaccg aaggcggtga gatcacttac   13560
accattaccc tgaccaacaa agacggcttg ccgatcaata ccacagtgc  attgaccttc   13620 acgctgagcg acggcaaaac cgtcatcacc gtgccggcca acggcaccgt gggcactgca   13680
accgtgactg ccccggacaa cgtctacgtc ggtaccaacg accctgtgat caaatcgatc   13740
gcaaccgttg aaggtgcgga cgtcggtaag ttcgagcaac tgacgctgga caagacgccg   13800
gtcagcacta ccgtcaccga cgagcctggt accccaggca cccgggcgg  cagcaacgaa   13860 ggcgacctgg tcaaggtcac catcacggcc gaccagactt cggtagccga gaacgtcaaa   13920
ccgaccttca ctgttcacgt caaccagccg ctggctcacg acctggtcgt gaccctgagc   13980
aacaatgccc aggtcaccat caaggccggt gaaaccagcg cgccgtacac ccacgctgct   14040
cagggtgatg acgtctacaa cgacgctggc cagatcagcc tgggtatcac gtctgctgtg   14100
gatgtagacg gtcgcacctt cgaaaacctg agctgggcg  gtgcggcttc ggttcaagtg   14160
accgatacca ccgacgaagt ggtggccaag ttgaccgcga ccccttcggt gaccgaaggc   14220
ggtgagatca cttacaccat taccctgacc aacaaagacg gcttgccgat caataaccac   14280
agtgcattga ccttcacgct gagcgacggc aaaaccgtca tcaccgtgcc ggccaacggc   14340
accgtgggca ctgcaaccgt gactgccccg gacaacgtct acgtcggtac caacgaccct   14400
```

```
gtgatcaaat cgatcgcaac cgttgaaggt gcggatgtcg gcaagttcga acaactgaca   14460
ctcgacaaga ccccggtcag cactaccgtc accgacgagc tggtacccc aggcaacccc    14520 ggcggcagca acgaaggcga cctggtcaag gtcaccatca ccgccgacca gacttcggta   14580
gccgagaacg tcaaaccgac cttcactgtt cacgtcaacc agccgctggc tcacgacctg   14640
gtcgtgaccc tgagcaacaa cgcccaggtc accatcaagg ccggcgaaac cagcgcgccg   14700
tacacccacg ctgcgcaggg cgatgacgtc tacaacgatg ctggccagat cagcctgggt   14760
atcaactcgg cggtggatgc cactggtgcg accttcgaga acctgcaact gggcggcaac   14820
gcttcggttc aagtgaccga caccaccgac gaagtggtgg ccaagctgac cgcgaccccg   14880
tcggtcaccg aaggcggcga gatcacttac accatcacgc tgaccaacaa agacggtctg   14940
ccgatcaaca accacagtgc attgaccttc acgctgagcg acggcaaaac cgtcatcacc   15000
gtgccggcca acggcaccgt gggcactgct accgtcactg ccccggacaa cgtctacgtc   15060
ggtaccaacg accctgtgat caaatcgatc gcaaccgttg aaggtgcgga cgtcggcaag   15120
ttcgagcaac tgacgctgga caagacgccg gtcagcacgt cggttaccga cgagccaggt   15180
acgccgggca acgaaggcga cctggtcaag gtcaccatca cagccgacca gacttcggtg   15240
gccgagaacg tcaaaccgat cttcaccgtg cacgtaaacc agccgctggc tcacgacctg   15300
gtcgtgaccc tgagcaacaa cgcccaggtc accatcaagg ccggcgagac cagcgcgcca   15360
tacacccacg ctgcgcaagg cgatgacgtc tacaacgacg ctggccagat cagcctgggc   15420
atcacgtctg ctgtggatgt agacggtcgc accttcgaga acctgcaact gggcggcaac   15480
gcttcggttc aagtcaccga caccaccgac gaagtggtgg ccaagctgac cgcgaccccg   15540
tcggtgaccg aaggcggcga gatcacctac accatcacgc tgaccaacaa agacggtctg   15600
ccgatcaaca accacagtgc attgaccttc acgctgagcg acggcaaaac cgtcatcacc   15660
gtgccggcca acggtaccgt gggtactgct accgtgactg ccccggacaa cgtctacgtc   15720
ggcaccaacg accctgtcgt gatgtcgatc gcaaccgttg gaggtgcgga cgtcggcaag   15780
ttcgagcaac tgacgctgga caagacccccg gtcagcacta ccgtcaccga cgagcctggc   15840
accccaggca atccgggcgg cagcaacgaa ggcgacctgg tcaaggtcac catcacggcc   15900
gaccagactt cggtggccga aacgtcaaa ccgacgttca ccgtacacgt caaccagccg   15960
ctggcccacg acctggtcgt gaccctgagc aacaacgccc aggtcaccat caaggctggc   16020
gagaccagcg cgccgtacac ccacgctgcg cagggtgatg acgtttacaa cgacgctggc   16080
cagatcagcc tgggcatcaa ctcggcggtg acgccactg tgcgaccttt cgagaacctg   16140
gcgctgggcg gtgccgcgaa ggtggatgtc accgacacca ccgacgaagt cgtggccaag   16200
ttgaccgcca ccccgtcggt caccgaaggc ggcgagatca cctacaccat cacgctgacc   16260
aacaaagacg gtctgccaat caacaaccac agtgcattga ccttcacgct gagcgacggc   16320
aaaaccgtca tcaccgtgcc ggctaatggc accgtgggta ctgccactgt cactgccccg   16380
gacaacgtct acgtcggcac caacgaccct gtgatcaaat cgatcgcaac cgttgaaggt   16440
gcggatgtcg gcaagttcga gcaactgacg ctggacaaga ccccggtcag cacgtcggtc   16500
accgacgagc cgggcacccc aggcaacgaa ggcgacttgg tcaaggtcac catcacagcc   16560
gaccagacct cggtggctga aacgtcaaa ccgaccttca ccgtgcacgt caaccagccg   16620
ctggcccacg acctggtcgt gaccctgagc aacaatgccc aggtcaccat caaggccggt   16680
gaaaccagcg cgccatacac ccacgctgcg caaggcgatg acgtctacaa cgacgctggc   16740
```

```
cagatcagcc tgggcatcac gtccgctgtg gatgtagacg gtcgcacctt cgaaaacctg   16800
caactgggcg gtgcggctac cgttcaagtg accgatacca ccgacgaagt agtggccaag   16860
ctgaccgcga ccccttcggt caccgaaggt ggcgagatca cttacaccat caccctgacc   16920
aacaaagacg gcctgccgat caacaaccac agtgcattga ccttcacgct gagcgacggc   16980
aaaaccgtca tcaccgtgcc ggctaatggc accgtgggta ctgccaccgt gactgccccg   17040
gacaacgtct acgttggcac caacgaccct gtgatcaaat cgatcgcaac cgttgaaggt   17100
gcggatgtcg gcaagttcga gcaactgaca ctggacaaga ccccggtcag cacgtcggtt   17160
accgacgagc caggtacgcc gggcaacgaa ggcgacctgg tcaaggtcac catcacagcc   17220
gaccagactt cggtggccga aacgtcaaa ccgaccttca ctgttcacgt caaccagccg   17280
ctggctcacg acctggtcgt gaccctgagc aacaatgccc aggtcaccat caaggccggc   17340
gagaccagcg cgccatacac ccacgctgcg cagggcgatg acgtttacaa cgatgctggc   17400
cagatcagcc tgggtatcaa ctcggcggta gacgccactg gcgctacgtt cgagaacctg   17460
caactgggcg gtgcggctac cgttcaagtg accgatacca ccgacgaagt agtggccaag   17520
ctgaccgcga ccccttcggt caccgaaggt ggcgagatca cttacaccat caccctgacc   17580
aacaaagacg gcctgccgat caacaaccac agtgcattga ccttcacgct gagtgacggc   17640
aaaaccgtca tcaccgtgcc ggcaacggc accgtgggca ctgctaccgt cactgccccg   17700
gacaacgtct acgtcggcac caacgaccct gtcgtgatgt cgatcgcaac cgttggaggt   17760
gcggacgtcg gtaagttcga gcaactgaca ctcgacaaaa ccccggtcag cacgtcggtc   17820
accgacgagc cgggtacccc aggcaacgaa ggcgacctgg tcaaggtcac catcaccgcc   17880
gaccagactt cggtggccga aacgtcaag ccgaccttca ccgtgcacgt caaccagccg   17940
ctggctcacg acctggtcgt gaccctgagc aacaacgccc aggtcaccat caaggccggc   18000
gaaaccagcg cgccgtacac ccacgctgcg cagggcgatg acgtctacaa cgatgctggc   18060
cagatcagcc tgggcatcaa ctcggcggtg acgccactg gtgcgacctt cgagaacctc   18120
gagctgggcg gtgccgcgaa ggtggatgtc accgacacca ccgacgaagt ggtggccaag   18180
ctgaccgcga ccccttcggt aaccgaaggc ggcgagatca cctacaccat cacgctgacc   18240
aacaaagatg gtctgcctat cgacaagcat gcggcgctga cctttacccct ggacgatggc   18300 aaaaccacca tcaccatccc ggctaacggt acaaccggca ctgccaccgt gactgccccg   18360
gacaacgtct acgtcggcac caacgaccct gtcgtgatgt cgatcgcaac cgttggaggt   18420
gcggacgtcg gtaagttcga gcaactgaca ctcgacaaga ccccggtcag cacgtcggtc   18480
accgacgagc cgggtacccc aggcaacgaa ggcgacctgg tcaaggtcac catcaccgcc   18540
gaccagactt cggtagccga aacgtcaaa ccgaccttca ctgttcacgt caaccagccg   18600
ctggctcacg acctggtcgt gaccctgagc aacaacgctc aggtcaccat caaggctggc   18660
gagaccagcg cgccgtacac ccacgctgcg cagggtgatg acgtctacaa cgatgcgggc   18720
cagatcagcc tgggcatcac gtccgctgtg gatgtagacg gtcgcacctt cgaaaacctg   18780
gagctgggcg gtgccgcttc ggtccaagtg accgacaccc tcgacgaagt ggtggccaaa   18840
ctgaccgcca ccccttcggt gaccgaaggc ggtgagatca cttacaccat cacgctgacc   18900
aacaaagacg gtctgccgat caacaaccac agtgcattga ccttcacgct gagcgacggc   18960
aaaaccgtca tcactgtgcc ggccaacggc accgtgggca ctgccaccgt gactgctccg   19020
gacaacgtct acgtcggcgc taacgaccct gtcgtgatgt cgatcgcaac cgttgagggc   19080
gcggatgtcg gcaagttcga acagcttacg ctggacaaga cgccggtcag cacgtcggtg   19140
```

```
accgacgagc caggtacgcc gggcaacgaa ggcgacttgg tcaaggtcac catcaccgcc    19200
gaccagacct cggtggccga aacgtcaag ccgaccttca ccgtgcacgt caaccagccg    19260
ctggcccacg acctggtcgt gaccctgagc aacaacgccc aggtcaccat caaggctggc    19320
gaaaccagcg cgccgtacac ccacgctgcg cagggtgatg acgtttacaa cgacgctggc    19380
cagatcagcc tgggcatcac ctcggcggtg gacgccactg gtgcgacctt cgagaacctg    19440
gagctgggcg gtgcggcttc ggttcaagtg accgacacca ccgacgaagt ggtggccaag    19500
ctgactgcga ccccgtcggt caccgaaggc ggcgagatca cctacaccat caccctgacc    19560
aacaaagacg gcctgccgat caacaaccac agtgcattga ccttcacgct gagcgacggc    19620
aagaccgtca tcaccgtgcc ggccaacggc accgtgggca ctgcaaccgt gactgccccg    19680
gacaacgtct acgtcggcag caacgaccct gtcgtgatgt cgatcgctac cgttggcggt    19740
gcggacgtcg gtaagttcga gcaactgacg ctggacaaga cgccggtcag cacgtcggtc    19800
accgacgagc caggtacccc aggcaacgaa ggcgacctgg tcaaggtcac catcaccgcc    19860
gaccagactt cggtggccga aacgtcaaa ccgaccttca ctgttcacgt caaccagccg    19920
ctggctcacg acctggtcgt gaccctgagc aacaatgccc aggtcaccat caaggccggc    19980
gagaccagcg cgccgtacac ccacgctgcg cagggcgatg acgtttacaa cgatgctggc    20040
cagatcagcc tgggcatcaa ctcggcggta gacgccactg gtgcgacctt cgagaacctg    20100
caactgggcg gcaacgcttc ggttcaagtg accgacacca ccgacgaagt ggtggccaag    20160
ctgactgcga ccccgtcggt caccgaaggc ggcgagatca cctacaccat cacgctgacc    20220
aacaaagacg gtctgccaat caacaaccac agtgcattga ccttcacgct gagcgacggc    20280
aaaaccgtca tcaccgtgcc ggccaacggc accgtgggca ctgctaccgt cactgccccg    20340
gacaacgtct acgtcggcac caacgaccct gtcgtgatgt cgatcgcaac cgttggaggt    20400
gcggacgtcg gtaagttcga gcaactgacg ctggacaaga cccggtcag cactaccgtc    20460 accgacgagc ctggcacccc aggcaacccg ggcggcagca acgaaggcga cctggtcaag    20520
gtcaccatca cggccgacca gacttcgttg gccgagaacg tcaaaccgac gttcaccgta    20580
cacgtcaacc agccgctggc ccacgacctg gtcgtgaccc tgagcaacaa cgcccaggtc    20640
accatcaagg ctggcgagac cagcgcgccg tacacccacg ctgcgcaggg tgatgacgtt    20700
tacaacgacg ctggccagat cagcctgggc atcaactcgg cggtggacgc cactggtgcg    20760
accttcgaga acctcgagct gggcggtgcg gcttcggttc aagtgaccga taccaccgac    20820
gaagtggtgg ccaagctgac cgcgacgcct cggtgaccg aagtggtga gatcacctac    20880 accatcaccc tgaccaacaa agatggtctg ccgatcaaca accacagtgc attgaccttc    20940
accctgagca cgcaaaac cgtcatcacc gtgccggcta atggcaccgt gggtactgcc    21000
actgtcactg ccccggataa cgtctacgtc ggcagcaacg accctgtcgt gatgtcgatc    21060
gctaccgttg gcggtgcgga tgtcggcaag ttcgagcaac tgacactgga caagaccccg    21120
gtcagcacgt cggttaccga cgagccaggt acgccgggca acgaaggcga cctggtcaag    21180
gtcaccatca cggccgacca gacttcggta gccgagaacg tcaaaccgac cttcactgtt    21240
cacgtcaacc agccgctggc tcacgacctg gtcgtgaccc tgagcaacaa tgcccaggtc    21300
accatcaagg ccggtgaaac cagcgcgccg tacacccacg ctgcgcaggg tgatgacgtc    21360
tacaacgatg ctggccagat cagcctgggt atcaactcgg cggtggacgc cactggtgcg    21420
accttcgaga acctcgagct gggcggtgcg gcttcggtcc aagtgaccga caccaccgac    21480
```

```
gaagtagtgg ccaagctgac tgcgaccccg tcggtgaccg aaggcggtga gatcacttac    21540
accattaccc tgaccaacaa agacggtctg ccgattaaca accacagtgc attgaccttc    21600
accctgagcg acggcaaaac cgtcatcacc gtgccggcta atggcaccgt gggtactgcc    21660
actgtcactg ccccggataa cgtctacgtc ggcagcaacg accctgtcgt gatgtcgatc    21720
gctaccgttg gcggtgcgga tgtcggcaag ttcgagcaac tgacgctgga caagacgccg    21780
gtcagcacgt cggttaccga cgagccaggt acgccgggca acgaaggcga cctggtcaag    21840
gtcaccatca ccgccgacca gacctcggtg gccgagaacg tcaagccgac cttcaccgtg    21900
cacgtcaacc agccgctggc ccacgacctg gtcgtgaccc tgagcaacaa cgcccaggtc    21960
accatcaagg ctggcgaaac cagcgcgccg tacacccacg ctgcgcaggg tgatgacgtc    22020
tacaacgacg ctggccagat cagcctgggt atcaactcgg cggtggacgc cactggtgcg    22080
accttcgaga acctggagct gggcggtgcc gcgaaggtgg atgtcaccga caccaccgac    22140
gaagtcgtgg ccaagttgac cgccaccccg tcggtcaccg aaggcggcga gattacctac    22200
accatcacgc tgaccaacaa agacggcctg ccgatcaaca accacagtgc attgaccttc    22260
acgctgagcg acggcaaaac cgtcatcacc gtgccggcca acggcaccgt gggcactgcc    22320
accgtcactg ccccggacaa tgtctacgtc ggtaccaacg accctgtcgt gatgtcgatc    22380
gcaaccgttg aaggcgcgga cgttggcaag ttcgagcaac tgacgctgga caagacgccg    22440
gtcagcacgt cggtgaccga cgagccgggt accccaggca acgaaggcga cttggtcaag    22500
gtcaccatca cggccgacca gacctcggtg gccgagaacg tcaagccgac gttcaccgtg    22560
cacatcaaca ccgccttggc tcacgacctg gtcgtgaccc tgagcaacaa tgcccaggtc    22620
atcatcaagg ctggcgaaac cagcgcgcca tacacccacg ctgcgcaagg cgatgacgtc    22680
tacaacgatg ctggccagat cagcctgggc attaattcgg cagtggacgc cactggtgcg    22740
accttcgaga acctgcaact gggcggcaac gcttcggttc aagtgaccga caccaccgac    22800
gaagtagtgg ccaagttgac cgcgaccccg tcggtgaccg aaggcggcga gattacctac    22860
accatcacgc tgaccaacaa agacggcctg ccgatcaaca accacagtgc attgaccttc    22920
acgctgagcg acggcaaaac cgtcatcacc gtgccggcca acggcaccgt gggtactgcc    22980
accgtgactg ctccggacaa cgtctacgtc ggtaccaacg accctgtcgt gatgtcgatc    23040
gctaccgttg aaggtgcgga cgttggcaag ttcgagcaac tgacactcga caagaccccg    23100
gtcagcactt cggtcaccga cgagccgggt accccaggca acgaaggcga cccggtcaag    23160
gtcaccatca ccgccgacca gacctcggtg gccgagaacg tcaaaccgac cttcactgtg    23220
cacgtcaacc agccgctggc ccacgacctg gtcgtgaccc tgagcaacaa cgcccaggtc    23280
accatcaagg ccggcgaaac cagcgcgccg tacacccacg acgcgcaagg cgatgacgtc    23340
tacaacgatg ctggccagat cagcctgggc atcaattcgg cggtagacgc caccggcgct    23400
acattcgaga acctggaact gggtggtgcg gcttcggttc aagtgaccga caccaccgac    23460
gaagtagtgg ccaagctgac cgcgaccccct tcggtaaccg aaggcggcga gatcacctac    23520
accatcacgc tgaccaacaa agatggtctg cctatcgaca agcatgcggc gctgacctt    23580 accctggaca tggcaaaac caccatcacc atccggcta acggtacaac cggcactgcc    23640
accgtgactg ccccggacaa cgtctacgtc ggcaccaacg accctgtcgt gatgtcgatc    23700
gcaaccgttg gaggtgcgga cgtcggtaag ttcgagcaac tgacactcga caagaccccg    23760
gtcagcacgt cggtcaccga cgagccgggt accccaggca acgaaggcga cctggtcaag    23820
gtcaccatca ccgccgacca gacttcggta gccgagaacg tcaaaccgac cttcactgtt    23880
```

```
cacgtcaacc agccgctggc tcacgacctg gtcgtgaccc tgagcaacaa cgctcaggtc   23940
accatcaagg ctggcgagac cagcgcgccg tacacccacg ctgcgcaggg tgatgacgtc   24000
tacaacgatg cgggccagat cagcctgggc atcacgtccg ctgtggatgt agacggtcgc   24060
accttcgaaa acctggagct gggcggtgcc gcttcggtcc aagtgaccga caccctcgac   24120
gaagtggtgg ccaaactgac cgccacccct tcggtgaccg aaggcggtga gatcacttac   24180
accatcacgc tgaccaacaa agacggtctg ccgatcaaca accacagtgc attgaccttc   24240
acgctgagcg acggcaaaac cgtcatcact gtgccggcca acggcaccgt gggcactgcc   24300
accgtgactg ctccggacaa cgtctacgtc ggcgctaacg accctgtcgt gatgtcgatc   24360
gcaaccgttg agggcgcgga tgtcggcaag ttcgaacagc ttacgctgga caagacgccg   24420
gtcagcacgt cggtgaccga cgagccaggt acgccgggca acgaaggcga cttggtcaag   24480
gtcaccatca ccgccgacca gacctcggtg ccgagaacg tcaagccgac cttcaccgtg   24540
cacgtcaacc agccgctggc ccacgacctg gtcgtgaccc tgagcaacaa cgcccaggtc   24600
accatcaagg ccggcgaaac cagcgcgcca tacacccacg ctgcgcaagg cgatgacgtc   24660
tacaacgacg ctggccagat cagcctgggc atcacgtccg ctgtggatgt agacggtcgc   24720
accttcgaaa acctgcaact gggcggtgcg gctaccgttc aagtgaccga taccaccgac   24780
gaagtagtgg ccaagctgac cgcgacccct tcggtcaccg aaggtggcga gatcacttac   24840
accatcaccc tgaccaacaa agacggcctg ccgatcaaca accacagtgc attgaccttc   24900
acgctgagcg acggcaaaac cgtcatcacc gtgccggcta atggcaccgt gggtactgcc   24960
accgtgactg ccccggacaa cgtctacgtt ggcaccaacg accctgtgat caaatcgatc   25020
gcaaccgttg aaggtgcgga tgtcggcaag ttcgagcaac tgacactgga caagaccccg   25080
gtcagcacgt cggttaccga cgagccaggt acgccgggca acgaaggcga cctggtcaag   25140
gtcaccatca cagccgacca gacttcggtg ccgagaacg tcaaaccgac cttcactgtt   25200
cacgtcaacc agccgctggc tcacgacctg gtcgtgaccc tgagcaacaa tgcccaggtc   25260
accatcaagg ccggcgagac cagcgcgcca tacacccacg ctgcgcaggg cgatgacgtt   25320
tacaacgatg ctggccagat cagcctgggt atcaactcgg cggtagacgc cactggcgct   25380
acgttcgaga acctgcaact gggcggtgcg gctaccgttc aagtgaccga taccaccgac   25440
gaagtagtgg ccaagctgac cgcgacccct tcggtcaccg aaggtggcga gatcacttac   25500
accatcaccc tgaccaacaa agacggcctg ccgatcaaca accacagtgc attgaccttc   25560
acgctgagtg acggcaaaac cgtcatcacc gtgccggcca acggcaccgt gggcactgct   25620
accgtcactg ccccggacaa cgtctacgtc ggcaccaacg accctgtcgt gatgtcgatc   25680
gcaaccgttg gaggtgcgga cgtcggtaag ttcgagcaac tgacactcga caaaccccg   25740 gtcagcacgt cggtcaccga cgagccgggt accccaggca acgaaggcga cctggtcaag   25800
gtcaccatca ccgccgacca gacttcggtg ccgagaacg tcaagccgac cttcaccgtg   25860
cacgtcaacc agccgctggc tcacgacctg gtcgtgaccc tgagcaacaa cgcccaggtc   25920
accatcaagg ccggcgaaac cagcgcgccg tacacccacg ctgcgcaggg cgatgacgtc   25980
tacaacgatg ctggccagat cagcctgggc atcaactcgg cggtgacgc cactggtgcg   26040 accttcgaga acctcgagct gggcggtgcc gcgaaggtgg atgtcaccga caccaccgac   26100
gaagtggtgg ccaagctgac cgcgacccct tcggtaaccg aaggcggcga gatcacctac   26160
accatcaccc tgaccaacaa agatggtctg ccaatcaaca accacagtgc attgaccttc   26220
```

-continued

```
acgctgagcg acggcaaaac cgtcatcacc gtgccggcca acggcaccgt gggcactgct    26280
accgtcactg ccccggacaa cgtctacgtc ggtaccaacg accctgtgat caaatcgatc    26340
gcaaccgttg gcggcgcgga tgttggcaag ttcgaacagc tgacactgga caagaccccg    26400
gtcagcaccg ccgtgaccga cgaaccaggt tcgggaactc caggcaccgg caacaagggc    26460
gacgtcacca ccgtcggtat taccggcacg acttctctga ccgagggtga aaccggccag    26520
tacaccctga cgctgagcaa cgcgtccaag tccgaagtca ctatcaccct tagctacagc    26580
ggtaccgccc aaaacggtga tgacttcacc ggtgttgcga ccgtgaagat tccggccaac    26640
agcacaggca cgacgttcaa catcgctacc ctcaacgaca aactggtcga aggtaccgag    26700
aacttcgtcg tgaagatcga aaccgccacg ggtggtaact tcgagaacct gcaggtcgat    26760
agcagcaaat cgagcgtgac gaccaccatt ctcgacaatg accacctgcc ggtttcgcct    26820
ggcggcgcgg tatttggcgt tgaggacacc gattacgtgt ttgcctggag tgatttcaaa    26880
gtcactgatg ccgacggcaa cactaacctg tctgtgacca ttacctcgct cccggccgcc    26940
ggcaacttgc agttcttcaa cggtactgca tgggtgaatg tggccgttgg ccaagtggtc    27000
agccaggctg atatcactgc caagaacctg aagttcgttc cggccctcaa ccagtcgggt    27060
gcggacaact acggtggtaa tggtgtgggt aaccagaagg ctgactacgc ccagttcaag    27120
ttcaagccga acgatggcac caacctgggc agcgaagtga ccatgaaggt cgatatcagc    27180
ccggttgcca acaaaccgac cctgagcttc ggcagcgccg atatcgagtc caaagggctg    27240
accaaggaag tctggaccag cctcaaaggc ctgggtactg cggcaacgg cattaccggc    27300
gaggatctga agacggtctt tgccaactcc ggcagcgcga actccagcag caccactacc    27360
aacgtgcagt ccgatggcag cgtcaccgct ggcaccggtt cgaaaacgtc gggcctgatc    27420
tacctggaag ccggcaaggt ctataccttc agtggtttgg ccgacgacag cttcgtggtc    27480
accatcggtg gcaagactgt agtcacggcc acctggggag ccggtggcgg ggtgtcgggt    27540
acctttaccc caaataccag cggctactac ccgatcgagg tctaccatgc caaccagtcc    27600
ggtccaggca gctatgacct gaacatccag gtaggctccg gtgccgttac cgacctgagc    27660
agctcgaacg tcaagatgta ccagaacgtt accgagatgg cgaacgcagg cctgggcgtg    27720
tccgacctgc acaccgtgaa tggtcagagc tactacgacg gctacaagct caacgaaggg    27780
cctgagggtg gctcggtgaa actggtcggt atttccaccg ccctgaccga cactgacggc    27840
tccgaaagcc tgaacgtaac actcagcggt atcccgaaag gtactgtgtt gagcgatggt    27900
gcaggccaca cggtcacggt aggtactgcc ccggtcgatg tgacaggctg aaaactcagc    27960
agcctgacgc tgaccccgcc ggcctattac aaaggctcgt tcgacatcac ggttacctcg    28020
actgccaccg aaagcctggg cggctcggcc atcaccaccg gcaatatccc ggtgacggtt    28080
tacggcgcga cctacaaggc cagtgtgggt acctcgggta atgacacgct gaccggtagt    28140
gaaggcaacg acatcttcgt cgctgacgta tccgggctga acgtggttca gggcaagaac    28200
tacaacatcg ccttcatggt cgatagctcg gcagtatgaa gcgacaagtc gattgccgac    28260
gccaagacgc agttggcctc ggtgttcaac acgctcaagg ccagcctggg ctcggacacc    28320
tcgggtaccg taaacatctt cctggtcgac ttcgataccc aggtaaacaa gaacgtggca    28380
gtgaaccttg ccgacccgga tgctttgagc aagttgcagg cggtattgaa ctcgatggtg    28440
ggcggctact acggtggcgg taccaactat gaagacgcgt tcaagaccac gtccaacttc    28500
ttcaacagca ccatgccac cagcaacaaa ggtgcgaga acctgactta cttcattacc    28560
gacggtaagc caacctacta tcagagcaat gagtccacca accctagcct gtggaagaat    28620
```

```
ggcaagagcc tggacgatgt agtcaacgtc aacaattaca agatgggtga cacgttcagc     28680
gcctgggccg acgcgactca caaggtcgag atcagcagca gtggtgtggt caaagtgctg     28740
acttataccg agaaccgccg aggtgagttg gtgctcgact ccaccaagac ggtaggcacc     28800
cttcacgcac agggtgatgg tacctatgaa ttctccagcc tggacggtac cggctacgcg     28860
gattactgga actacgtcta ctcggccgca ggttctactg aaagtttcgc agtattgggc     28920
ggcaccaatg gcttgagcaa agtccaggct atcggcctga acagcgatgt cacgctgaac     28980
gatctgaaac cttac                                                     28995
```

<210> SEQ ID NO 35
<211> LENGTH: 202
<212> TYPE: PRT
<213> ORGANISM: Pseudomonas putida

<400> SEQUENCE: 35

```
Val Leu His Lys Leu Asp Met Gly Gln Phe Lys Asp Gly Leu Arg Arg
1               5                   10                  15

Tyr Phe Lys Gly Ser Asp Ser Leu Gly Gly Gln Pro Leu Pro Glu Val
            20                  25                  30

Asn Lys Ala Leu Ile Glu Asp Ala Pro Arg Val Val Arg Leu Thr Ile
        35                  40                  45

Trp Gly Val Ile Leu Phe Phe Val Phe Leu Ile Val Trp Ala Ser Val
    50                  55                  60

Ala Pro Ile Asp Glu Val Thr Arg Gly Glu Gly Lys Ala Ile Pro Ser
65                  70                  75                  80

Ser Lys Val Gln Lys Ile Gln Asn Leu Glu Gly Gly Ile Val Ala Glu
                85                  90                  95

Ile Phe Ala Lys Glu Gly Gln Ile Val Glu Val Gly Gln Pro Leu Leu
            100                 105                 110

Arg Leu Asp Glu Thr Arg Phe Ala Ser Asn Val Gly Glu Thr Glu Ala
        115                 120                 125

Asp Arg Leu Ala Met Ala Leu Arg Val Glu Arg Leu Ser Ala Glu Val
    130                 135                 140

Glu Asp Arg Pro Leu Ile Ile Asp Glu Lys Leu Arg Lys Ala Ala Pro
145                 150                 155                 160

Asn Gln Ala Ala Ser Glu Glu Ser Leu Tyr Gln Ser Arg Arg Gln Gln
                165                 170                 175

Leu Gln Asp Glu Ile Gly Gly Leu Gln Gln Gln Leu Val Gln Arg Gln
            180                 185                 190

Gln Glu Leu Arg Glu Tyr Ser Ser Lys Arg
        195                 200
```

<210> SEQ ID NO 36
<211> LENGTH: 718
<212> TYPE: PRT
<213> ORGANISM: Pseudomonas putida

<400> SEQUENCE: 36

```
Val Glu Ser Glu Val Ser Arg Val Gln Leu Ser His Asp Pro Arg Ser
1               5                   10                  15

Gln His Asp Asp Pro Leu Leu Asp Ser Leu Leu Ser Leu Cys Val Leu
            20                  25                  30

His Gln Lys Pro Ala Ser Arg Val Met Leu Thr Thr Gly Leu Pro Leu
        35                  40                  45
```

-continued

```
Pro Ala Gln Arg Leu Ser Pro Glu Leu Leu Pro Arg Ala Ala Arg
 50                  55                  60

Ala Gly Leu Gln Gly Arg Leu Leu Gln Arg Lys Leu Glu Gln Ile Pro
 65                  70                  75                  80

Ser Ile Ala Met Pro Ala Met Leu Leu Leu Lys Glu Gly Arg Ser Ala
                 85                  90                  95

Val Leu Leu Gly Trp Glu Asn Asp Thr Ala Arg Leu Leu Leu Ser
                100                 105                 110

Glu Ser Asp Gly Gly Glu Val His Val Ser Arg Glu Ala Leu Leu Ser
                115                 120                 125

Asp Tyr Ser Gly Arg Val Phe Phe Ala Gln Pro Gln His Lys Phe Asp
130                 135                 140

Val Asn His Gly Asn Leu Ile Pro Arg Ala Lys Ser Trp Phe Arg Asp
145                 150                 155                 160

Thr Leu Leu Arg Ser Lys Trp Leu Tyr Ile Asp Ala Ile Ala Ala Ser
                165                 170                 175

Leu Val Ile Asn Leu Ile Ala Leu Ala Ala Pro Leu Phe Val Met Asn
                180                 185                 190

Val Tyr Asp Arg Val Val Pro Asn Gln Ala Thr Ser Thr Leu Trp Val
                195                 200                 205

Leu Ala Ile Gly Ile Ala Gly Ala Tyr Ile Phe Asp Leu Ile Leu Lys
210                 215                 220

Gly Leu Arg Gly Leu Cys Leu Asp Leu Ala Gly Lys Lys Thr Asp Leu
225                 230                 235                 240

Ile Ile Ser Ala Thr Leu Phe Glu Arg Ile Val Gly Met Ser Met Lys
                245                 250                 255

Tyr Arg Pro Ala Arg Val Gly Ser Phe Ala Gln Asn Ile His Glu Phe
                260                 265                 270

Gln Gly Leu Arg Asp Phe Leu Ala Ser Leu Thr Leu Thr Ser Leu Ile
                275                 280                 285

Asp Leu Pro Phe Thr Ile Leu Ile Leu Ile Val Ile Ala Ile Ile Gly
                290                 295                 300

Gly His Leu Val Trp Ile Pro Ile Ile Ala Phe Pro Leu Ala Leu Gly
305                 310                 315                 320

Ile Gly Tyr Ala Leu Gln Arg Pro Leu Met Ala Thr Met Glu Arg Thr
                325                 330                 335

Met Ala Leu Ala Ser Glu Arg Gln Ser Ser Leu Ile Glu Thr Leu Ala
                340                 345                 350

Gly Leu Asp Ala Val Lys Val Asn Asn Ala Glu Ser Glu Arg Gln Tyr
                355                 360                 365

Met Trp Glu Gln Thr Leu Gly Thr Leu Ser Arg Leu Glu Leu Arg Val
370                 375                 380

Lys Val Leu Ser Ser Leu Ala Met Asn Ile Thr Leu Leu Ile Gln Gln
385                 390                 395                 400

Leu Ala Gly Val Ala Met Ile Cys Val Gly Val Tyr Leu Ile Ile Asp
                405                 410                 415

Gly Asn Leu Ser Met Gly Gly Leu Val Ala Cys Tyr Met Leu Ser Gly
                420                 425                 430

Arg Ala Leu Gly Pro Leu Gly Gln Leu Asn Gly Leu Leu Ala Arg Tyr
                435                 440                 445

Gln Gln Ala Lys Val Thr Met Val Ser Thr Asp His Met Met Asp Leu
450                 455                 460

Pro Gln Glu Arg Asn Phe Glu Glu Arg Pro Leu Ser Arg Lys Val Leu
```

```
                465                 470                 475                 480
        Gln Gly Ser Val Glu Phe Arg Gly Val Asp Phe Thr Tyr Pro Asn Gln
                        485                 490                 495

Gln Asn Leu Ala Leu Lys Asn Ile Asn Leu Thr Ile Arg Pro Gly Glu
                        500                 505                 510

Lys Val Gly Ile Ile Gly Arg Ser Gly Lys Ser Leu Ala
                        515                 520                 525

Lys Leu Ile Val Gly Leu Tyr Glu Ala Asp Gly Ser Leu Leu Val
                        530                 535                 540

Asp Gly Val Asp Ile Arg Gln Ile Asp Val Ser Glu Leu Arg His Asn
        545                 550                 555                 560

Ile Gly Tyr Val Pro Gln Asp Ile Gln Leu Leu Ala Gly Thr Leu Arg
                        565                 570                 575

Asp Asn Leu Val Ser Gly Ala Arg Tyr Ile Glu Asp Glu Leu Ile Leu
                        580                 585                 590

Gln Ala Ala Glu Leu Ala Gly Val His Glu Phe Ala Arg Leu His Pro
                        595                 600                 605

Asp Gly Tyr Glu Leu Gln Val Gly Glu Arg Gly Gln Asn Leu Ser Gly
                        610                 615                 620

Gly Gln Arg Gln Asn Val Ala Leu Gly Arg Ala Leu Leu Leu Asn Pro
        625                 630                 635                 640

Gln Ile Leu Leu Leu Asp Glu Pro Thr Ser Ala Met Asp Asn Thr Gly
                        645                 650                 655

Glu Glu Arg Leu Lys Gln Arg Leu Gln Ala Val Val Glu Gly Lys Thr
                        660                 665                 670

Val Leu Leu Val Thr His Arg Ala Ser Leu Leu Ser Leu Val Asp Arg
                        675                 680                 685

Leu Ile Val Ile Asp Arg Gly Gln Ile Val Ala Asp Gly Pro Lys Ala
                        690                 695                 700

Ala Val Met Asp Ala Leu Lys Lys Gly Gln Ile Ser Val Ala
        705                 710                 715

<210> SEQ ID NO 37
<211> LENGTH: 8422
<212> TYPE: PRT
<213> ORGANISM: Pseudomonas putida

<400> SEQUENCE: 37

Met Ser Ser Val Val Ala Ile Val Lys Ser Ile Val Gly Gln Val Ile
        1               5                   10                  15

Ala Val Ser Pro Glu Gly Ile Arg Arg Val Leu Ile Glu Gly Asp Arg
                        20                  25                  30

Leu Leu Ala Gly Glu Glu Val Leu Thr Gly Pro Gly Gly Ala Val Thr
                        35                  40                  45

Leu Glu Leu Ala Asp Gly Arg Leu Leu Asp Leu Gly Arg Asp Ser Gln
                        50                  55                  60

Trp Ser Ala Asp Ala Pro Asp Ser Ser Thr Asp Leu Ser Gln Ala Ala
        65                  70                  75                  80

Ala Gln Ala Ala Pro Ser Val Glu Glu Leu Gln Gln Ala Ile Ala Ala
                        85                  90                  95

Gly Val Asp Pro Thr Thr Glu Leu Glu Ala Thr Ala Ala Gly Pro Ser
                        100                 105                 110

Ser Ala Gly Gly Gly Ala Leu Gly Gly Gly His Ser Phe Val Met Leu
                        115                 120                 125
```

```
Glu Glu Thr Ala Gly Arg Val Asp Thr Thr Val Gly Phe Pro Thr Asp
            130                 135                 140
Gly Leu Gly Phe Ala Gly Val Pro Asp Asn Gln Glu Val Gly Leu Leu
145                 150                 155                 160
Asp Thr Asn Gly Asn Asn Leu Val Thr Pro Thr Asp Thr Thr Val
                165                 170                 175
Ala Thr Glu Leu Thr Leu Gly Ala Thr Pro Ser Ile Ser Glu Ala Gly
            180                 185                 190
Gly Val Ile Val Tyr Thr Ala Thr Val Gly Gln Ala Pro Thr Thr Asn
                195                 200                 205
Leu Val Ile Thr Leu Ser Asn Gly Ala Val Ile Val Pro Ala Gly
210                 215                 220
Gln Thr Ser Gly Ser Val Asn Val Ala Val Pro Ala Asn Asp Thr Pro
225                 230                 235                 240
Tyr Ile Asp Gly Gly Gln Ile Ser Ala Thr Val Thr Gly Ser Thr Gly
                    245                 250                 255
Gly Gly Gly Leu Thr Val Thr Leu Pro Gln Thr Pro Ala Val Thr Gln
                260                 265                 270
Val Thr Asp Thr Ile Asp Thr Thr Ala Thr Leu Thr Ala Ser Pro
            275                 280                 285
Ser Val Thr Glu Gly Gly Val Ile Thr Tyr Thr Val Thr Leu Ser Asn
290                 295                 300
Pro Ala Gln Thr Pro Val Thr Leu Ser Asn Gly Gln Val Ile
305                 310                 315                 320
Thr Val Glu Ala Gly Lys Thr Gln Gly Ser Val Asp Phe Gln Thr Pro
                325                 330                 335
Ala Asn Asp Val Tyr Asn Asn Gly Ser Thr Val Ser Val Thr Ile Glu
            340                 345                 350
Asn Ala Thr Gly Gly Asn Phe Glu Gln Leu Thr Pro Asn Pro Thr Pro
                355                 360                 365
Ala Gln Thr Thr Ile Asn Asp Ser Val Asp Thr Thr Ala Thr Leu
            370                 375                 380
Thr Ala Ser Pro Ser Val Thr Glu Gly Gly Val Ile Thr Tyr Thr Val
385                 390                 395                 400
Thr Leu Ser Asn Pro Ala Gln Thr Pro Val Thr Val Asn Leu Ser Asn
                405                 410                 415
Gly Gln Thr Ile Thr Val Glu Ala Gly Lys Thr Gln Gly Ser Val Asp
                420                 425                 430
Phe Gln Thr Pro Ala Asn Asp Val Tyr Asn Asn Gly Ser Thr Val Ser
            435                 440                 445
Val Thr Ile Glu Ser Ala Thr Gly Gly Asn Phe Glu Gln Leu Thr Pro
450                 455                 460
Asn Pro Thr Pro Ala Gln Thr Thr Ile Asn Asp Ser Val Asp Thr Thr
465                 470                 475                 480
Thr Ala Thr Leu Thr Ala Ser Pro Ser Val Thr Glu Gly Gly Val Ile
                485                 490                 495
Thr Tyr Thr Val Thr Leu Ser Asn Pro Ala Gln Thr Pro Val Thr Val
            500                 505                 510
Thr Leu Ser Asn Gly Gln Thr Ile Thr Val Glu Ala Gly Lys Thr Gln
                515                 520                 525
Gly Ser Val Asp Phe Gln Thr Pro Ala Asn Asp Val Tyr Asn Asn Gly
530                 535                 540
Ser Thr Val Ser Val Thr Ile Glu Asn Ala Thr Gly Gly Asn Phe Glu
```

-continued

```
         545                 550                 555                 560
Gln Leu Thr Pro Asn Pro Thr Pro Ala Gln Thr Thr Ile Asn Asp Ser
                565                 570                 575
Val Asp Thr Thr Thr Ala Thr Leu Thr Ala Ser Pro Ser Val Thr Glu
                580                 585                 590
Gly Gly Val Ile Thr Tyr Thr Val Thr Leu Ser Asn Pro Ala Gln Thr
                595                 600                 605
Pro Val Thr Val Thr Leu Ser Asn Gly Gln Thr Ile Thr Val Glu Ala
    610                 615                 620
Gly Lys Thr Gln Gly Ser Val Asp Phe Gln Thr Pro Ala Asn Asp Val
625                 630                 635                 640
Tyr Asn Asn Gly Ser Thr Val Ser Val Thr Ile Glu Asn Ala Thr Gly
                645                 650                 655
Gly Asn Phe Glu Gln Leu Thr Pro Asn Pro Thr Pro Ala Gln Thr Thr
                660                 665                 670
Ile Asn Asp Ser Val Asp Ala Thr Thr Ala Thr Leu Thr Ala Ser Pro
    675                 680                 685
Ser Val Thr Glu Gly Gly Val Ile Thr Tyr Thr Val Thr Leu Ser Asn
    690                 695                 700
Pro Ala Gln Thr Pro Val Thr Val Thr Leu Ser Asn Gly Gln Thr Ile
705                 710                 715                 720
Thr Val Glu Ala Gly Lys Thr Gln Gly Ser Val Asp Phe Gln Thr Pro
                725                 730                 735
Ala Asn Asp Val Tyr Asn Asn Gly Ser Thr Val Ser Val Thr Ile Glu
                740                 745                 750
Asn Ala Thr Gly Gly Asn Phe Glu Gln Leu Thr Pro Asn Pro Thr Pro
                755                 760                 765
Ala Gln Thr Thr Ile Asn Asp Ser Val Asp Ala Thr Thr Ala Thr Leu
    770                 775                 780
Thr Ala Ser Pro Ser Val Thr Glu Gly Gly Val Ile Thr Tyr Thr Val
785                 790                 795                 800
Thr Leu Ser Asn Pro Ala Gln Thr Pro Val Thr Val Thr Leu Ser Asn
                805                 810                 815
Gly Gln Thr Ile Thr Val Glu Ala Gly Lys Thr Gln Gly Ser Val Asp
                820                 825                 830
Phe Gln Thr Pro Ala Asn Asp Val Tyr Asn Asn Gly Ser Thr Val Ser
    835                 840                 845
Val Thr Ile Glu Asn Ala Thr Gly Gly Asn Phe Glu Gln Leu Thr Pro
    850                 855                 860
Asn Pro Thr Pro Ala Gln Thr Thr Ile Asn Asp Ser Val Asp Ala Thr
865                 870                 875                 880
Thr Ala Thr Leu Thr Ala Ser Pro Ser Val Thr Glu Gly Gly Val Ile
                885                 890                 895
Thr Tyr Thr Val Thr Leu Ser Asn Pro Ala Gln Thr Pro Val Thr Val
                900                 905                 910
Thr Leu Ser Asn Gly Gln Val Ile Thr Val Glu Ala Gly Lys Thr Gln
                915                 920                 925
Gly Ser Val Asp Phe Gln Thr Pro Ala Asn Asp Val Tyr Asn Asn Gly
    930                 935                 940
Ser Thr Val Ser Val Thr Ile Glu Asn Ala Thr Gly Gly Asn Phe Glu
945                 950                 955                 960
Gln Leu Thr Pro Asn Pro Thr Pro Ala Gln Thr Thr Ile Asn Asp Ser
                965                 970                 975
```

-continued

```
Val Asp Ala Thr Thr Ala Thr Leu Thr Ala Ser Pro Ser Val Thr Glu
            980                 985                 990

Gly Gly Val Ile Thr Tyr Thr Val Ile Leu Ser Asn Pro Ala Gln Thr
        995                1000                1005

Pro Val Thr Val Thr Leu Ser Asn Gly Gln Thr Ile Thr Val Glu
    1010                1015                1020

Ala Gly Lys Thr Gln Gly Ser Val Asp Phe Gln Thr Pro Ala Asn
    1025                1030                1035

Asp Val Tyr Asn Asn Gly Ser Thr Val Ser Val Thr Ile Glu Asn
    1040                1045                1050

Ala Thr Gly Gly Asn Phe Glu Gln Leu Thr Pro Asn Pro Thr Pro
    1055                1060                1065

Ala Gln Thr Thr Ile Thr Asp Ser Val Asp Thr Thr Ala Thr
    1070                1075                1080

Leu Thr Ala Ser Pro Ser Val Thr Glu Gly Gly Val Ile Thr Tyr
    1085                1090                1095

Thr Val Thr Leu Ser Asn Pro Ala Gln Thr Pro Val Thr Val Thr
    1100                1105                1110

Leu Ser Asn Gly Gln Thr Ile Thr Val Glu Ala Gly Lys Thr Gln
    1115                1120                1125

Gly Ser Val Asp Phe Gln Thr Pro Ala Asn Asp Val Tyr Asn Asn
    1130                1135                1140

Gly Ser Thr Val Ser Val Thr Ile Glu Ser Ala Thr Gly Gly Asn
    1145                1150                1155

Phe Glu His Leu Thr Pro Asn Pro Thr Pro Ala Ser Thr Val Ile
    1160                1165                1170

Asn Asp Ser Ile Asp Thr Val Thr Val Ser Ile Val Ser Asn Gly
    1175                1180                1185

Asn Val Thr Glu Asp Gln Gln Pro Ser Phe Thr Val Lys Val Ser
    1190                1195                1200

Gln Ala Leu Asp Arg Pro Leu Thr Val Thr Leu Ser Asn Gly Asp
    1205                1210                1215

Thr Val Thr Ile Glu Ala Gly Lys Thr Glu Val Glu Tyr Lys Thr
    1220                1225                1230

Ser Val Gln Gly Asp Asp Val Tyr Leu Asp Ala Gly Ser Ile Thr
    1235                1240                1245

Leu Ser Val Thr Asp Ala Thr Val Pro Gly Ala Thr Phe Glu Lys
    1250                1255                1260

Leu Ala Leu Gly Gly Pro Ala Thr Val Glu Ile Ser Asp Thr Ile
    1265                1270                1275

Ser Glu Val Val Ala Lys Leu Thr Ala Thr Pro Ser Val Thr Glu
    1280                1285                1290

Gly Gly Glu Ile Thr Tyr Thr Ile Thr Leu Thr Asn Lys Asp Gly
    1295                1300                1305

Leu Pro Ile Asn Asn His Ser Glu Leu Tyr Phe Lys Leu Thr Asp
    1310                1315                1320

Gly Thr Thr Val Val Ala Ala Asn Ser Thr Thr Gly Ser Ala
    1325                1330                1335

Thr Val Ala Ala Pro Asp Asn Val Tyr Val Gly Thr Asn Gln Pro
    1340                1345                1350

Val Val Asn Ala Ile Asp Ala Val Ser Gly Ala Asp Ala Trp Lys
    1355                1360                1365
```

-continued

Phe Glu Asn Leu Asn Leu Asp Lys Thr Pro Val Ser Thr Glu Val
1370              1375              1380

Thr Asp Glu Pro Gly Thr Pro Gly Asn Glu Gly Asp Ile Val Lys
1385              1390              1395

Val Thr Ile Thr Ala Asp Gln Thr Ser Val Ala Glu Asn Val Lys
1400              1405              1410

Pro Thr Phe Thr Val His Ile Asn Thr Ala Leu Ala His Asp Leu
1415              1420              1425

Val Val Thr Leu Ser Asn Asn Ala Gln Val Thr Ile Lys Ala Gly
1430              1435              1440

Glu Thr Ser Ala Pro Tyr Thr His Asp Ala Gln Gly Asp Asp Val
1445              1450              1455

Tyr Gln Asp Ala Gly Gln Ile Ser Leu Gly Ile Asn Ser Ala Val
1460              1465              1470

Asp Ala Thr Gly Ala Ala Phe Glu Asn Leu Glu Leu Gly Gly Ala
1475              1480              1485

Ala Lys Val Asp Val Thr Asp Thr Leu Asp Glu Val Val Ala Lys
1490              1495              1500

Leu Thr Ala Thr Pro Ser Val Thr Glu Gly Gly Glu Ile Thr Tyr
1505              1510              1515

Thr Ile Thr Leu Thr Asn Lys Asp Gly Leu Pro Ile Asn Asn His
1520              1525              1530

Ser Glu Leu Tyr Phe Lys Leu Thr Asp Gly Thr Thr Val Val Val
1535              1540              1545

Ala Ala Asn Ser Thr Thr Gly Ser Ala Thr Val Ala Ala Pro Asp
1550              1555              1560

Asn Val Tyr Val Gly Thr Asn Gln Pro Val Val Asn Ala Ile Asp
1565              1570              1575

Ala Val Ser Gly Ala Asp Ala Trp Lys Phe Glu Asn Leu Asn Leu
1580              1585              1590

Asp Lys Thr Pro Val Ser Thr Glu Val Thr Asp Glu Pro Gly Thr
1595              1600              1605

Pro Gly Asn Glu Gly Asp Ile Val Lys Val Thr Ile Thr Ala Asp
1610              1615              1620

Gln Thr Ser Val Ala Glu Asn Val Lys Pro Thr Phe Thr Val His
1625              1630              1635

Val Asn Gln Pro Leu Ala His Asp Leu Val Val Thr Leu Ser Asn
1640              1645              1650

Asn Ala Gln Val Thr Ile Lys Ala Gly Glu Thr Ser Ala Pro Tyr
1655              1660              1665

Thr His Asp Ala Gln Gly Asp Asp Val Tyr Gln Asp Ala Gly Gln
1670              1675              1680

Ile Ser Leu Gly Ile Asn Ser Ala Val Asp Ala Thr Gly Ala Ala
1685              1690              1695

Phe Glu Asn Leu Glu Leu Gly Gly Ala Ala Ser Val Gln Val Thr
1700              1705              1710

Asp Thr Leu Asp Glu Val Val Ala Lys Leu Thr Ala Thr Pro Ser
1715              1720              1725

Val Thr Glu Gly Gly Glu Ile Thr Tyr Thr Ile Thr Leu Thr Asn
1730              1735              1740

Lys Asp Gly Leu Pro Ile Asn Asn His Ser Glu Leu Tyr Phe Lys
1745              1750              1755

Leu Thr Asp Gly Thr Thr Val Val Val Ala Ala Asn Ser Thr Thr

-continued

```
             1760                1765                1770
Gly Ser  Ala Thr  Ala Thr  Ala Pro  Asp Asn  Val Tyr  Val Gly  Thr
         1775                1780                1785

Asn Ala  Pro Val  Ile Asn  Ala Ile  Asp Ala  Val Ser  Gly Ala  Asp
         1790                1795                1800

Ala Trp  Lys Phe  Glu Asn  Leu Asn  Leu Asp  Lys Thr  Pro Val  Ser
         1805                1810                1815

Thr Glu  Val Thr  Asp Glu  Pro Gly  Thr Pro  Gly Asn  Glu Gly  Asp
         1820                1825                1830

Ile Val  Lys Val  Thr Ile  Thr Ala  Asp Gln  Thr Ser  Val Ala  Glu
         1835                1840                1845

Asn Val  Lys Pro  Thr Phe  Thr Val  His Val  Asn Gln  Pro Leu  Ala
         1850                1855                1860

His Asp  Leu Val  Val Thr  Leu Ser  Asn Asn  Ala Gln  Val Thr  Ile
         1865                1870                1875

Lys Ala  Gly Glu  Thr Ser  Ala Pro  Tyr Thr  His Asp  Ala Gln  Gly
         1880                1885                1890

Asp Asp  Val Tyr  Gln Asp  Ala Gly  Gln Ile  Ser Leu  Gly Ile  Asn
         1895                1900                1905

Ser Ala  Val Asp  Ala Thr  Gly Ala  Ala Phe  Glu Asn  Leu Glu  Leu
         1910                1915                1920

Gly Gly  Ser Ala  Ser Val  Gln Val  Thr Asp  Thr Leu  Asp Glu  Val
         1925                1930                1935

Val Ala  Lys Leu  Thr Ala  Thr Pro  Ser Val  Thr Glu  Gly Gly  Glu
         1940                1945                1950

Ile Thr  Tyr Thr  Ile Thr  Leu Thr  Asn Lys  Asp Gly  Leu Pro  Ile
         1955                1960                1965

Asn Asn  His Ser  Glu Leu  Tyr Phe  Lys Leu  Thr Asp  Gly Thr  Thr
         1970                1975                1980

Val Val  Val Ala  Ala Asn  Ser Thr  Thr Gly  Ser Ala  Thr Ala  Thr
         1985                1990                1995

Ala Pro  Asp Asn  Val Tyr  Val Gly  Thr Asn  Ala Pro  Val Val  Asn
         2000                2005                2010

Ala Ile  Asp Ala  Val Ser  Gly Ala  Asp Ala  Trp Lys  Phe Glu  Asn
         2015                2020                2025

Leu Asn  Leu Asp  Lys Thr  Pro Val  Ser Thr  Glu Val  Thr Asp  Glu
         2030                2035                2040

Pro Gly  Thr Pro  Gly Asn  Glu Gly  Asp Ile  Val Lys  Val Thr  Ile
         2045                2050                2055

Thr Ala  Asp Gln  Ala Ser  Val Ala  Glu Asn  Val Lys  Pro Thr  Phe
         2060                2065                2070

Thr Val  His Val  Asn Gln  Pro Leu  Ala His  Asp Leu  Val Val  Thr
         2075                2080                2085

Leu Ser  Asn Asn  Ala Gln  Val Thr  Ile Lys  Ala Gly  Glu Thr  Ser
         2090                2095                2100

Ala Pro  Tyr Thr  His Asp  Ala Gln  Gly Asp  Asp Val  Tyr Gln  Asp
         2105                2110                2115

Ala Gly  Gln Ile  Ser Leu  Gly Ile  Thr Ser  Ala Val  Asp Val  Asp
         2120                2125                2130

Gly His  Thr Phe  Glu Asn  Leu Gln  Leu Gly  Gly Asn  Ala Ser  Val
         2135                2140                2145

Gln Val  Thr Asp  Thr Leu  Asp Glu  Val Val  Ala Lys  Leu Thr  Ala
         2150                2155                2160
```

```
Thr Pro Ser Val Thr Glu Gly Gly Glu Ile Thr Tyr Thr Ile Thr
    2165            2170                2175

Leu Thr Asn Lys Asp Gly Leu Pro Ile Asn Asn His Ser Glu Leu
    2180            2185                2190

Tyr Phe Lys Leu Thr Asp Gly Thr Thr Val Val Val Ala Ala Asn
    2195            2200                2205

Ser Thr Thr Gly Ser Ala Thr Ala Thr Ala Pro Asp Asn Val Tyr
    2210            2215                2220

Val Gly Thr Asn Ala Pro Val Val Asn Ala Ile Asp Ala Val Ser
    2225            2230                2235

Gly Ala Asp Ala Trp Lys Phe Glu Asn Leu Asn Leu Asp Lys Thr
    2240            2245                2250

Pro Val Ser Thr Thr Val Thr Asp Glu Pro Gly Thr Pro Gly Asn
    2255            2260                2265

Glu Gly Asp Ile Val Lys Val Thr Ile Thr Ala Asp Gln Thr Ser
    2270            2275                2280

Val Ala Glu Asn Val Lys Pro Thr Phe Thr Val His Val Asn Gln
    2285            2290                2295

Pro Leu Ala His Asp Leu Ile Val Thr Leu Ser Asn Asn Ala Gln
    2300            2305                2310

Val Thr Ile Lys Ala Gly Glu Thr Ser Ala Pro Tyr Thr His Asp
    2315            2320                2325

Ala Gln Gly Asp Asp Val Tyr Gln Asp Ala Gly Gln Ile Ser Leu
    2330            2335                2340

Gly Ile Asn Ser Ala Val Asp Ala Thr Gly Ala Ala Phe Glu Asn
    2345            2350                2355

Leu Gln Leu Gly Gly Asn Ala Ser Val Gln Val Thr Asp Thr Leu
    2360            2365                2370

Asp Glu Val Val Ala Lys Leu Thr Ala Thr Pro Ser Val Thr Glu
    2375            2380                2385

Gly Gly Glu Ile Thr Tyr Thr Ile Thr Leu Thr Asn Lys Asp Gly
    2390            2395                2400

Leu Pro Ile Asn Asn His Ser Glu Leu Tyr Phe Lys Leu Thr Asp
    2405            2410                2415

Gly Thr Thr Val Val Val Ala Ala Asn Ser Thr Thr Gly Ser Ala
    2420            2425                2430

Thr Val Ala Ala Pro Asp Asn Val Tyr Val Gly Thr Asn Ala Pro
    2435            2440                2445

Val Val Asn Ala Ile Asp Ala Val Ser Gly Ala Asp Ala Trp Lys
    2450            2455                2460

Phe Glu Asn Leu Asn Leu Asp Lys Thr Pro Val Ser Thr Thr Val
    2465            2470                2475

Thr Asp Glu Pro Gly Thr Pro Gly Asn Glu Gly Asp Ile Val Lys
    2480            2485                2490

Val Thr Ile Thr Ala Asp Gln Thr Ser Val Ala Glu Asn Val Lys
    2495            2500                2505

Pro Thr Phe Thr Val His Val Asn Gln Pro Leu Ala His Asp Leu
    2510            2515                2520

Val Val Thr Leu Ser Asn Asn Ala Gln Val Thr Ile Lys Ala Gly
    2525            2530                2535

Glu Thr Ser Ala Pro Tyr Thr His Asp Ala Gln Gly Asp Asp Val
    2540            2545                2550
```

-continued

Tyr Gln Asp Ala Gly Gln Ile Ser Leu Gly Ile Thr Ser Ala Val
2555                     2560                2565

Asp Val Asp Gly His Thr Phe Glu Asn Leu Gln Leu Gly Gly Asn
2570                     2575                2580

Ala Ser Val Gln Val Thr Asp Thr Leu Asp Glu Val Val Ala Lys
2585                     2590                2595

Leu Thr Ala Thr Pro Ser Val Thr Glu Gly Gly Glu Ile Thr Tyr
2600                     2605                2610

Thr Ile Thr Leu Thr Asn Lys Asp Gly Leu Pro Ile Asn Asn His
2615                     2620                2625

Ser Glu Leu Tyr Phe Lys Leu Thr Asp Gly Thr Thr Val Val Val
2630                     2635                2640

Ala Ala Asn Ser Thr Thr Gly Ser Ala Thr Ala Thr Ala Pro Asp
2645                     2650                2655

Asn Val Tyr Val Gly Thr Asn Ala Pro Val Val Asn Ala Ile Asp
2660                     2665                2670

Ala Val Ser Gly Ala Asp Ala Trp Lys Phe Glu Asn Leu Asn Leu
2675                     2680                2685

Asp Lys Thr Pro Val Ser Thr Glu Val Thr Asp Glu Pro Gly Thr
2690                     2695                2700

Pro Gly Asn Glu Gly Asp Ile Val Lys Val Thr Ile Thr Ala Asp
2705                     2710                2715

Gln Thr Ser Val Ala Glu Asn Val Lys Pro Thr Phe Thr Val His
2720                     2725                2730

Ile Asn Thr Ala Leu Ala His Asp Leu Val Val Thr Leu Ser Asn
2735                     2740                2745

Asn Ala Gln Val Thr Ile Lys Ala Gly Glu Thr Ser Ala Pro Tyr
2750                     2755                2760

Thr His Ala Ala Gln Gly Asp Asp Val Tyr Asn Asp Ala Gly Gln
2765                     2770                2775

Ile Ser Leu Gly Ile Thr Ser Ala Val Asp Ala Thr Gly Ala Thr
2780                     2785                2790

Phe Glu Asn Leu Ala Leu Gly Gly Ala Ala Lys Val Asp Val Thr
2795                     2800                2805

Asp Thr Thr Asp Glu Val Val Ala Lys Leu Thr Ala Thr Pro Ser
2810                     2815                2820

Val Thr Glu Gly Gly Glu Ile Thr Tyr Thr Ile Thr Leu Thr Asn
2825                     2830                2835

Lys Asp Gly Leu Pro Ile Asn Asn His Ser Ala Leu Thr Phe Thr
2840                     2845                2850

Leu Ser Asp Gly Lys Thr Val Ile Thr Val Pro Ala Asn Gly Thr
2855                     2860                2865

Val Gly Thr Ala Thr Val Thr Ala Pro Asp Asn Val Tyr Val Gly
2870                     2875                2880

Thr Asn Asp Pro Val Ile Lys Ser Ile Ala Thr Val Glu Gly Ala
2885                     2890                2895

Asp Val Gly Lys Phe Glu Gln Leu Thr Leu Asp Lys Thr Pro Val
2900                     2905                2910

Ser Thr Ser Val Thr Asp Glu Pro Gly Thr Pro Gly Asn Glu Gly
2915                     2920                2925

Asp Leu Val Lys Val Thr Ile Thr Ala Asp Gln Thr Ser Val Ala
2930                     2935                2940

Glu Asn Val Lys Pro Thr Phe Thr Val His Val Asn Gln Pro Leu

```
                    2945                2950                2955
Ala His Asp Leu Val Val Thr Leu Ser Asn Asn Ala Gln Val Thr
        2960                2965                2970
Ile Lys Ala Gly Glu Thr Ser Ala Pro Tyr Thr His Ala Ala Gln
        2975                2980                2985
Gly Asp Asp Val Tyr Asn Asp Ala Gly Gln Ile Ser Leu Gly Ile
        2990                2995                3000
Thr Ser Ala Val Asp Ala Thr Gly Ala Thr Phe Glu Asn Leu Glu
        3005                3010                3015
Leu Gly Gly Ala Ala Lys Val Asp Val Thr Asp Thr Thr Asp Glu
        3020                3025                3030
Val Val Ala Lys Leu Thr Ala Thr Pro Ser Val Thr Glu Gly Gly
        3035                3040                3045
Glu Ile Thr Tyr Thr Ile Thr Leu Thr Asn Lys Asp Gly Leu Pro
        3050                3055                3060
Ile Asn Asn His Ser Ala Leu Thr Phe Thr Leu Ser Asp Gly Lys
        3065                3070                3075
Thr Val Ile Thr Val Pro Ala Asn Gly Thr Val Gly Thr Ala Thr
        3080                3085                3090
Val Thr Ala Pro Asp Asn Val Tyr Val Gly Thr Asn Asp Pro Val
        3095                3100                3105
Ile Lys Ser Ile Ala Thr Val Glu Gly Ala Asp Val Gly Lys Phe
        3110                3115                3120
Glu Gln Leu Thr Leu Asp Lys Thr Pro Val Ser Thr Thr Val Thr
        3125                3130                3135
Asp Glu Pro Gly Thr Pro Gly Asn Pro Gly Gly Ser Asn Glu Gly
        3140                3145                3150
Asp Leu Val Lys Val Thr Ile Thr Ala Asp Gln Thr Ser Val Ala
        3155                3160                3165
Glu Asn Val Lys Pro Thr Phe Thr Val His Val Asn Gln Pro Leu
        3170                3175                3180
Ala His Asp Leu Val Val Thr Leu Ser Asn Asn Ala Gln Val Thr
        3185                3190                3195
Ile Lys Ala Gly Glu Thr Ser Ala Pro Tyr Thr His Ala Ala Gln
        3200                3205                3210
Gly Asp Asp Val Tyr Asn Asp Ala Gly Gln Ile Ser Leu Gly Ile
        3215                3220                3225
Asn Ser Ala Val Asp Ala Thr Gly Ala Thr Phe Glu Asn Leu Glu
        3230                3235                3240
Leu Gly Gly Ala Ala Lys Val Asp Val Thr Asp Thr Thr Asp Glu
        3245                3250                3255
Val Val Ala Lys Leu Thr Ala Thr Pro Ser Val Thr Glu Gly Gly
        3260                3265                3270
Glu Ile Thr Tyr Thr Ile Thr Leu Thr Asn Lys Asp Gly Leu Pro
        3275                3280                3285
Ile Asn Asn His Ser Ala Leu Thr Phe Thr Leu Ser Asp Gly Lys
        3290                3295                3300
Thr Val Ile Thr Val Pro Ala Asn Gly Thr Val Gly Thr Ala Thr
        3305                3310                3315
Val Thr Ala Pro Asp Asn Val Tyr Val Gly Thr Asn Asp Pro Val
        3320                3325                3330
Ile Lys Ser Ile Ala Thr Val Glu Gly Ala Asp Val Gly Lys Phe
        3335                3340                3345
```

```
Glu Gln Leu Thr Leu Asp Lys Thr Pro Val Ser Thr Thr Val Thr
    3350                3355                3360

Asp Glu Pro Gly Thr Pro Gly Asn Pro Gly Gly Ser Asn Glu Gly
    3365                3370                3375

Asp Leu Val Lys Val Thr Ile Thr Ala Asp Gln Thr Ser Val Ala
    3380                3385                3390

Glu Asn Val Lys Pro Thr Phe Thr Val His Val Asn Gln Pro Leu
    3395                3400                3405

Ala His Asp Leu Val Val Thr Leu Ser Asn Asn Ala Gln Val Thr
    3410                3415                3420

Ile Lys Ala Gly Glu Thr Ser Ala Pro Tyr Thr His Ala Ala Gln
    3425                3430                3435

Gly Asp Asp Val Tyr Asn Asp Ala Gly Gln Ile Ser Leu Gly Ile
    3440                3445                3450

Thr Ser Ala Val Asp Val Asp Gly Arg Thr Phe Glu Asn Leu Glu
    3455                3460                3465

Leu Gly Gly Ala Ala Ser Val Gln Val Thr Asp Thr Thr Asp Glu
    3470                3475                3480

Val Val Ala Lys Leu Thr Ala Thr Pro Ser Val Thr Glu Gly Gly
    3485                3490                3495

Glu Ile Thr Tyr Thr Ile Thr Leu Thr Asn Lys Asp Gly Leu Pro
    3500                3505                3510

Ile Asn Asn His Ser Ala Leu Thr Phe Thr Leu Ser Asp Gly Lys
    3515                3520                3525

Thr Val Ile Thr Val Pro Ala Asn Gly Thr Val Gly Thr Ala Thr
    3530                3535                3540

Val Thr Ala Pro Asp Asn Val Tyr Val Gly Thr Asn Asp Pro Val
    3545                3550                3555

Ile Lys Ser Ile Ala Thr Val Glu Gly Ala Asp Val Gly Lys Phe
    3560                3565                3570

Glu Gln Leu Thr Leu Asp Lys Thr Pro Val Ser Thr Thr Val Thr
    3575                3580                3585

Asp Glu Pro Gly Thr Pro Gly Asn Pro Gly Gly Ser Asn Glu Gly
    3590                3595                3600

Asp Leu Val Lys Val Thr Ile Thr Ala Asp Gln Thr Ser Val Ala
    3605                3610                3615

Glu Asn Val Lys Pro Thr Phe Thr Val His Val Asn Gln Pro Leu
    3620                3625                3630

Ala His Asp Leu Val Val Thr Leu Ser Asn Asn Ala Gln Val Thr
    3635                3640                3645

Ile Lys Ala Gly Glu Thr Ser Ala Pro Tyr Thr His Ala Ala Gln
    3650                3655                3660

Gly Asp Asp Val Tyr Asn Asp Ala Gly Gln Ile Ser Leu Gly Ile
    3665                3670                3675

Asn Ser Ala Val Asp Ala Thr Gly Ala Thr Phe Glu Asn Leu Gln
    3680                3685                3690

Leu Gly Gly Asn Ala Ser Val Gln Val Thr Asp Thr Thr Asp Glu
    3695                3700                3705

Val Val Ala Lys Leu Thr Ala Thr Pro Ser Val Thr Glu Gly Gly
    3710                3715                3720

Glu Ile Thr Tyr Thr Ile Thr Leu Thr Asn Lys Asp Gly Leu Pro
    3725                3730                3735
```

```
Ile  Asn  Asn  His  Ser  Ala  Leu  Thr  Phe  Thr  Leu  Ser  Asp  Gly  Lys
3740                3745                3750

Thr  Val  Ile  Thr  Val  Pro  Ala  Asn  Gly  Thr  Val  Gly  Thr  Ala  Thr
3755                3760                3765

Val  Thr  Ala  Pro  Asp  Asn  Val  Tyr  Val  Gly  Thr  Asn  Asp  Pro  Val
3770                3775                3780

Ile  Lys  Ser  Ile  Ala  Thr  Val  Glu  Gly  Ala  Asp  Val  Gly  Lys  Phe
3785                3790                3795

Glu  Gln  Leu  Thr  Leu  Asp  Lys  Thr  Pro  Val  Ser  Thr  Ser  Val  Thr
3800                3805                3810

Asp  Glu  Pro  Gly  Thr  Pro  Gly  Asn  Glu  Gly  Asp  Leu  Val  Lys  Val
3815                3820                3825

Thr  Ile  Thr  Ala  Asp  Gln  Thr  Ser  Val  Ala  Glu  Asn  Val  Lys  Pro
3830                3835                3840

Ile  Phe  Thr  Val  His  Val  Asn  Gln  Pro  Leu  Ala  His  Asp  Leu  Val
3845                3850                3855

Val  Thr  Leu  Ser  Asn  Asn  Ala  Gln  Val  Thr  Ile  Lys  Ala  Gly  Glu
3860                3865                3870

Thr  Ser  Ala  Pro  Tyr  Thr  His  Ala  Ala  Gln  Gly  Asp  Asp  Val  Tyr
3875                3880                3885

Asn  Asp  Ala  Gly  Gln  Ile  Ser  Leu  Gly  Ile  Thr  Ser  Ala  Val  Asp
3890                3895                3900

Val  Asp  Gly  Arg  Thr  Phe  Glu  Asn  Leu  Gln  Leu  Gly  Gly  Asn  Ala
3905                3910                3915

Ser  Val  Gln  Val  Thr  Asp  Thr  Thr  Asp  Glu  Val  Val  Ala  Lys  Leu
3920                3925                3930

Thr  Ala  Thr  Pro  Ser  Val  Thr  Glu  Gly  Gly  Glu  Ile  Thr  Tyr  Thr
3935                3940                3945

Ile  Thr  Leu  Thr  Asn  Lys  Asp  Gly  Leu  Pro  Ile  Asn  Asn  His  Ser
3950                3955                3960

Ala  Leu  Thr  Phe  Thr  Leu  Ser  Asp  Gly  Lys  Thr  Val  Ile  Thr  Val
3965                3970                3975

Pro  Ala  Asn  Gly  Thr  Val  Gly  Thr  Ala  Thr  Val  Thr  Ala  Pro  Asp
3980                3985                3990

Asn  Val  Tyr  Val  Gly  Thr  Asn  Asp  Pro  Val  Val  Met  Ser  Ile  Ala
3995                4000                4005

Thr  Val  Gly  Gly  Ala  Asp  Val  Gly  Lys  Phe  Glu  Gln  Leu  Thr  Leu
4010                4015                4020

Asp  Lys  Thr  Pro  Val  Ser  Thr  Val  Thr  Asp  Glu  Pro  Gly  Thr
4025                4030                4035

Pro  Gly  Asn  Pro  Gly  Gly  Ser  Asn  Glu  Gly  Asp  Leu  Val  Lys  Val
4040                4045                4050

Thr  Ile  Thr  Ala  Asp  Gln  Thr  Ser  Val  Ala  Glu  Asn  Val  Lys  Pro
4055                4060                4065

Thr  Phe  Thr  Val  His  Val  Asn  Gln  Pro  Leu  Ala  His  Asp  Leu  Val
4070                4075                4080

Val  Thr  Leu  Ser  Asn  Asn  Ala  Gln  Val  Thr  Ile  Lys  Ala  Gly  Glu
4085                4090                4095

Thr  Ser  Ala  Pro  Tyr  Thr  His  Ala  Ala  Gln  Gly  Asp  Asp  Val  Tyr
4100                4105                4110

Asn  Asp  Ala  Gly  Gln  Ile  Ser  Leu  Gly  Ile  Asn  Ser  Ala  Val  Asp
4115                4120                4125

Ala  Thr  Gly  Ala  Thr  Phe  Glu  Asn  Leu  Ala  Leu  Gly  Gly  Ala  Ala
```

-continued

```
            4130            4135            4140
Lys Val Asp Val Thr Asp Thr Thr Asp Glu Val Val Ala Lys Leu
    4145            4150            4155
Thr Ala Thr Pro Ser Val Thr Glu Gly Gly Glu Ile Thr Tyr Thr
    4160            4165            4170
Ile Thr Leu Thr Asn Lys Asp Gly Leu Pro Ile Asn Asn His Ser
    4175            4180            4185
Ala Leu Thr Phe Thr Leu Ser Asp Gly Lys Thr Val Ile Thr Val
    4190            4195            4200
Pro Ala Asn Gly Thr Val Gly Thr Ala Thr Val Thr Ala Pro Asp
    4205            4210            4215
Asn Val Tyr Val Gly Thr Asn Asp Pro Val Ile Lys Ser Ile Ala
    4220            4225            4230
Thr Val Glu Gly Ala Asp Val Gly Lys Phe Glu Gln Leu Thr Leu
    4235            4240            4245
Asp Lys Thr Pro Val Ser Thr Ser Val Thr Asp Glu Pro Gly Thr
    4250            4255            4260
Pro Gly Asn Glu Gly Asp Leu Val Lys Val Thr Ile Thr Ala Asp
    4265            4270            4275
Gln Thr Ser Val Ala Glu Asn Val Lys Pro Thr Phe Thr Val His
    4280            4285            4290
Val Asn Gln Pro Leu Ala His Asp Leu Val Val Thr Leu Ser Asn
    4295            4300            4305
Asn Ala Gln Val Thr Ile Lys Ala Gly Glu Thr Ser Ala Pro Tyr
    4310            4315            4320
Thr His Ala Ala Gln Gly Asp Asp Val Tyr Asn Asp Ala Gly Gln
    4325            4330            4335
Ile Ser Leu Gly Ile Thr Ser Ala Val Asp Val Asp Gly Arg Thr
    4340            4345            4350
Phe Glu Asn Leu Gln Leu Gly Gly Ala Ala Thr Val Gln Val Thr
    4355            4360            4365
Asp Thr Thr Asp Glu Val Val Ala Lys Leu Thr Ala Thr Pro Ser
    4370            4375            4380
Val Thr Glu Gly Gly Glu Ile Thr Tyr Thr Ile Thr Leu Thr Asn
    4385            4390            4395
Lys Asp Gly Leu Pro Ile Asn Asn His Ser Ala Leu Thr Phe Thr
    4400            4405            4410
Leu Ser Asp Gly Lys Thr Val Ile Thr Val Pro Ala Asn Gly Thr
    4415            4420            4425
Val Gly Thr Ala Thr Val Thr Ala Pro Asp Asn Val Tyr Val Gly
    4430            4435            4440
Thr Asn Asp Pro Val Ile Lys Ser Ile Ala Thr Val Glu Gly Ala
    4445            4450            4455
Asp Val Gly Lys Phe Glu Gln Leu Thr Leu Asp Lys Thr Pro Val
    4460            4465            4470
Ser Thr Ser Val Thr Asp Glu Pro Gly Thr Pro Gly Asn Glu Gly
    4475            4480            4485
Asp Leu Val Lys Val Thr Ile Thr Ala Asp Gln Thr Ser Val Ala
    4490            4495            4500
Glu Asn Val Lys Pro Thr Phe Thr Val His Val Asn Gln Pro Leu
    4505            4510            4515
Ala His Asp Leu Val Val Thr Leu Ser Asn Asn Ala Gln Val Thr
    4520            4525            4530
```

```
Ile Lys Ala Gly Glu Thr Ser Ala Pro Tyr Thr His Ala Ala Gln
    4535            4540            4545

Gly Asp Asp Val Tyr Asn Asp Ala Gly Gln Ile Ser Leu Gly Ile
    4550            4555            4560

Asn Ser Ala Val Asp Ala Thr Gly Ala Thr Phe Glu Asn Leu Gln
    4565            4570            4575

Leu Gly Gly Ala Ala Thr Val Gln Val Thr Asp Thr Thr Asp Glu
    4580            4585            4590

Val Val Ala Lys Leu Thr Ala Thr Pro Ser Val Thr Glu Gly Gly
    4595            4600            4605

Glu Ile Thr Tyr Thr Ile Thr Leu Thr Asn Lys Asp Gly Leu Pro
    4610            4615            4620

Ile Asn Asn His Ser Ala Leu Thr Phe Thr Leu Ser Asp Gly Lys
    4625            4630            4635

Thr Val Ile Thr Val Pro Ala Asn Gly Thr Val Gly Thr Ala Thr
    4640            4645            4650

Val Thr Ala Pro Asp Asn Val Tyr Val Gly Thr Asn Asp Pro Val
    4655            4660            4665

Val Met Ser Ile Ala Thr Val Gly Gly Ala Asp Val Gly Lys Phe
    4670            4675            4680

Glu Gln Leu Thr Leu Asp Lys Thr Pro Val Ser Thr Ser Val Thr
    4685            4690            4695

Asp Glu Pro Gly Thr Pro Gly Asn Glu Gly Asp Leu Val Lys Val
    4700            4705            4710

Thr Ile Thr Ala Asp Gln Thr Ser Val Ala Glu Asn Val Lys Pro
    4715            4720            4725

Thr Phe Thr Val His Val Asn Gln Pro Leu Ala His Asp Leu Val
    4730            4735            4740

Val Thr Leu Ser Asn Asn Ala Gln Val Thr Ile Lys Ala Gly Glu
    4745            4750            4755

Thr Ser Ala Pro Tyr Thr His Ala Ala Gln Gly Asp Asp Val Tyr
    4760            4765            4770

Asn Asp Ala Gly Gln Ile Ser Leu Gly Ile Asn Ser Ala Val Asp
    4775            4780            4785

Ala Thr Gly Ala Thr Phe Glu Asn Leu Glu Leu Gly Gly Ala Ala
    4790            4795            4800

Lys Val Asp Val Thr Asp Thr Thr Asp Glu Val Val Ala Lys Leu
    4805            4810            4815

Thr Ala Thr Pro Ser Val Thr Glu Gly Gly Glu Ile Thr Tyr Thr
    4820            4825            4830

Ile Thr Leu Thr Asn Lys Asp Gly Leu Pro Ile Asp Lys His Ala
    4835            4840            4845

Ala Leu Thr Phe Thr Leu Asp Gly Lys Thr Thr Ile Thr Ile
    4850            4855            4860

Pro Ala Asn Gly Thr Thr Gly Thr Ala Thr Val Thr Ala Pro Asp
    4865            4870            4875

Asn Val Tyr Val Gly Thr Asn Asp Pro Val Val Met Ser Ile Ala
    4880            4885            4890

Thr Val Gly Gly Ala Asp Val Gly Lys Phe Glu Gln Leu Thr Leu
    4895            4900            4905

Asp Lys Thr Pro Val Ser Thr Ser Val Thr Asp Glu Pro Gly Thr
    4910            4915            4920
```

```
Pro Gly Asn Glu Gly Asp Leu Val Lys Val Thr Ile Thr Ala Asp
    4925              4930                4935
Gln Thr Ser Val Ala Glu Asn Val Lys Pro Thr Phe Thr Val His
    4940              4945                4950
Val Asn Gln Pro Leu Ala His Asp Leu Val Val Thr Leu Ser Asn
    4955              4960                4965
Asn Ala Gln Val Thr Ile Lys Ala Gly Glu Thr Ser Ala Pro Tyr
    4970              4975                4980
Thr His Ala Ala Gln Gly Asp Asp Val Tyr Asn Asp Ala Gly Gln
    4985              4990                4995
Ile Ser Leu Gly Ile Thr Ser Ala Val Asp Val Asp Gly Arg Thr
    5000              5005                5010
Phe Glu Asn Leu Glu Leu Gly Gly Ala Ala Ser Val Gln Val Thr
    5015              5020                5025
Asp Thr Leu Asp Glu Val Val Ala Lys Leu Thr Ala Thr Pro Ser
    5030              5035                5040
Val Thr Glu Gly Gly Glu Ile Thr Tyr Thr Ile Thr Leu Thr Asn
    5045              5050                5055
Lys Asp Gly Leu Pro Ile Asn Asn His Ser Ala Leu Thr Phe Thr
    5060              5065                5070
Leu Ser Asp Gly Lys Thr Val Ile Thr Val Pro Ala Asn Gly Thr
    5075              5080                5085
Val Gly Thr Ala Thr Val Thr Ala Pro Asp Asn Val Tyr Val Gly
    5090              5095                5100
Ala Asn Asp Pro Val Val Met Ser Ile Ala Thr Val Glu Gly Ala
    5105              5110                5115
Asp Val Gly Lys Phe Glu Gln Leu Thr Leu Asp Lys Thr Pro Val
    5120              5125                5130
Ser Thr Ser Val Thr Asp Glu Pro Gly Thr Pro Gly Asn Glu Gly
    5135              5140                5145
Asp Leu Val Lys Val Thr Ile Thr Ala Asp Gln Thr Ser Val Ala
    5150              5155                5160
Glu Asn Val Lys Pro Thr Phe Thr Val His Val Asn Gln Pro Leu
    5165              5170                5175
Ala His Asp Leu Val Val Thr Leu Ser Asn Asn Ala Gln Val Thr
    5180              5185                5190
Ile Lys Ala Gly Glu Thr Ser Ala Pro Tyr Thr His Ala Ala Gln
    5195              5200                5205
Gly Asp Asp Val Tyr Asn Asp Ala Gly Gln Ile Ser Leu Gly Ile
    5210              5215                5220
Thr Ser Ala Val Asp Ala Thr Gly Ala Thr Phe Glu Asn Leu Glu
    5225              5230                5235
Leu Gly Gly Ala Ala Ser Val Gln Val Thr Asp Thr Thr Asp Glu
    5240              5245                5250
Val Val Ala Lys Leu Thr Ala Thr Pro Ser Val Thr Glu Gly Gly
    5255              5260                5265
Glu Ile Thr Tyr Thr Ile Thr Leu Thr Asn Lys Asp Gly Leu Pro
    5270              5275                5280
Ile Asn Asn His Ser Ala Leu Thr Phe Thr Leu Ser Asp Gly Lys
    5285              5290                5295
Thr Val Ile Thr Val Pro Ala Asn Gly Thr Val Gly Thr Ala Thr
    5300              5305                5310
Val Thr Ala Pro Asp Asn Val Tyr Val Gly Ser Asn Asp Pro Val
```

```
                    5315               5320                    5325
Val Met Ser Ile Ala Thr Val Gly Gly Ala Asp Val  Gly Lys Phe
        5330                    5335                    5340

Glu Gln Leu Thr Leu Asp Lys Thr Pro Val Ser Thr  Ser Val Thr
        5345                    5350                    5355

Asp Glu Pro Gly Thr Pro Gly Asn Glu Gly Asp Leu  Val Lys Val
        5360                    5365                    5370

Thr Ile Thr Ala Asp Gln Thr Ser Val Ala Glu Asn  Val Lys Pro
        5375                    5380                    5385

Thr Phe Thr Val His Val Asn Gln Pro Leu Ala His  Asp Leu Val
        5390                    5395                    5400

Val Thr Leu Ser Asn Asn Ala Gln Val Thr Ile Lys  Ala Gly Glu
        5405                    5410                    5415

Thr Ser Ala Pro Tyr Thr His Ala Ala Gln Gly Asp  Asp Val Tyr
        5420                    5425                    5430

Asn Asp Ala Gly Gln Ile Ser Leu Gly Ile Asn Ser  Ala Val Asp
        5435                    5440                    5445

Ala Thr Gly Ala Thr Phe Glu Asn Leu Gln Leu Gly  Gly Asn Ala
        5450                    5455                    5460

Ser Val Gln Val Thr Asp Thr Thr Asp Glu Val Val  Ala Lys Leu
        5465                    5470                    5475

Thr Ala Thr Pro Ser Val Thr Glu Gly Gly Glu Ile  Thr Tyr Thr
        5480                    5485                    5490

Ile Thr Leu Thr Asn Lys Asp Gly Leu Pro Ile Asn  Asn His Ser
        5495                    5500                    5505

Ala Leu Thr Phe Thr Leu Ser Asp Gly Lys Thr Val  Ile Thr Val
        5510                    5515                    5520

Pro Ala Asn Gly Thr Val Gly Thr Ala Thr Val Thr  Ala Pro Asp
        5525                    5530                    5535

Asn Val Tyr Val Gly Thr Asn Asp Pro Val Val Met  Ser Ile Ala
        5540                    5545                    5550

Thr Val Gly Gly Ala Asp Val Gly Lys Phe Glu Gln  Leu Thr Leu
        5555                    5560                    5565

Asp Lys Thr Pro Val Ser Thr Thr Val Thr Asp Glu  Pro Gly Thr
        5570                    5575                    5580

Pro Gly Asn Pro Gly Gly Ser Asn Glu Gly Asp Leu  Val Lys Val
        5585                    5590                    5595

Thr Ile Thr Ala Asp Gln Thr Ser Leu Ala Glu Asn  Val Lys Pro
        5600                    5605                    5610

Thr Phe Thr Val His Val Asn Gln Pro Leu Ala His  Asp Leu Val
        5615                    5620                    5625

Val Thr Leu Ser Asn Asn Ala Gln Val Thr Ile Lys  Ala Gly Glu
        5630                    5635                    5640

Thr Ser Ala Pro Tyr Thr His Ala Ala Gln Gly Asp  Asp Val Tyr
        5645                    5650                    5655

Asn Asp Ala Gly Gln Ile Ser Leu Gly Ile Asn Ser  Ala Val Asp
        5660                    5665                    5670

Ala Thr Gly Ala Thr Phe Glu Asn Leu Glu Leu Gly  Gly Ala Ala
        5675                    5680                    5685

Ser Val Gln Val Thr Asp Thr Asp Glu Val Val  Ala Lys Leu
        5690                    5695                    5700

Thr Ala Thr Pro Ser Val Thr Glu Gly Gly Glu Ile  Thr Tyr Thr
        5705                    5710                    5715
```

```
Ile Thr Leu Thr Asn Lys Asp Gly Leu Pro Ile Asn Asn His Ser
    5720            5725            5730

Ala Leu Thr Phe Thr Leu Ser Asp Gly Lys Thr Val Ile Thr Val
    5735            5740            5745

Pro Ala Asn Gly Thr Val Gly Thr Ala Thr Val Thr Ala Pro Asp
    5750            5755            5760

Asn Val Tyr Val Gly Ser Asn Asp Pro Val Val Met Ser Ile Ala
    5765            5770            5775

Thr Val Gly Gly Ala Asp Val Gly Lys Phe Glu Gln Leu Thr Leu
    5780            5785            5790

Asp Lys Thr Pro Val Ser Thr Ser Val Thr Asp Glu Pro Gly Thr
    5795            5800            5805

Pro Gly Asn Glu Gly Asp Leu Val Lys Val Thr Ile Thr Ala Asp
    5810            5815            5820

Gln Thr Ser Val Ala Glu Asn Val Lys Pro Thr Phe Thr Val His
    5825            5830            5835

Val Asn Gln Pro Leu Ala His Asp Leu Val Val Thr Leu Ser Asn
    5840            5845            5850

Asn Ala Gln Val Thr Ile Lys Ala Gly Glu Thr Ser Ala Pro Tyr
    5855            5860            5865

Thr His Ala Ala Gln Gly Asp Asp Val Tyr Asn Asp Ala Gly Gln
    5870            5875            5880

Ile Ser Leu Gly Ile Asn Ser Ala Val Asp Ala Thr Gly Ala Thr
    5885            5890            5895

Phe Glu Asn Leu Glu Leu Gly Gly Ala Ala Ser Val Gln Val Thr
    5900            5905            5910

Asp Thr Thr Asp Glu Val Val Ala Lys Leu Thr Ala Thr Pro Ser
    5915            5920            5925

Val Thr Glu Gly Gly Glu Ile Thr Tyr Thr Ile Thr Leu Thr Asn
    5930            5935            5940

Lys Asp Gly Leu Pro Ile Asn Asn His Ser Ala Leu Thr Phe Thr
    5945            5950            5955

Leu Ser Asp Gly Lys Thr Val Ile Thr Val Pro Ala Asn Gly Thr
    5960            5965            5970

Val Gly Thr Ala Thr Val Thr Ala Pro Asp Asn Val Tyr Val Gly
    5975            5980            5985

Ser Asn Asp Pro Val Val Met Ser Ile Ala Thr Val Gly Gly Ala
    5990            5995            6000

Asp Val Gly Lys Phe Glu Gln Leu Thr Leu Asp Lys Thr Pro Val
    6005            6010            6015

Ser Thr Ser Val Thr Asp Glu Pro Gly Thr Pro Gly Asn Glu Gly
    6020            6025            6030

Asp Leu Val Lys Val Thr Ile Thr Ala Asp Gln Thr Ser Val Ala
    6035            6040            6045

Glu Asn Val Lys Pro Thr Phe Thr Val His Val Asn Gln Pro Leu
    6050            6055            6060

Ala His Asp Leu Val Val Thr Leu Ser Asn Asn Ala Gln Val Thr
    6065            6070            6075

Ile Lys Ala Gly Glu Thr Ser Ala Pro Tyr Thr His Ala Ala Gln
    6080            6085            6090

Gly Asp Asp Val Tyr Asn Asp Ala Gly Gln Ile Ser Leu Gly Ile
    6095            6100            6105
```

```
Asn Ser Ala Val Asp Ala Thr Gly Ala Thr Phe Glu Asn Leu Glu
    6110                6115                6120

Leu Gly Gly Ala Ala Lys Val Asp Val Thr Asp Thr Thr Asp Glu
    6125                6130                6135

Val Val Ala Lys Leu Thr Ala Thr Pro Ser Val Thr Glu Gly Gly
    6140                6145                6150

Glu Ile Thr Tyr Thr Ile Thr Leu Thr Asn Lys Asp Gly Leu Pro
    6155                6160                6165

Ile Asn Asn His Ser Ala Leu Thr Phe Thr Leu Ser Asp Gly Lys
    6170                6175                6180

Thr Val Ile Thr Val Pro Ala Asn Gly Thr Val Gly Thr Ala Thr
    6185                6190                6195

Val Thr Ala Pro Asp Asn Val Tyr Val Gly Thr Asn Asp Pro Val
    6200                6205                6210

Val Met Ser Ile Ala Thr Val Glu Gly Ala Asp Val Gly Lys Phe
    6215                6220                6225

Glu Gln Leu Thr Leu Asp Lys Thr Pro Val Ser Thr Ser Val Thr
    6230                6235                6240

Asp Glu Pro Gly Thr Pro Gly Asn Glu Gly Asp Leu Val Lys Val
    6245                6250                6255

Thr Ile Thr Ala Asp Gln Thr Ser Val Ala Glu Asn Val Lys Pro
    6260                6265                6270

Thr Phe Thr Val His Ile Asn Thr Ala Leu Ala His Asp Leu Val
    6275                6280                6285

Val Thr Leu Ser Asn Asn Ala Gln Val Ile Ile Lys Ala Gly Glu
    6290                6295                6300

Thr Ser Ala Pro Tyr Thr His Ala Ala Gln Gly Asp Asp Val Tyr
    6305                6310                6315

Asn Asp Ala Gly Gln Ile Ser Leu Gly Ile Asn Ser Ala Val Asp
    6320                6325                6330

Ala Thr Gly Ala Thr Phe Glu Asn Leu Gln Leu Gly Gly Asn Ala
    6335                6340                6345

Ser Val Gln Val Thr Asp Thr Thr Asp Glu Val Val Ala Lys Leu
    6350                6355                6360

Thr Ala Thr Pro Ser Val Thr Glu Gly Gly Glu Ile Thr Tyr Thr
    6365                6370                6375

Ile Thr Leu Thr Asn Lys Asp Gly Leu Pro Ile Asn Asn His Ser
    6380                6385                6390

Ala Leu Thr Phe Thr Leu Ser Asp Gly Lys Thr Val Ile Thr Val
    6395                6400                6405

Pro Ala Asn Gly Thr Val Gly Thr Ala Thr Val Thr Ala Pro Asp
    6410                6415                6420

Asn Val Tyr Val Gly Thr Asn Asp Pro Val Val Met Ser Ile Ala
    6425                6430                6435

Thr Val Glu Gly Ala Asp Val Gly Lys Phe Glu Gln Leu Thr Leu
    6440                6445                6450

Asp Lys Thr Pro Val Ser Thr Ser Val Thr Asp Glu Pro Gly Thr
    6455                6460                6465

Pro Gly Asn Glu Gly Asp Pro Val Lys Val Thr Ile Thr Ala Asp
    6470                6475                6480

Gln Thr Ser Val Ala Glu Asn Val Lys Pro Thr Phe Thr Val His
    6485                6490                6495

Val Asn Gln Pro Leu Ala His Asp Leu Val Val Thr Leu Ser Asn
```

```
                 6500              6505              6510

Asn Ala Gln Val Thr Ile Lys Ala Gly Glu Thr Ser Ala Pro Tyr
    6515              6520              6525

Thr His Asp Ala Gln Gly Asp Val Tyr Asn Asp Ala Gly Gln
    6530              6535              6540

Ile Ser Leu Gly Ile Asn Ser Ala Val Asp Ala Thr Gly Ala Thr
    6545              6550              6555

Phe Glu Asn Leu Glu Leu Gly Gly Ala Ala Ser Val Gln Val Thr
    6560              6565              6570

Asp Thr Thr Asp Glu Val Val Ala Lys Leu Thr Ala Thr Pro Ser
    6575              6580              6585

Val Thr Glu Gly Gly Glu Ile Thr Tyr Thr Ile Thr Leu Thr Asn
    6590              6595              6600

Lys Asp Gly Leu Pro Ile Asp Lys His Ala Ala Leu Thr Phe Thr
    6605              6610              6615

Leu Asp Asp Gly Lys Thr Thr Ile Thr Ile Pro Ala Asn Gly Thr
    6620              6625              6630

Thr Gly Thr Ala Thr Val Thr Ala Pro Asp Asn Val Tyr Val Gly
    6635              6640              6645

Thr Asn Asp Pro Val Val Met Ser Ile Ala Thr Val Gly Gly Ala
    6650              6655              6660

Asp Val Gly Lys Phe Glu Gln Leu Thr Leu Asp Lys Thr Pro Val
    6665              6670              6675

Ser Thr Ser Val Thr Asp Glu Pro Gly Thr Pro Gly Asn Glu Gly
    6680              6685              6690

Asp Leu Val Lys Val Thr Ile Thr Ala Asp Gln Thr Ser Val Ala
    6695              6700              6705

Glu Asn Val Lys Pro Thr Phe Thr Val His Val Asn Gln Pro Leu
    6710              6715              6720

Ala His Asp Leu Val Val Thr Leu Ser Asn Asn Ala Gln Val Thr
    6725              6730              6735

Ile Lys Ala Gly Glu Thr Ser Ala Pro Tyr Thr His Ala Ala Gln
    6740              6745              6750

Gly Asp Asp Val Tyr Asn Asp Ala Gly Gln Ile Ser Leu Gly Ile
    6755              6760              6765

Thr Ser Ala Val Asp Val Asp Gly Arg Thr Phe Glu Asn Leu Glu
    6770              6775              6780

Leu Gly Gly Ala Ala Ser Val Gln Val Thr Asp Thr Leu Asp Glu
    6785              6790              6795

Val Val Ala Lys Leu Thr Ala Thr Pro Ser Val Thr Glu Gly Gly
    6800              6805              6810

Glu Ile Thr Tyr Thr Ile Thr Leu Thr Asn Lys Asp Gly Leu Pro
    6815              6820              6825

Ile Asn Asn His Ser Ala Leu Thr Phe Thr Leu Ser Asp Gly Lys
    6830              6835              6840

Thr Val Ile Thr Val Pro Ala Asn Gly Thr Val Gly Thr Ala Thr
    6845              6850              6855

Val Thr Ala Pro Asp Asn Val Tyr Val Gly Ala Asn Asp Pro Val
    6860              6865              6870

Val Met Ser Ile Ala Thr Val Glu Gly Ala Asp Val Gly Lys Phe
    6875              6880              6885

Glu Gln Leu Thr Leu Asp Lys Thr Pro Val Ser Thr Ser Val Thr
    6890              6895              6900
```

```
Asp Glu Pro Gly Thr Pro Gly Asn Glu Gly Asp Leu Val Lys Val
    6905            6910                6915

Thr Ile Thr Ala Asp Gln Thr Ser Val Ala Glu Asn Val Lys Pro
    6920            6925                6930

Thr Phe Thr Val His Val Asn Gln Pro Leu Ala His Asp Leu Val
    6935            6940                6945

Val Thr Leu Ser Asn Asn Ala Gln Val Thr Ile Lys Ala Gly Glu
    6950            6955                6960

Thr Ser Ala Pro Tyr Thr His Ala Ala Gln Gly Asp Asp Val Tyr
    6965            6970                6975

Asn Asp Ala Gly Gln Ile Ser Leu Gly Ile Thr Ser Ala Val Asp
    6980            6985                6990

Val Asp Gly Arg Thr Phe Glu Asn Leu Gln Leu Gly Gly Ala Ala
    6995            7000                7005

Thr Val Gln Val Thr Asp Thr Asp Glu Val Val Ala Lys Leu
    7010            7015                7020

Thr Ala Thr Pro Ser Val Thr Glu Gly Gly Glu Ile Thr Tyr Thr
    7025            7030                7035

Ile Thr Leu Thr Asn Lys Asp Gly Leu Pro Ile Asn Asn His Ser
    7040            7045                7050

Ala Leu Thr Phe Thr Leu Ser Asp Gly Lys Thr Val Ile Thr Val
    7055            7060                7065

Pro Ala Asn Gly Thr Val Gly Thr Ala Thr Val Thr Ala Pro Asp
    7070            7075                7080

Asn Val Tyr Val Gly Thr Asn Asp Pro Val Ile Lys Ser Ile Ala
    7085            7090                7095

Thr Val Glu Gly Ala Asp Val Gly Lys Phe Glu Gln Leu Thr Leu
    7100            7105                7110

Asp Lys Thr Pro Val Ser Thr Ser Val Thr Asp Glu Pro Gly Thr
    7115            7120                7125

Pro Gly Asn Glu Gly Asp Leu Val Lys Val Thr Ile Thr Ala Asp
    7130            7135                7140

Gln Thr Ser Val Ala Glu Asn Val Lys Pro Thr Phe Thr Val His
    7145            7150                7155

Val Asn Gln Pro Leu Ala His Asp Leu Val Val Thr Leu Ser Asn
    7160            7165                7170

Asn Ala Gln Val Thr Ile Lys Ala Gly Glu Thr Ser Ala Pro Tyr
    7175            7180                7185

Thr His Ala Ala Gln Gly Asp Asp Val Tyr Asn Asp Ala Gly Gln
    7190            7195                7200

Ile Ser Leu Gly Ile Asn Ser Ala Val Asp Ala Thr Gly Ala Thr
    7205            7210                7215

Phe Glu Asn Leu Gln Leu Gly Gly Ala Ala Thr Val Gln Val Thr
    7220            7225                7230

Asp Thr Thr Asp Glu Val Val Ala Lys Leu Thr Ala Thr Pro Ser
    7235            7240                7245

Val Thr Glu Gly Gly Glu Ile Thr Tyr Thr Ile Thr Leu Thr Asn
    7250            7255                7260

Lys Asp Gly Leu Pro Ile Asn Asn His Ser Ala Leu Thr Phe Thr
    7265            7270                7275

Leu Ser Asp Gly Lys Thr Val Ile Thr Val Pro Ala Asn Gly Thr
    7280            7285                7290
```

-continued

```
Val Gly Thr Ala Thr Val Thr Ala Pro Asp Asn Val Tyr Val Gly
7295                 7300                7305
Thr Asn Asp Pro Val Val Met Ser Ile Ala Thr Val Gly Gly Ala
7310                 7315                7320
Asp Val Gly Lys Phe Glu Gln Leu Thr Leu Asp Lys Thr Pro Val
7325                 7330                7335
Ser Thr Ser Val Thr Asp Glu Pro Gly Thr Pro Gly Asn Glu Gly
7340                 7345                7350
Asp Leu Val Lys Val Thr Ile Thr Ala Asp Gln Thr Ser Val Ala
7355                 7360                7365
Glu Asn Val Lys Pro Thr Phe Thr Val His Val Asn Gln Pro Leu
7370                 7375                7380
Ala His Asp Leu Val Val Thr Leu Ser Asn Asn Ala Gln Val Thr
7385                 7390                7395
Ile Lys Ala Gly Glu Thr Ser Ala Pro Tyr Thr His Ala Ala Gln
7400                 7405                7410
Gly Asp Asp Val Tyr Asn Asp Ala Gly Gln Ile Ser Leu Gly Ile
7415                 7420                7425
Asn Ser Ala Val Asp Ala Thr Gly Ala Thr Phe Glu Asn Leu Glu
7430                 7435                7440
Leu Gly Gly Ala Ala Lys Val Asp Val Thr Asp Thr Thr Asp Glu
7445                 7450                7455
Val Val Ala Lys Leu Thr Ala Thr Pro Ser Val Thr Glu Gly Gly
7460                 7465                7470
Glu Ile Thr Tyr Thr Ile Thr Leu Thr Asn Lys Asp Gly Leu Pro
7475                 7480                7485
Ile Asn Asn His Ser Ala Leu Thr Phe Thr Leu Ser Asp Gly Lys
7490                 7495                7500
Thr Val Ile Thr Val Pro Ala Asn Gly Thr Val Gly Thr Ala Thr
7505                 7510                7515
Val Thr Ala Pro Asp Asn Val Tyr Val Gly Thr Asn Asp Pro Val
7520                 7525                7530
Ile Lys Ser Ile Ala Thr Val Gly Gly Ala Asp Val Gly Lys Phe
7535                 7540                7545
Glu Gln Leu Thr Leu Asp Lys Thr Pro Val Ser Thr Ala Val Thr
7550                 7555                7560
Asp Glu Pro Gly Ser Gly Thr Pro Gly Thr Gly Asn Lys Gly Asp
7565                 7570                7575
Val Thr Thr Val Gly Ile Thr Gly Thr Thr Ser Leu Thr Glu Gly
7580                 7585                7590
Glu Thr Gly Gln Tyr Thr Leu Thr Leu Ser Asn Ala Ser Lys Ser
7595                 7600                7605
Glu Val Thr Ile Thr Leu Ser Tyr Ser Gly Thr Ala Gln Asn Gly
7610                 7615                7620
Asp Asp Phe Thr Gly Val Ala Thr Val Lys Ile Pro Ala Asn Ser
7625                 7630                7635
Thr Gly Thr Thr Phe Asn Ile Ala Thr Leu Asn Asp Lys Leu Val
7640                 7645                7650
Glu Gly Thr Glu Asn Phe Val Val Lys Ile Glu Thr Ala Thr Gly
7655                 7660                7665
Gly Asn Phe Glu Asn Leu Gln Val Asp Ser Ser Lys Ser Ser Val
7670                 7675                7680
Thr Thr Thr Ile Leu Asp Asn Asp His Leu Pro Val Ser Pro Gly
```

```
              7685              7690              7695
Gly Ala Val Phe Gly Val Glu Asp Thr Asp Tyr Val Phe Ala Trp
    7700              7705              7710
Ser Asp Phe Lys Val Thr Asp Ala Asp Gly Asn Thr Asn Leu Ser
    7715              7720              7725
Val Thr Ile Thr Ser Leu Pro Ala Ala Gly Asn Leu Gln Phe Phe
    7730              7735              7740
Asn Gly Thr Ala Trp Val Asn Val Ala Val Gly Gln Val Val Ser
    7745              7750              7755
Gln Ala Asp Ile Thr Ala Lys Asn Leu Lys Phe Val Pro Ala Leu
    7760              7765              7770
Asn Gln Ser Gly Ala Asp Asn Tyr Gly Gly Asn Gly Val Gly Asn
    7775              7780              7785
Gln Lys Ala Asp Tyr Ala Gln Phe Lys Phe Lys Pro Asn Asp Gly
    7790              7795              7800
Thr Asn Leu Gly Ser Glu Val Thr Met Lys Val Asp Ile Ser Pro
    7805              7810              7815
Val Ala Asp Lys Pro Thr Leu Ser Phe Gly Ser Ala Asp Ile Glu
    7820              7825              7830
Ser Lys Gly Leu Thr Lys Glu Val Trp Thr Ser Leu Lys Gly Leu
    7835              7840              7845
Gly Thr Gly Gly Asn Gly Ile Thr Gly Glu Asp Leu Lys Thr Val
    7850              7855              7860
Phe Ala Asn Ser Gly Ser Ala Asn Ser Ser Ser Thr Thr Thr Asn
    7865              7870              7875
Val Gln Ser Asp Gly Ser Val Thr Ala Gly Thr Gly Ser Lys Thr
    7880              7885              7890
Ser Gly Leu Ile Tyr Leu Glu Ala Gly Lys Val Tyr Thr Phe Ser
    7895              7900              7905
Gly Leu Ala Asp Asp Ser Phe Val Val Thr Ile Gly Gly Lys Thr
    7910              7915              7920
Val Val Thr Ala Thr Trp Gly Ala Gly Gly Val Ser Gly Thr
    7925              7930              7935
Phe Thr Pro Asn Thr Ser Gly Tyr Tyr Pro Ile Glu Val Tyr His
    7940              7945              7950
Ala Asn Gln Ser Gly Pro Gly Ser Tyr Asp Leu Asn Ile Gln Val
    7955              7960              7965
Gly Ser Gly Ala Val Thr Asp Leu Ser Ser Ser Asn Val Lys Met
    7970              7975              7980
Tyr Gln Asn Val Thr Glu Met Ala Asn Ala Gly Leu Gly Val Ser
    7985              7990              7995
Asp Leu His Thr Val Asn Gly Gln Ser Tyr Tyr Asp Gly Tyr Lys
    8000              8005              8010
Leu Asn Glu Gly Pro Glu Gly Gly Ser Val Lys Leu Val Gly Ile
    8015              8020              8025
Ser Thr Ala Leu Thr Asp Thr Asp Gly Ser Glu Ser Leu Asn Val
    8030              8035              8040
Thr Leu Ser Gly Ile Pro Lys Gly Thr Val Leu Ser Asp Gly Ala
    8045              8050              8055
Gly His Thr Val Thr Val Gly Thr Ala Pro Val Asp Val Thr Gly
    8060              8065              8070
Trp Lys Leu Ser Ser Leu Thr Leu Thr Pro Pro Ala Tyr Tyr Lys
    8075              8080              8085
```

Gly Ser Phe Asp Ile Thr Val Thr Ser Thr Ala Thr Glu Ser Leu
8090            8095                    8100

Gly Gly Ser Ala Ile Thr Thr Gly Asn Ile Pro Val Thr Val Tyr
8105            8110                    8115

Gly Ala Thr Tyr Lys Ala Ser Val Gly Thr Ser Gly Asn Asp Thr
8120            8125                    8130

Leu Thr Gly Ser Glu Gly Asn Asp Ile Phe Val Ala Asp Val Ser
8135            8140                    8145

Gly Leu Asn Val Val Gln Gly Lys Asn Tyr Asn Ile Ala Phe Met
8150            8155                    8160

Val Asp Ser Ser Gly Ser Met Ser Asp Lys Ser Ile Ala Asp Ala
8165            8170                    8175

Lys Thr Gln Leu Ala Ser Val Phe Asn Thr Leu Lys Ala Ser Leu
8180            8185                    8190

Gly Ser Asp Thr Ser Gly Thr Val Asn Ile Phe Leu Val Asp Phe
8195            8200                    8205

Asp Thr Gln Val Asn Lys Asn Val Ala Val Asn Leu Ala Asp Pro
8210            8215                    8220

Asp Ala Leu Ser Lys Leu Gln Ala Val Leu Asn Ser Met Val Gly
8225            8230                    8235

Gly Tyr Tyr Gly Gly Gly Thr Asn Tyr Glu Asp Ala Phe Lys Thr
8240            8245                    8250

Thr Ser Asn Phe Phe Asn Ser Thr Met Ala Thr Ser Asn Lys Gly
8255            8260                    8265

Ala Glu Asn Leu Thr Tyr Phe Ile Thr Asp Gly Lys Pro Thr Tyr
8270            8275                    8280

Tyr Gln Ser Asn Glu Ser Thr Asn Pro Ser Leu Trp Lys Asn Gly
8285            8290                    8295

Lys Ser Leu Asp Asp Val Val Asn Val Asn Asn Tyr Lys Met Gly
8300            8305                    8310

Asp Thr Phe Ser Ala Trp Ala Asp Ala Thr His Lys Val Glu Ile
8315            8320                    8325

Ser Ser Ser Gly Val Val Lys Val Leu Thr Tyr Thr Glu Asn Arg
8330            8335                    8340

Arg Gly Glu Leu Val Leu Asp Ser Thr Lys Thr Val Gly Thr Leu
8345            8350                    8355

His Ala Gln Gly Asp Gly Thr Tyr Glu Phe Ser Ser Leu Asp Gly
8360            8365                    8370

Thr Gly Tyr Ala Asp Tyr Trp Asn Tyr Val Tyr Ser Ala Ala Gly
8375            8380                    8385

Ser Thr Glu Ser Phe Ala Val Leu Gly Gly Thr Asn Gly Leu Ser
8390            8395                    8400

Lys Val Gln Ala Ile Gly Leu Asn Ser Asp Val Thr Leu Asn Asp
8405            8410                    8415

Leu Lys Pro Tyr
8420

<210> SEQ ID NO 38
<211> LENGTH: 1461
<212> TYPE: DNA
<213> ORGANISM: Pseudomonas putida

<400> SEQUENCE: 38
ctgggcctgc cgcggctaga tgggatagtg acgcgggccg tgctggaggg tgacccagcg    60

```
caactgggtg aactgatcga tggccgtgcg gctgccgaag ctgccatagc cgctggactt    120
gaccccgcca acggcatct gcgcttcatc gtgaacggtc gggccgttga tatggcagat    180
acccgactcc acccgttggg ccaaggccag ggcgcggctg tgtcgcggc tgaaaatggc    240
cgatgacaga ccgaactccg agtcgttggc cagctgcagc aaggcttcgt cgccttcggc    300
gcgcagtacc accgccaccg ggccgaagga ctcctcgcgg tacaggcgca tgctggcatc    360
gacgttgtcg agcaaggtcg gttgcaggat gctgccttcc agctggccgc cgctgaccag    420
gcgcgcgccc ttggccacgg catcgtcgat cagtgccttg atgcgctcgc cggccgctgc    480
gctgaccagc gagccgagca ccgaggtgct ggcttgcgga tcacctgcac gcagcccggc    540
gatcttcacc gccagcttgt cgacgaaagc gtcggcaata cagctgtcca ccacaaggcg    600
ctcggtggac atgcagatct gcccctggtt gaagtaggca ccgaaggccg ccgcttcgac    660
cgtggcgtcc aggtcggcat cgtcgagcac cagcaaaggt gccttgccgc ccagttcgag    720
cagggccggt tgagatggc gggccgccag ttcgccgacg atgcgcccga cgtgcgtcga    780
accggtgaag ttgacccggc gtaccgcagg gttggcgatc agccgctcga cgatggcggg    840
ggcatcctgc ggcgcattgc tgatgacatt gaccacgccg tcgccgatgc ctgcatcgtg    900
cagcacctgg ccgatcagcc gatggaccgc cgggctcagc tccgaggcct tgagcaccac    960
ggtgttgccg caggccagcg gcatggcaat ggcacgcgtg gccagtatca ccggggcgtt   1020
ccacggtgcg atgcccaaca ccacgccgca gggcgcgcgc agggccattg cgaagctgcc   1080
gggaacgtcc gaggggatca cttcaccggt gatctgcgtg gtcatggctg cagcctcgcg   1140
cagcatgttg gcggccaact tcacgttgaa gccataccag ttggccatgg cccggttttc   1200
accggcggcg gcgatgaact cggcggcct cgcctgcaac agatcagcgc ctgccagcaa   1260
gcggctgcgc cgctcgcccg gtgccagggc ggcccaggcc ggaaacgccg cgctggcagc   1320
agccaccgcg gcatcggcat cggccagtgt ggcggcggca gcctgcgaca ccacctcgcc   1380
agtcaccggg ttacagcgct cgaaggttcg tccatcgctg gcggggcgcg actgcccgcc   1440
aatcagcaaa ggcacctgca a                                             1461
```

<210> SEQ ID NO 39
<211> LENGTH: 482
<212> TYPE: PRT
<213> ORGANISM: Pseudomonas putida

<400> SEQUENCE: 39

```
Met Leu Gln Val Pro Leu Leu Ile Gly Gly Gln Ser Arg Pro Ala Ser
1               5                   10                  15

Asp Gly Arg Thr Phe Glu Arg Cys Asn Pro Val Thr Gly Glu Val Val
            20                  25                  30

Ser Gln Ala Ala Ala Ala Thr Leu Ala Asp Ala Asp Ala Val Ala
        35                  40                  45

Ala Ala Ser Ala Ala Phe Pro Trp Ala Ala Leu Ala Pro Gly Glu
    50                  55                  60

Arg Arg Ser Arg Leu Leu Ala Gly Ala Asp Leu Leu Gln Ala Arg Ala
65                  70                  75                  80

Ala Glu Phe Ile Ala Ala Ala Gly Glu Thr Gly Ala Met Ala Asn Trp
                85                  90                  95

Tyr Gly Phe Asn Val Lys Leu Ala Ala Asn Met Leu Arg Glu Ala Ala
            100                 105                 110

Ala Met Thr Thr Gln Ile Thr Gly Glu Val Ile Pro Ser Asp Val Pro
```

```
            115                 120                 125
Gly Ser Phe Ala Met Ala Leu Arg Ala Pro Cys Gly Val Val Leu Gly
    130                 135                 140

Ile Ala Pro Trp Asn Ala Pro Val Ile Leu Ala Thr Arg Ala Ile Ala
145                 150                 155                 160

Met Pro Leu Ala Cys Gly Asn Thr Val Val Leu Lys Ala Ser Glu Leu
                165                 170                 175

Ser Pro Ala Val His Arg Leu Ile Gly Gln Val Leu His Asp Ala Gly
            180                 185                 190

Ile Gly Asp Gly Val Val Asn Val Ile Ser Asn Ala Pro Gln Asp Ala
        195                 200                 205

Pro Ala Ile Val Glu Arg Leu Ile Ala Asn Pro Ala Val Arg Arg Val
210                 215                 220

Asn Phe Thr Gly Ser Thr His Val Gly Arg Ile Val Gly Glu Leu Ala
225                 230                 235                 240

Ala Arg His Leu Lys Pro Ala Leu Leu Glu Leu Gly Gly Lys Ala Pro
                245                 250                 255

Leu Leu Val Leu Asp Asp Ala Asp Leu Asp Ala Thr Val Glu Ala Ala
            260                 265                 270

Ala Phe Gly Ala Tyr Phe Asn Gln Gly Gln Ile Cys Met Ser Thr Glu
        275                 280                 285

Arg Leu Val Val Asp Ser Cys Ile Ala Asp Ala Phe Val Asp Lys Leu
    290                 295                 300

Ala Val Lys Ile Ala Gly Leu Arg Ala Gly Asp Pro Gln Ala Ser Thr
305                 310                 315                 320

Ser Val Leu Gly Ser Leu Val Ser Ala Ala Gly Glu Arg Ile Lys
                325                 330                 335

Ala Leu Ile Asp Asp Ala Val Ala Lys Gly Ala Arg Leu Val Ser Gly
            340                 345                 350

Gly Gln Leu Glu Gly Ser Ile Leu Gln Pro Thr Leu Leu Asp Asn Val
        355                 360                 365

Asp Ala Ser Met Arg Leu Tyr Arg Glu Glu Ser Phe Gly Pro Val Ala
370                 375                 380

Val Val Leu Arg Ala Glu Gly Asp Glu Ala Leu Leu Gln Leu Ala Asn
385                 390                 395                 400

Asp Ser Glu Phe Gly Leu Ser Ser Ala Ile Phe Ser Arg Asp Thr Ser
                405                 410                 415

Arg Ala Leu Ala Leu Ala Gln Arg Val Glu Ser Gly Ile Cys His Ile
            420                 425                 430

Asn Gly Pro Thr Val His Asp Glu Ala Gln Met Pro Phe Gly Gly Val
        435                 440                 445

Lys Ser Ser Gly Tyr Gly Ser Phe Gly Ser Arg Thr Ala Ile Asp Gln
    450                 455                 460

Phe Thr Gln Leu Arg Trp Val Thr Leu Gln His Gly Pro Arg His Tyr
465                 470                 475                 480

Pro Ile
```

<210> SEQ ID NO 40
<211> LENGTH: 5225
<212> TYPE: DNA
<213> ORGANISM: Pseudomonas putida

<400> SEQUENCE: 40
agccattggc ccgaccgccg tatcctcaac ctgctgggca tcgagctgcc cattctgcag    60

-continued

```
gcacccatgg cggggcgac cggctcggcc atggccatcg ctgtgggcca ggcaggtggg      120
ctgggcgccc tgccctgcgc catgctcagc ggcgaacagg tgcgcgccga gatcgctgca      180
ttccgcgccg gctgcccggg gcgcccgctg aacctgaact tcttctgcca ccagccgcca      240
gcgcccgatg ccgagcgcga tgcgcgctgg aagcaggcac ttgagcctta ttacagcgaa      300
gtgggcgccg atttcacggc gcccacgccg gtgtccaacc gtgcgccttt cgacgagcag      360
agctgcctgc tggtcgaagc gttgcgcccg gaggtggtga gcttccattt cggcctgccg      420
caggccgaac tgctgcagcg ggtaaaggcc agcggtgcca aggtactgtc cagcgccacg      480
accgtggaag aagcggcctg gctggagcgc aatggctgcg atgcgatcat cgccatgggg      540
tatgaagccg gtggccatcg cggcatgttc ctcagcgatg acatcaccag ccagataggc      600
accttcgcgc tcgtaccgca ggtggccgat gccgtcggcg tgccggtgat tgccgccggt      660
ggtatcggcg accaccgcgg gctgttggcg gcactggccc tgggtgcctc ggcagtgcag      720
atcggcacgc cttacctgtt ctgccccgag gccaaggtgt cgccagcgca tcgccaggcg      780
ctggacagcg cgcctgccag cgacaccgcc ctgaccaacc tgttcaccgg ccgcccggcg      840
cgcggcatca acaatcgcct catgcgcgag ctggggccga tgagcgagct tgcaccgcgc      900
ttcccgctgg cgggcggggc attgatgcct ttacgggcga tcaccgatcc gcagggtaag      960
agtgatttca gcaatctgtg gtcggggcag gcgttacggc taggccggca catgccggcg     1020
ggtgagctga cccgggagat tgccggtaag gcattggcag tgatcggtca ccaggcattc     1080
tgacaggcag gcatggcctc ttcacggcca atggcttatc gctatatagt taaggctata     1140
acgataacct caaggagctg tcttcatgcg tatccgctcg ccccagctgg tcatcactgc     1200
cctggccagc ctgctcggct tcaacactgc ctgggccgac gaagtccagg tcgcggtcgc     1260
agccaacttc acagcccctg tccaggccat cgccaaggac ttcgagaaag acaccggcca     1320
caaactgatc gcggcctacg cgccaccgg gcagttctac gcgcagatca agaacggtgc     1380
accgttcgaa gtgttcctcg ccgctgacga ctccaccccc aagaagctgg aagcagaaag     1440
ggaaaccgta cctggctcac gctttaccta cgccatcggc accctggcct tgtggtctgc     1500
gaaggaaggc tacgtagatg ccaagggtga agtgctgaaa aagaacgaat acaaacacct     1560
gtccatcgcc aacccgaaag cggcaccttta cggcctggcc gccacccagg tactggacgg     1620
gctgaagctc accgaggcca ccaaaggcaa gatcgtcgaa ggccagaaca tcacccaggc     1680
cttccagttc gtctccaccg gcaacgccga gctgggcttc gtcgcccttt cgcagatcta     1740
caaggacggc aaggtaaccc atggctcggc atggatcgtg ccgtccaacc tgcacgaccc     1800
gatccgccag gacgccgtca tcctcaacaa aggcaaggac aatgcggccg ccaaggcact     1860
ggtcgaatac ctcaaaggcc gaaagccgc agcggtgatc aaatcctatg gttatgaacg     1920
ctgatgccac tcgatgccag tgacctgggc gccatctggc tgaccgtaaa actggccagc     1980
ctgaccaccc tgatcctgct gatcatcggc acacccgtcg cctggtggct cgcgcgcacg     2040
cgctcttggc tgcgcgggcc ggtgggtgcg gtggtggcac tgccgctggt actgccaccg     2100
acggtgatcg ttttttacct gttgatcgcc cttggcccgc acggctggct tggtcaggcc     2160
acccaggcgc taggcctggg cagtgtgtg ttcagcttca caggcctggt gattggctcg     2220
acggtgtact ccatgccgtt cgtggtgcaa ccctgcagaa atgcctttgg cgcgatcggc     2280
cagcgccccc tggaagtcgc cgctactctg cgagccagcc catgggatac cttcgttcat     2340
gtggtgctgc cgctggcccg ccctggcttc gtcactgcca gcatcctcgg cttttgcccac     2400
```

```
acggtgggcg agtttggcgt cgtactgatg atcggcggca acatccccga caagactcgc    2460
gtggtttcgg tgcagatttt cgatcacgtc gaagccatgg agtattcgca ggcccactgg    2520
ctggccggtg ccatgctggt gttctctttc ctggtgctgc tcctgctgta cgctggacgc    2580
cgcggcaaag ctggctggag ctgaaatgac cgcatcgatt gtggcgcacc tgaaactggc    2640
acgcgacgac tttaccctgg acgtcaacct gcacctgccc gggcgcggca tcagcgcgct    2700
gttcggccac tctggctccg gcaagaccag ctgcctgcgc tgcctggccg ggctggaacg    2760
ggccgccagc gcctatatcg aagtcaacgg cgaagtctgg aagacagca cccgaggcta    2820
cttccaggca ccgcacctgc gcccgtgggg ctacgtgttc caggaagcca gcctgttccc    2880
gcacctgtcg gtgcgcggca acctgacgtt cggctggcgc cgggtagcgc ccgctgaacg    2940
caaggtcagc ctcgaccagg cgtgccaact gctgggtatc ggccacttgc tggaccgccg    3000
cccggcaacc ctgtcggtg gcgaggcgca gcgggtgggt attgcccgcg ccctgctcag    3060
cagcccgcgg ctgttgttga tggacgagcc gctggcagcc ctcgacagcc cgcgcaagcg    3120
cgagatactg cccttcctgg agcgcctgca cgacgaactg gatatccctc tgatatatgt    3180
cagccacgcc caggatgaag tcgcgcggct ggccgaccac ctggtgttgc tggaacaagg    3240
ccgggcgatc gccagcggcc cgatcggcga accctggct cgccttgacc tgtcgctggc    3300
ccagggcgac gacgccggcg tcgtgttcga aggtagggtg gttgggcacg acccgcatta    3360
cggcctgctg gacctgcgcc tgcccggcag cagcgggccg ctgctgcgca tcacccacgc    3420
ggcgcaggtg atgggcagca ccctgcgcgt caaggtgcag gcccgggatg tcagcctggc    3480
actggcggcg gatagcgcat cgagcatcct caaccgcctg ccggtgcgtg tgcgcgagag    3540
ctgcccggcg gccaacccgg cgcatgtgct ggtcagcctg gatgctggcg gcaatgccct    3600
gcttgcacgc atcacccgct ctcggcagga ccagctcggc ttgcacacag gcagatact    3660
gttcgcccag atcaagtcgg tggccctttt gggttgagca tcctcagcgc gcgtattgtc    3720
cattgatcag tgacctgatc gaggcccgcc gccatgctt gactgccccc tgccgcgcac    3780
cctgcactac gttgacgaca gtcagccggg cctgacccgt cggcgctggc gcgaccgttt    3840
catctacctg gatgccgatg ccaacgggt acgcgacagc gaaacccttg cgcgcatcgc    3900
cgcattggtg atcccccgg cctacacgga tgtgtggatc tgcgccgatc cgcaaggcca    3960
cctgcaagcc accggccgcg atgcccgtgg ccgcaagcag taccgctacc acgcacagtg    4020
gcgcgaactg cgcgaccagc acaaatacgg gcgcatgctt gcgttcgccc aagccctgcc    4080
aaagctgcgc acacagctgg aagcccactt ggcgcggcca gggctggacc gggaaaaagt    4140
catggcgctg gtggtgagcc tgctggacca caccctgatc cgcatcggca accagcgcta    4200
cctgcgcgat aaccggtcgt acggattgac caccctgcgc aatcgccatg tgcaggtcaa    4260
aggcagcact atccgcttcc agttccgcgg caagcgcggc gtcgaacaca acgtcaccct    4320
caacgaccgg cgcttggcca acctactcaa acgctgcatg gaactgcctg ggcaggcact    4380
gtttcagtac ctggatgaag atggccagcg ccatagtgtc ggctccagcg aggtcaatca    4440
gtttctgcag cagttgaccg gtgccgactt tactgccaag gactatcgca cctgggccgg    4500
cagcagcctg gcattgaacc tgctaaagcc cttggcctgg gagccggaga gtgaagccaa    4560
acgccaggtc gccgcaatag tccgccaggt agccacgcgc ctgggcaata cgccggcagt    4620
gtgccggcgc tgctacatcc acccggcagt tctggagcac tatgccttgg ggcgcctggc    4680
caatttgccg aaaaaccgtg tgcgcaaagg cctggacccg gaggaagtgg ccttgctgtt    4740
gtttcttcag gcacttgagg aacaggagga ccattgagct tgtctattca gcccatgatg    4800
```

-continued

```
cgaagaaatt tcccattagc cgccaacccc cctattcttg ccagcgagca ccttggccga    4860
caaaccgttg acggtttgct ttggcacctg caactgaaga cacgcaacag aatttgtctg    4920
tcggggaatt actatccgcc gaaagcgtct ttaatgagaa ggaagaggga caagctcccg    4980
ccgccgcggc aactagccca gcggacttat acatcaccaa ggagaactac atgctgatac    5040
tcacccgtaa ggttggcgaa agcatcgtca tcaacgatga catcaaagtc accattctgg    5100
gcgtcaaagg gatgcaggtg aggatcggta tcgatgcacc gaaagatgtt caggtccatc    5160
gagaagagat tttcaaacgc atccaggccg gcagcccggc tccggagaaa cacgaagaca    5220
cacac                                                                5225
```

<210> SEQ ID NO 41
<211> LENGTH: 252
<212> TYPE: PRT
<213> ORGANISM: Pseudomonas putida

<400> SEQUENCE: 41

```
Met Arg Ile Arg Ser Pro Gln Leu Val Ile Thr Ala Leu Ala Ser Leu
1               5                   10                  15

Leu Gly Phe Asn Thr Ala Trp Ala Asp Glu Val Gln Val Ala Val Ala
            20                  25                  30

Ala Asn Phe Thr Ala Pro Val Gln Ala Ile Ala Lys Asp Phe Glu Lys
        35                  40                  45

Asp Thr Gly His Lys Leu Ile Ala Ala Tyr Gly Ala Thr Gly Gln Phe
    50                  55                  60

Tyr Ala Gln Ile Lys Asn Gly Ala Pro Phe Glu Val Phe Leu Ala Ala
65                  70                  75                  80

Asp Asp Ser Thr Pro Lys Lys Leu Glu Ala Glu Arg Glu Thr Val Pro
                85                  90                  95

Gly Ser Arg Phe Thr Tyr Ala Ile Gly Thr Leu Ala Leu Trp Ser Ala
            100                 105                 110

Lys Glu Gly Tyr Val Asp Ala Lys Gly Glu Val Leu Lys Lys Asn Glu
        115                 120                 125

Tyr Lys His Leu Ser Ile Ala Asn Pro Lys Ala Ala Pro Tyr Gly Leu
    130                 135                 140

Ala Ala Thr Gln Val Leu Asp Gly Leu Lys Leu Thr Glu Ala Thr Lys
145                 150                 155                 160

Gly Lys Ile Val Glu Gly Gln Asn Ile Thr Gln Ala Phe Gln Phe Val
                165                 170                 175

Ser Thr Gly Asn Ala Glu Leu Gly Phe Val Ala Leu Ser Gln Ile Tyr
            180                 185                 190

Lys Asp Gly Lys Val Thr His Gly Ser Ala Trp Ile Val Pro Ser Asn
        195                 200                 205

Leu His Asp Pro Ile Arg Gln Asp Ala Val Ile Leu Asn Lys Gly Lys
    210                 215                 220

Asp Asn Ala Ala Ala Lys Ala Leu Val Glu Tyr Leu Lys Gly Pro Lys
225                 230                 235                 240

Ala Ala Ala Val Ile Lys Ser Tyr Gly Tyr Glu Arg
                245                 250
```

<210> SEQ ID NO 42
<211> LENGTH: 226
<212> TYPE: PRT
<213> ORGANISM: Pseudomonas putida

<400> SEQUENCE: 42

```
Met Pro Leu Asp Ala Ser Asp Leu Gly Ala Ile Trp Leu Thr Val Lys
1               5                   10                  15

Leu Ala Ser Leu Thr Thr Leu Ile Leu Leu Ile Ile Gly Thr Pro Val
            20                  25                  30

Ala Trp Trp Leu Ala Arg Thr Arg Ser Trp Leu Arg Gly Pro Val Gly
        35                  40                  45

Ala Val Val Ala Leu Pro Leu Val Leu Pro Pro Thr Val Ile Gly Phe
    50                  55                  60

Tyr Leu Leu Ile Ala Leu Gly Pro His Gly Trp Leu Gly Gln Ala Thr
65                  70                  75                  80

Gln Ala Leu Gly Leu Gly Ser Val Val Phe Ser Phe Thr Gly Leu Val
                85                  90                  95

Ile Gly Ser Thr Val Tyr Ser Met Pro Phe Val Val Gln Pro Leu Gln
            100                 105                 110

Asn Ala Phe Gly Ala Ile Gly Gln Arg Pro Leu Glu Val Ala Ala Thr
        115                 120                 125

Leu Arg Ala Ser Pro Trp Asp Thr Phe Val His Val Leu Pro Leu
    130                 135                 140

Ala Arg Pro Gly Phe Val Thr Ala Ser Ile Leu Gly Phe Ala His Thr
145                 150                 155                 160

Val Gly Glu Phe Gly Val Val Leu Met Ile Gly Gly Asn Ile Pro Asp
                165                 170                 175

Lys Thr Arg Val Val Ser Val Gln Ile Phe Asp His Val Glu Ala Met
            180                 185                 190

Glu Tyr Ser Gln Ala His Trp Leu Ala Gly Ala Met Leu Val Phe Ser
        195                 200                 205

Phe Leu Val Leu Leu Leu Tyr Ala Gly Arg Arg Gly Lys Ala Gly
    210                 215                 220

Trp Ser
225
```

<210> SEQ ID NO 43
<211> LENGTH: 363
<212> TYPE: PRT
<213> ORGANISM: Pseudomonas putida

<400> SEQUENCE: 43

```
Met Thr Ala Ser Ile Val Ala His Leu Lys Leu Ala Arg Asp Asp Phe
1               5                   10                  15

Thr Leu Asp Val Asn Leu His Leu Pro Gly Arg Gly Ile Ser Ala Leu
            20                  25                  30

Phe Gly His Ser Gly Ser Gly Lys Thr Ser Cys Leu Arg Cys Leu Ala
        35                  40                  45

Gly Leu Glu Arg Ala Ala Ser Ala Tyr Ile Glu Val Asn Gly Glu Val
    50                  55                  60

Trp Glu Asp Ser Thr Arg Gly Tyr Phe Gln Ala Pro His Leu Arg Pro
65                  70                  75                  80

Val Gly Tyr Val Phe Gln Glu Ala Ser Leu Phe Pro His Leu Ser Val
                85                  90                  95

Arg Gly Asn Leu Thr Phe Gly Trp Arg Arg Val Ala Pro Ala Glu Arg
            100                 105                 110

Lys Val Ser Leu Asp Gln Ala Cys Gln Leu Leu Gly Ile Gly His Leu
        115                 120                 125
```

```
Leu Asp Arg Arg Pro Ala Thr Leu Ser Gly Gly Glu Ala Gln Arg Val
        130                 135                 140

Gly Ile Ala Arg Ala Leu Leu Ser Ser Pro Arg Leu Leu Leu Met Asp
145                 150                 155                 160

Glu Pro Leu Ala Ala Leu Asp Ser Pro Arg Lys Arg Glu Ile Leu Pro
                165                 170                 175

Phe Leu Glu Arg Leu His Asp Glu Leu Asp Ile Pro Leu Ile Tyr Val
            180                 185                 190

Ser His Ala Gln Asp Glu Val Ala Arg Leu Ala Asp His Leu Val Leu
        195                 200                 205

Leu Glu Gln Gly Arg Ala Ile Ala Ser Gly Pro Ile Gly Glu Thr Leu
210                 215                 220

Ala Arg Leu Asp Leu Ser Leu Ala Gln Gly Asp Asp Ala Gly Val Val
225                 230                 235                 240

Phe Glu Gly Arg Val Val Gly His Asp Pro His Tyr Gly Leu Leu Asp
                245                 250                 255

Leu Arg Leu Pro Gly Ser Ser Gly Pro Leu Leu Arg Ile Thr His Ala
            260                 265                 270

Ala Gln Val Met Gly Ser Thr Leu Arg Val Lys Val Gln Ala Arg Asp
        275                 280                 285

Val Ser Leu Ala Leu Ala Asp Ser Ala Ser Ser Ile Leu Asn Arg
290                 295                 300

Leu Pro Val Arg Val Arg Glu Ser Cys Pro Ala Ala Asn Pro Ala His
305                 310                 315                 320

Val Leu Val Ser Leu Asp Ala Gly Gly Asn Ala Leu Leu Ala Arg Ile
                325                 330                 335

Thr Arg Phe Ser Ala Asp Gln Leu Gly Leu His Thr Gly Gln Ile Leu
            340                 345                 350

Phe Ala Gln Ile Lys Ser Val Ala Leu Leu Gly
        355                 360
```

<210> SEQ ID NO 44
<211> LENGTH: 1479
<212> TYPE: DNA
<213> ORGANISM: Pseudomonas putida

<400> SEQUENCE: 44

```
atctacgcac aacccggaac tccaggcgcc gtcgtatcct tcaaaccccg ttatggcaac    60
ttcatcggtg gcgagttcgt gcagccgttg gctggccagt acttcatcaa cagctcgccg   120
gtcaatggcc agccgattgc cgaattcccg cgctccacgg cccaggacgt cgagcgcgcc   180
ctggacgccg cgcatgccgc cgccgaagcc tgggcaagaa cctcggtgca agaccgtgcg   240
cgggtactgc tgaaaattgc cgaccgcatc gaacagaacc tggaagtgct ggcggttacc   300
gaaagctggg acaacggcaa ggccatacgc gaaaccttga atgccgacgt gccgctggca   360
gcggaccact ccgctatttt gccggttgc atccgcgccc aggagggtgg cgtaggcgag   420
atcaacgaag gcaccgtggc ttatcacatt cacgagccgc tgggtgtggt ggggcagatc   480
atcccgtgga acttcccgct gctgatggcc gcctggaagc tcgccccggc cttggccgct   540
ggcaactgcg tggtgctcaa gccgcggag cagacgccgc tgtcgattac cgtcttttgcc   600 gaactgatcg ccgacctgtt gccggcaggc gtactgaaca tcgtccaggg ctttggccgt   660
gaggccggtg aggcgctggc caccagcaag cgcattgcca agatcgcgtt caccgggtcc   720 acccggtgg gctcgcacat catgaagtgc gcggccgaga acatcatccc gtccaccgtc   780
```

```
gaactgggtg gcaagtcgcc gaacatttc ttcgaagaca tcatgcaggc cgagccggcg    840
ttcatcgaga aggctgccga aggcctggtg ctggcgttct tcaaccaggg cgaggtgtgc    900
acctgcccgt cacgggcgct gatccaggag tcgatctacg aaccgttcat ggccgaggtg    960
atgaagaaga tcgccaagat cacccgcggc aacccgctgg ataccgaaac catggtgggt    1020
gctcaggcgt ccgagcaaca gtacgacaag atcctttcgt acctggaaat tgcccgggag    1080
gagggcgcgc agctgctcac cggcggtggt gccgagcggc tgcagggtga cctgccagc     1140 ggttactaca ttcagccaac cctgctcaag gcaacaaca agatgcgcgt gttccaggaa     1200
gaaatcttcg gccagtggt gggcgtgacc accttcaagg acgaagccga agcgctggcg     1260
atcgccaacg acagtgaatt cggcctgggc gccggcctgt ggacccgcga catcaaccgc    1320
gcttaccgca tgggccgcgg gatcaaggcc gggcgagtgt ggaccaactg ctaccacctg    1380
tacccggcgc atgcggcgtt cgggggggtac aagaagtccg gtgttggccg tgagacccac    1440
aagatgatgc ttgaccatta tcagcagacc aagaacctg                           1479
```

<210> SEQ ID NO 45
<211> LENGTH: 494
<212> TYPE: PRT
<213> ORGANISM: Pseudomonas putida

<400> SEQUENCE: 45

```
Met Ile Tyr Ala Gln Pro Gly Thr Pro Gly Ala Val Val Ser Phe Lys
 1               5                  10                  15

Pro Arg Tyr Gly Asn Phe Ile Gly Gly Glu Phe Val Gln Pro Leu Ala
            20                  25                  30

Gly Gln Tyr Phe Ile Asn Ser Ser Pro Val Asn Gly Gln Pro Ile Ala
        35                  40                  45

Glu Phe Pro Arg Ser Thr Ala Gln Asp Val Glu Arg Ala Leu Asp Ala
    50                  55                  60

Ala His Ala Ala Glu Ala Trp Gly Lys Thr Ser Val Gln Asp Arg
65                  70                  75                  80

Ala Arg Val Leu Leu Lys Ile Ala Asp Arg Ile Glu Gln Asn Leu Glu
                85                  90                  95

Val Leu Ala Val Thr Glu Ser Trp Asp Asn Gly Lys Ala Ile Arg Glu
            100                 105                 110

Thr Leu Asn Ala Asp Val Pro Leu Ala Ala Asp His Phe Arg Tyr Phe
        115                 120                 125

Ala Gly Cys Ile Arg Ala Gln Glu Gly Gly Val Gly Glu Ile Asn Glu
    130                 135                 140

Gly Thr Val Ala Tyr His Ile His Glu Pro Leu Gly Val Val Gly Gln
145                 150                 155                 160

Ile Ile Pro Trp Asn Phe Pro Leu Leu Met Ala Ala Trp Lys Leu Ala
                165                 170                 175

Pro Ala Leu Ala Ala Gly Asn Cys Val Val Leu Lys Pro Ala Glu Gln
            180                 185                 190

Thr Pro Leu Ser Ile Thr Val Phe Ala Glu Leu Ile Ala Asp Leu Leu
        195                 200                 205

Pro Ala Gly Val Leu Asn Ile Val Gln Gly Phe Gly Arg Glu Ala Gly
    210                 215                 220

Glu Ala Leu Ala Thr Ser Lys Arg Ile Ala Lys Ile Ala Phe Thr Gly
225                 230                 235                 240

Ser Thr Pro Val Gly Ser His Ile Met Lys Cys Ala Ala Glu Asn Ile
                245                 250                 255
```

```
Ile Pro Ser Thr Val Glu Leu Gly Gly Lys Ser Pro Asn Ile Phe Phe
            260                 265                 270
Glu Asp Ile Met Gln Ala Glu Pro Ala Phe Ile Glu Lys Ala Ala Glu
                275                 280                 285
Gly Leu Val Leu Ala Phe Phe Asn Gln Gly Glu Val Cys Thr Cys Pro
            290                 295                 300
Ser Arg Ala Leu Ile Gln Glu Ser Ile Tyr Glu Pro Phe Met Ala Glu
305                 310                 315                 320
Val Met Lys Lys Ile Ala Lys Ile Thr Arg Gly Asn Pro Leu Asp Thr
                325                 330                 335
Glu Thr Met Val Gly Ala Gln Ala Ser Glu Gln Gln Tyr Asp Lys Ile
            340                 345                 350
Leu Ser Tyr Leu Glu Ile Ala Arg Glu Glu Gly Ala Gln Leu Leu Thr
            355                 360                 365
Gly Gly Gly Ala Glu Arg Leu Gln Gly Asp Leu Ala Ser Gly Tyr Tyr
        370                 375                 380
Ile Gln Pro Thr Leu Leu Lys Gly Asn Asn Lys Met Arg Val Phe Gln
385                 390                 395                 400
Glu Glu Ile Phe Gly Pro Val Val Gly Val Thr Thr Phe Lys Asp Glu
                405                 410                 415
Ala Glu Ala Leu Ala Ile Ala Asn Asp Ser Glu Phe Gly Leu Gly Ala
            420                 425                 430
Gly Leu Trp Thr Arg Asp Ile Asn Arg Ala Tyr Arg Met Gly Arg Gly
        435                 440                 445
Ile Lys Ala Gly Arg Val Trp Thr Asn Cys Tyr His Leu Tyr Pro Ala
450                 455                 460
His Ala Ala Phe Gly Gly Tyr Lys Lys Ser Gly Val Gly Arg Glu Thr
465                 470                 475                 480
His Lys Met Met Leu Asp His Tyr Gln Gln Thr Lys Asn Leu
                485                 490

<210> SEQ ID NO 46
<211> LENGTH: 1465
<212> TYPE: DNA
<213> ORGANISM: Pseudomonas putida

<400> SEQUENCE: 46
gctgatagtg atccagcatc atcttgtgcg tctcacgccc aaccccgac  ttcttgtacc      60 cgccgaacgc ggcatgcgcc gggtacaggt ggtagcagtt ggtccacaca cggccagcct     120
tgatgccccg gcccatgcgg taggcacggt tgatgtcgcg ggtccacacg ccggcgccca     180
ggccgaactc ggtgtcgttg caattgcca  gcgcttcggc ttcgtccttg aaggtggtga     240
cgctgaccac cgggccgaag atttcttcct ggaacacgcg catcttgttg ttgcccttga     300
gcagggtcgg ctggatgtag taaccggtag ccagcgaacc ttccagcttc tgaccttgc      360 cgccggtgag cagctcggcg ccttcttcct gggcaatctg caggtacgag aggatctttt     420
cgaactgctg ctgcgaggcc tgggcgccga ccatggtgtc ggtgtccaac gggtcgccgc     480
gcttgatctg cagcaccttc ttcatcacca cttccatgaa ctgcggatag atcgactctt     540
gcaccagggc acgcgacggg caggtgcaca cttcaccctg gttgaagaac gccagcacca     600
tgccttctgc cgccttctcg atgaagcttg gttcggcctg catgatgtct tcgaagtaca     660
cgttcggcga cttgccaccc agttcgacgg tggacgggat gatgttctcg gcggcgcatt     720
tcatgatgtg cgagcccacc ggggtagagc cggtgaaggc gatcttggcg atgcgtttgc     780
```

```
tggtggccag ggcttcaccg gcttcgcggc catagccttg cactacgttg agcacgccag      840
gtggcaacag gtcgccaatg acttcgagca gtacggtgat acccagcggc gtctgttcgg      900
caggcttgag caccacgcag ttaccagctg ccagtgccgg ggcaagcttc aggcagcca       960 tcaggatcgg gaagttccag gggatgatct gcccgaccac gcccagtggc tcgtggatgt     1020
ggtaggccac ggtgccttca ttgatttcgg cagcgccgcc ttcctgggcg cggatgcagc     1080
cagcgaaata gcggaagtgg tcgaccgcca gcggaatgtc ggcgttgagg gtttcgcgga     1140
tcggcttgcc gttgtcccag gtttcggtaa tggccagcag ttcgaggttc tgctcgatgc     1200
ggtcggcgat cttcagcagc acgttggaac gatcctgcac tgaagtgcgg ccccaggcgt     1260
cggccgcagc atgggcggca tccagggctt tgtcgatgtc ttcggcagta gagcggggga     1320
actcagcgat cagcttgcca ttcaccgggg aggtattttc gaagtactgc cccttacccg     1380
gagtaacgaa ctcaccaccg atgtagttgc cgtagcggct cttgaaggaa accttcgcgc     1440
cttcggtacc gggatgtgca taacg                                          1465
```

<210> SEQ ID NO 47
<211> LENGTH: 506
<212> TYPE: PRT
<213> ORGANISM: Pseudomonas putida

<400> SEQUENCE: 47

```
Met Arg Tyr Ala His Pro Gly Thr Glu Gly Ala Lys Val Ser Phe Lys
1               5                   10                  15

Ser Arg Tyr Gly Asn Tyr Ile Gly Gly Glu Phe Val Thr Pro Val Lys
            20                  25                  30

Gly Gln Tyr Phe Glu Asn Thr Ser Pro Val Asn Gly Lys Leu Ile Ala
        35                  40                  45

Glu Phe Pro Arg Ser Thr Ala Glu Asp Ile Asp Lys Ala Leu Asp Ala
    50                  55                  60

Ala His Ala Ala Ala Asp Ala Trp Gly Arg Thr Ser Val Gln Asp Arg
65                  70                  75                  80

Ser Asn Val Leu Leu Lys Ile Ala Asp Arg Ile Glu Gln Asn Leu Glu
                85                  90                  95

Leu Leu Ala Ile Thr Glu Thr Trp Asp Asn Gly Lys Pro Ile Arg Glu
            100                 105                 110

Thr Leu Asn Ala Asp Ile Pro Leu Ala Val Asp His Phe Arg Tyr Phe
        115                 120                 125

Ala Gly Cys Ile Arg Ala Gln Glu Gly Gly Ala Ala Glu Ile Asn Glu
    130                 135                 140

Gly Thr Val Ala Tyr His Ile His Glu Pro Leu Gly Val Val Gly Gln
145                 150                 155                 160

Ile Ile Pro Trp Asn Phe Pro Ile Leu Met Ala Ala Trp Lys Leu Ala
                165                 170                 175

Pro Ala Leu Ala Ala Gly Asn Cys Val Val Leu Lys Pro Ala Glu Gln
            180                 185                 190

Thr Pro Leu Gly Ile Thr Val Leu Leu Glu Val Ile Gly Asp Leu Leu
        195                 200                 205

Pro Pro Gly Val Leu Asn Val Val Gln Gly Tyr Gly Arg Glu Ala Gly
    210                 215                 220

Glu Ala Leu Ala Thr Ser Lys Arg Ile Ala Lys Ile Ala Phe Thr Gly
225                 230                 235                 240

Ser Thr Pro Val Gly Ser His Ile Met Lys Cys Ala Ala Glu Asn Ile
```

```
                245                 250                 255
Ile Pro Ser Thr Val Glu Leu Gly Gly Lys Ser Pro Asn Val Tyr Phe
            260                 265                 270
Glu Asp Ile Met Gln Ala Glu Pro Ser Phe Ile Glu Lys Ala Ala Glu
        275                 280                 285
Gly Met Val Leu Ala Phe Phe Asn Gln Gly Glu Val Cys Thr Cys Pro
    290                 295                 300
Ser Arg Ala Leu Val Gln Glu Ser Ile Tyr Pro Gln Phe Met Glu Val
305                 310                 315                 320
Val Met Lys Lys Val Leu Gln Ile Lys Arg Gly Asp Pro Leu Asp Thr
                325                 330                 335
Asp Thr Met Val Gly Ala Gln Ala Ser Gln Gln Phe Glu Lys Ile
            340                 345                 350
Leu Ser Tyr Leu Gln Ile Ala Gln Glu Glu Gly Ala Glu Leu Leu Thr
        355                 360                 365
Gly Gly Lys Val Glu Lys Leu Glu Gly Ser Leu Ala Thr Gly Tyr Tyr
    370                 375                 380
Ile Gln Pro Thr Leu Leu Lys Gly Asn Asn Lys Met Arg Val Phe Gln
385                 390                 395                 400
Glu Glu Ile Phe Gly Pro Val Val Ser Val Thr Thr Phe Lys Asp Glu
                405                 410                 415
Ala Glu Ala Leu Ala Ile Ala Asn Asp Thr Glu Phe Gly Leu Gly Ala
            420                 425                 430
Gly Val Trp Thr Arg Asp Ile Asn Arg Ala Tyr Arg Met Gly Arg Gly
        435                 440                 445
Ile Lys Ala Gly Arg Val Trp Thr Asn Cys Tyr His Leu Tyr Pro Ala
    450                 455                 460
His Ala Ala Phe Gly Gly Tyr Lys Lys Ser Gly Val Gly Arg Glu Thr
465                 470                 475                 480
His Lys Met Met Leu Asp His Tyr Gln Gln Thr Lys Asn Leu Leu Val
                485                 490                 495
Ser Tyr Asp Ile Asn Pro Leu Gly Phe Phe
            500                 505

<210> SEQ ID NO 48
<211> LENGTH: 1473
<212> TYPE: DNA
<213> ORGANISM: Pseudomonas putida

<400> SEQUENCE: 48
gcggtatttg ccagtgactc ttttggccag ctgaaagtgg agaaaattat gactgcccag      60
tggaaccact acattaacgg ggaatacgta tcacccgaat ctgaagagta tatccacgag     120
ttcatcccaa ccacggcttt gccgggtgac tcaatcgcaa ggggctcggc agctgacgtt     180
gataaggctg ttcgtgccgc ggcagcggct cagcctgcct ggaatgcacg caagccaatt     240
gagcggggtc gtatccttct cgccatagct cgtttggttc gcgccaacgc agcggctttc     300
tgcgccaaag aagcggaaga aactggcaag cctctgaaga tggccgcctt tgagatcgag     360
gcatgtgctc agtactttga gtattacggc ggtttggcga cagccatcca gggcgaaacc     420
atcaacctcg gcccagcta ccacgccat accacccgag agccatttgg agtggtgggg     480
gtcatcctgc cgtggaattc gccactgaac caagctgggc gagccattgc cccggcattg     540
gttagcggga caccgtggt ggtcaaacct tcagagttca cctcggtgac gatgctccag     600
ttcgcggaac tggttgtgaa agaggcaggg ttgccaccag gcgtattgaa cgtggttacc     660
```

-continued

```
ggcaccggta aggaaaccgg tgagcctctg gttaaacacc ctctgatccg aaaggttgct    720
ttcaccggtt ctgtccgtgc cggacgggag atcggcaagc tcgccgcaga tcgcatcatt    780
ccgctgtcgc tcgaattggg cggcaaatcc ccgaacattg tcttcgaaga cgcagatctg    840
gatcgagctg tcgcgggtag cgtctttgcc ttcaccgtca acactggtca agtctgtctc    900
gccgggaccc gttgcctggt gcatgagtcg attttttgaaa aattctccaa gaagcttgcc    960
ggtgctgtag aggcgcttca gttcagcgac ggcgaaagct tcggtctcgg ccccctaacg   1020
accaaggctc agtttgagca ggttcatcgt tacaacgagc tggccatcca ggagggggct   1080
cattgcttgg tcgtgggga agctccaagt gacaaaaccg gctggtacgt acgacccacc   1140
gtctacacca acgtcaacaa ctcgatgcgg attgctcggg aagaaatttt cggacccgtt   1200
ctggtactga ttccgttcaa ggacgaaaac gaggcggtgg ccatcgcgaa tgactcggac   1260
tacgggctcg cggctggcgt atggaccacc gatctggctc gcgcgcaccg cgtatccgct   1320
caaatcgaag cgggccaggt gtacgtcaac gaatatccat caggtggcgt tgagactcca   1380
ttcggcggtt tcaagcaaag cggccatggg cgcgagaagg gcattgaagc actccaccat   1440
tacacccaaa caaagacgac catcatccgc att                                1473
```

<210> SEQ ID NO 49
<211> LENGTH: 492
<212> TYPE: PRT
<213> ORGANISM: Pseudomonas putida

<400> SEQUENCE: 49

```
Met Ala Val Phe Ala Ser Asp Ser Phe Gly Gln Leu Lys Val Glu Lys
1               5                   10                  15

Ile Met Thr Ala Gln Trp Asn His Tyr Ile Asn Gly Glu Tyr Val Ser
            20                  25                  30

Pro Glu Ser Glu Glu Tyr Ile His Glu Phe Ile Pro Thr Thr Ala Leu
        35                  40                  45

Pro Gly Asp Ser Ile Ala Arg Gly Ser Ala Ala Asp Val Asp Lys Ala
    50                  55                  60

Val Arg Ala Ala Ala Ala Gln Pro Ala Trp Asn Ala Arg Lys Pro
65                  70                  75                  80

Ile Glu Arg Gly Arg Ile Leu Leu Ala Ile Ala Arg Leu Val Arg Ala
                85                  90                  95

Asn Ala Ala Ala Phe Cys Ala Lys Glu Ala Glu Thr Gly Lys Pro
            100                 105                 110

Leu Lys Met Ala Ala Phe Glu Ile Glu Ala Cys Ala Gln Tyr Phe Glu
        115                 120                 125

Tyr Tyr Gly Gly Leu Ala Thr Ala Ile Gln Gly Glu Thr Ile Asn Leu
    130                 135                 140

Gly Pro Ser Tyr His Ala Tyr Thr Thr Arg Glu Pro Phe Gly Val Val
145                 150                 155                 160

Gly Val Ile Leu Pro Trp Asn Ser Pro Leu Asn Gln Ala Gly Arg Ala
                165                 170                 175

Ile Ala Pro Ala Leu Val Ser Gly Asn Thr Val Val Lys Pro Ser
            180                 185                 190

Glu Phe Thr Ser Val Thr Met Leu Gln Phe Ala Glu Leu Val Val Lys
        195                 200                 205

Glu Ala Gly Leu Pro Pro Gly Val Leu Asn Val Val Thr Gly Thr Gly
    210                 215                 220
```

Lys Glu Thr Gly Glu Pro Leu Val Lys His Pro Leu Ile Arg Lys Val
225                 230                 235                 240

Ala Phe Thr Gly Ser Val Arg Ala Gly Arg Glu Ile Gly Lys Leu Ala
            245                 250                 255

Ala Asp Arg Ile Ile Pro Leu Ser Leu Glu Leu Gly Gly Lys Ser Pro
        260                 265                 270

Asn Ile Val Phe Glu Asp Ala Asp Leu Asp Arg Ala Val Ala Gly Ser
    275                 280                 285

Val Phe Ala Phe Thr Val Asn Thr Gly Gln Val Cys Leu Ala Gly Thr
290                 295                 300

Arg Cys Leu Val His Glu Ser Ile Phe Glu Lys Phe Ser Lys Lys Leu
305                 310                 315                 320

Ala Gly Ala Val Glu Ala Leu Gln Phe Ser Asp Gly Glu Ser Phe Gly
            325                 330                 335

Leu Gly Pro Leu Thr Thr Lys Ala Gln Phe Glu Gln Val His Arg Tyr
        340                 345                 350

Asn Glu Leu Ala Ile Gln Glu Gly Ala His Cys Leu Val Gly Gly Glu
    355                 360                 365

Ala Pro Ser Asp Lys Thr Gly Trp Tyr Val Arg Pro Thr Val Tyr Thr
370                 375                 380

Asn Val Asn Asn Ser Met Arg Ile Ala Arg Glu Glu Ile Phe Gly Pro
385                 390                 395                 400

Val Leu Val Leu Ile Pro Phe Lys Asp Glu Asn Glu Ala Val Ala Ile
            405                 410                 415

Ala Asn Asp Ser Asp Tyr Gly Leu Ala Ala Gly Val Trp Thr Thr Asp
        420                 425                 430

Leu Ala Arg Ala His Arg Val Ser Ala Gln Ile Glu Ala Gly Gln Val
    435                 440                 445

Tyr Val Asn Glu Tyr Pro Ser Gly Gly Val Glu Thr Pro Phe Gly Gly
450                 455                 460

Phe Lys Gln Ser Gly His Gly Arg Glu Lys Gly Ile Glu Ala Leu His
465                 470                 475                 480

His Tyr Thr Gln Thr Lys Thr Thr Ile Ile Arg Ile
            485                 490

<210> SEQ ID NO 50
<211> LENGTH: 1487
<212> TYPE: DNA
<213> ORGANISM: Pseudomonas putida

<400> SEQUENCE: 50
atggtatatc tccttcgaat tctgtttcct gtgtgaaatt gttatccgct cacaattcca      60
cacattatac gagccgatga ttaattgtca acagctcatt tcagaatatt gccagaacc     120 gttatgatgt cggcgcaaaa aacattatcc agaacgggag tgcgccttga gcgacacgaa     180
ttatgcagtg atttacgacc tgcacagcca taccacagct tccgatggct gcctgacgcc     240
agaagcattg gtgcaccgtg cagtcgataa gcccggatca gcttgcaatt cgcgcgcgaa     300
ggcgaagcgg catttacgtt gacaccatcg aatggtgcaa aaccttcgc ggtatggcat     360 gatagcgccc ggaagagagt caattcaggg tggtgaatgt gaaaccagta acgttatacg     420
atgtcgcaga gtatgccggt gtctcttatc agaccgtttc ccgcgtggtg aaccaggcca     480
gccacgtttc tgcgaaaacg cgggaaaaag tggaagcggc gatggcggag ctgaattaca     540
ttcccaaccg cgtggcacaa caactggcgg gcaaacagtc gttgctgatt ggcgttgcca     600

-continued

```
cctccagtct ggccctgcac gcgccgtcgc aaattgtcgc ggcgattaaa tctcgcgccg    660
atcaactggg tgccagcgtg gtggtgtcga tggtagaacg aagcggcgtc gaagcctgta    720
aagcggcggt gcacaatctt ctcgcgcaac gcgtcagtgg gctgatcatt aactatccgc    780
tggatgacca ggatgccatt gctgtggaag ctgcctgcac taatgttccg gcgttatttc    840
ttgatgtctc tgaccagaca cccatcaaca gtattatttt ctcccatgaa gacggtacgc    900
gactgggcgt ggagcatctg gtcgcattgg gtcaccagca aatcgcgctg ttagcgggcc    960
cattaagttc tgtctcggcg cgtctgcgtc tggctggctg gcataaatat ctcactcgca   1020
atcaaattca gccgatagcg gaacgggaag gcgactggag tgccatgtcc ggttttcaac   1080
aaaccatgca aatgctgaat gagggcatcg ttcccactgc gatgctggtt gccaacgatc   1140
agatggcgct gggcgcaatg cgcgccatta ccgagtccgg gctgcgcgtt ggtgcggata   1200
tctcggtagt gggatacgac gataccgaag acagctcatg ttatatcccg ccgttaacca   1260
ccatcaaaca ggattttcgc ctgctggggc aaaccagcgt ggaccgcttg ctgcaactct   1320
ctcagggcca ggcggtgaag ggcaatcagc tgttgcccgt ctcactggtg aaaagaaaaa   1380
ccaccctggc gcccaatacg caaaccgcct ctccccgcgc gttggccgat tcattaatgc   1440
agctggcacg acaggtttcc cgactggaaa gcgggcagtg acaattc                 1487
```

<210> SEQ ID NO 51
<211> LENGTH: 2934
<212> TYPE: DNA
<213> ORGANISM: Pseudomonas putida

<400> SEQUENCE: 51

```
gcaacggcgt ggcggccgcg tcgatggccg ccacctgccg gtcgaggtcg ggcagcaggt     60
agccgaggaa gaacccaacg ctttcctgct tttcccggcg ctgcgccgcc cccactggca    120
acgcctggat gcagcgcgcg ctgcgggccc aggcgaaggc ctgcagcacc gttgcgcaca    180
actgcaggaa gtcgcctgcg gcgcggtacg gaaattcggg atcgcccgcg gtcatcgaca    240
gcaccttggc cagcgctgcc tccagcgtgt cgcacgcact gcccaacgcg gcggcggcgg    300
cgccagcgtc cgcagcggcc tcggtacgca actcactcaa cagcagggcg aaaccttccc    360
ccccatcgcc caataccttg cgcagcatca ggtcgttggc ctgtatttcg ttggtgcctt    420
cgtagatcat cgcgatgcgg ctgtcgcgca aggtctgctc gatggcaaac tcctgggtgt    480
agccatagcc acccaacacc tgcaaggcct tgcttgccag gctgaacccc tgctcggtga    540
aggccgcctt gacgatgggg gtcaacagcg ccgccaatgt cgcagccttc gcccgttgtg    600
caggctcgac ggcggcgtcg gcgatatcca gccactgggc cgtccagtag ccagcgcgc    660 gcatcccctc ggtacgcacc cgcaactcca gcaagacccg acgcatggcc gggtgcaggt    720
ggatcgggtc ggcgccctgg gcgcccccct tggcccgccc cggggcactc atctggcgcc    780
gctccagggc atagtcgcgg gcctgttgcc aggcggcctc agcatgcccc agcccttgca    840
ggccaacatg cagacgcgcg gaattcatca tcacgaacat cgccgccagg ccgccatggg    900
gctggcctat caaccagccc cgggccccct ccaggcgtag tgcacaggtg gcgctgcccc    960
ggatgcccag cttatgttcc aggccgtcgc agtacagtgt attgcgctgg ccatcctcca   1020
gccatttcgg caccagcaac agcgagagcc cgcggttgcc gggcggcgca tccggcaacc   1080
gggccaacac caggtggagt atgtcgcggg tcaggtcgtg ttcgccgcca gagatgaaca   1140
gcttgttgcc actgaccgcg tagccaccgt cgccaccgtc gcccagggc acggcgcggc    1200 agcgcaacag gctgagatcg ctgccggcct ggggttcggt caggcacatg gtaggcaggg   1260
```

```
tggcaccact gacgatgccc ggcagatagc gcgcctgcag ctcggcggat gcatgggctt    1320
tcaggcacag gtaggcaccg tgggcgatgc cggtgtacat ggcccagccg tggttgctgc    1380
cgaacagcat ctcttgcaag gccgcctcca gcactaacgg cagcccttgg ccgccaagcg    1440
ccggggcgca tgccagcgac ggccagccac cgtcgacata ggcgcgataa gccgccggga    1500
atccgtccgg ggtgcgtacc tccccgccct ccatctggca gccctggcga tcgcccgaac    1560
tgttcaaagg ggccagcacc tgctcgcaga aacgggccgc ctcttccagt acctgggccg    1620
ccaggtcgag gtcgacgtcg gcatatgccg gtaattgcgc ccaggcctga tcggcccgca    1680
gccagtgttg caggacgaac tgcatgtcgc gcaggggcgc cttccaggtc atcggatacc    1740
tccgggtcag gcaacgaaat gagggttttc gatcagcagc gccatgcctt ggccaccgcc    1800
gatgcatgcc gctgcgatgc catagcgcaa gttgccgtcg cgcaattgac gggccaaggt    1860
gtggaccagg cgcagacctg tagcggccaa tgggtgacca agggcgatag cgccgccatg    1920
gacattgagc ttgtccacat cgagttcgag cgcctgggcc accgcagca cttgggcggc     1980 ctgggcctcg ttgatttcca ggcggtcgat ctgctccagg cgcaggccgc tgcgctcgag    2040
cagcaaggta atggccggcg ccggcccgat gcccatgagg ccgggcggca cgccaacagc    2100
cgtggccatc agcaagcgcg ccaaaggcgg atgagtgcaa tcggagtagc gcgtgaccaa    2160
ggctgccgcc gcgccatcga ccaccgcgca actgttgcca gccgtctgca cgccaccggc    2220
gtgcaccggg cgcagtcggg ccagtgcggc cgcgtcggta ggccgtgggt ggctgtcctg    2280
gctgacctca ctcacgccac gcggcaatgc aatgccgcgt ggctggcagc cttctacctc    2340
cagtgcctgc gcggtgacgc tgacgatttc ctcgtcgaac cagccctgca cctgggcttg    2400
cagggcccgc tgatggctgc gcagggccca cgcgtccacc gtttcacgcg ccaggccata    2460
ggcacgggcc aggttttccg cagtaccgat catgtccacg ccggcagccg ggtcgtacag    2520
ggcttcccag agaaagtcct tgaacccgac cggcgcccc aggcgaaaac cgccccggtg     2580
ttcataggcc gcgatcggat tgcgcgacat cgactccgcg cccacgcaca gcacctggcg    2640
ggcgccactg cgcagctgtt caccggcctg acgcaacagt tcaaggcccg tgccacagat    2700
gcgctgcacc gccagtgccg gtaccgcctg cggcacgcca cagtagaggc cgacatggcg    2760
tggcagcatg taggcgtcga agctggcctg agccatgctg ccggcgagca cactgtctac    2820
cgcctgaggg gcggcagctg cacgtgccag caccgcgcgg ccggcctgaa tgcccaggtc    2880
gatgggcgag atcgcggcca atgcgccacc caggtcgacc cagggcgtgc gcac          2934
```

<210> SEQ ID NO 52
<211> LENGTH: 396
<212> TYPE: PRT
<213> ORGANISM: Pseudomonas putida

<400> SEQUENCE: 52

```
Met Val Arg Thr Pro Trp Val Asp Leu Gly Gly Ala Leu Ala Ala Ile
1               5                   10                  15

Ser Pro Ile Asp Leu Gly Ile Gln Ala Gly Arg Ala Val Leu Ala Arg
            20                  25                  30

Ala Ala Ala Ala Pro Gln Ala Val Asp Ser Val Leu Ala Gly Ser Met
        35                  40                  45

Ala Gln Ala Ser Phe Asp Ala Tyr Met Leu Pro Arg His Val Gly Leu
    50                  55                  60

Tyr Cys Gly Val Pro Gln Ala Val Pro Ala Leu Ala Val Gln Arg Ile
65                  70                  75                  80
```

```
Cys Gly Thr Gly Leu Glu Leu Arg Gln Ala Gly Glu Gln Leu Arg
                 85                  90                  95

Ser Gly Ala Arg Gln Val Leu Cys Val Gly Ala Glu Ser Met Ser Arg
            100                 105                 110

Asn Pro Ile Ala Ala Tyr Glu His Arg Gly Phe Arg Leu Gly Ala
            115                 120                 125

Pro Val Gly Phe Lys Asp Phe Leu Trp Glu Ala Leu Tyr Asp Pro Ala
            130                 135                 140

Ala Gly Val Asp Met Ile Gly Thr Ala Glu Asn Leu Ala Arg Ala Tyr
145                 150                 155                 160

Gly Leu Ala Arg Glu Thr Val Asp Ala Trp Ala Leu Arg Ser His Gln
                165                 170                 175

Arg Ala Leu Gln Ala Gln Val Gln Gly Trp Phe Asp Glu Ile Val
            180                 185                 190

Ser Val Thr Ala Gln Ala Leu Glu Val Glu Gly Cys Gln Pro Arg Gly
            195                 200                 205

Ile Ala Leu Pro Arg Gly Val Ser Glu Val Ser Gln Asp Ser His Pro
210                 215                 220

Arg Pro Thr Asp Ala Ala Ala Leu Ala Arg Leu Arg Pro Val His Ala
225                 230                 235                 240

Gly Gly Val Gln Thr Ala Gly Asn Ser Cys Ala Val Val Asp Gly Ala
                245                 250                 255

Ala Ala Ala Leu Val Thr Arg Tyr Ser Asp Cys Thr His Pro Pro Leu
                260                 265                 270

Ala Arg Leu Leu Met Ala Thr Ala Val Gly Val Pro Pro Gly Leu Met
                275                 280                 285

Gly Ile Gly Pro Ala Pro Ala Ile Thr Leu Leu Leu Glu Arg Ser Gly
290                 295                 300

Leu Arg Leu Glu Gln Ile Asp Arg Leu Glu Ile Asn Glu Ala Gln Ala
305                 310                 315                 320

Ala Gln Val Leu Ala Val Ala Gln Ala Leu Glu Leu Asp Val Asp Lys
                325                 330                 335

Leu Asn Val His Gly Gly Ala Ile Ala Leu Gly His Pro Leu Ala Ala
                340                 345                 350

Thr Gly Leu Arg Leu Val His Thr Leu Ala Arg Gln Leu Arg Asp Gly
                355                 360                 365

Asn Leu Arg Tyr Gly Ile Ala Ala Cys Ile Gly Gly Gln Gly
            370                 375                 380

Met Ala Leu Leu Ile Glu Asn Pro His Phe Val Ala
385                 390                 395

<210> SEQ ID NO 53
<211> LENGTH: 584
<212> TYPE: PRT
<213> ORGANISM: Pseudomonas putida

<400> SEQUENCE: 53

Met Thr Trp Lys Ala Pro Leu Arg Asp Met Gln Phe Val Leu Gln His
1               5                   10                  15

Trp Leu Arg Ala Asp Gln Ala Trp Ala Gln Leu Pro Ala Tyr Ala Asp
            20                  25                  30

Val Asp Leu Asp Leu Ala Ala Gln Val Leu Glu Glu Ala Ala Arg Phe
            35                  40                  45

Cys Glu Gln Val Leu Ala Pro Leu Asn Ser Ser Gly Asp Arg Gln Gly
```

-continued

```
            50                  55                  60
Cys Gln Met Glu Gly Gly Glu Val Arg Thr Pro Asp Gly Phe Pro Ala
 65                  70                  75                  80

Ala Tyr Arg Ala Tyr Val Asp Gly Gly Trp Pro Ser Leu Ala Cys Ala
                     85                  90                  95

Pro Ala Leu Gly Gly Gln Gly Leu Pro Leu Val Leu Glu Ala Ala Leu
                100                 105                 110

Gln Glu Met Leu Phe Gly Ser Asn His Gly Trp Ala Met Tyr Thr Gly
                115                 120                 125

Ile Ala His Gly Ala Tyr Leu Cys Leu Lys Ala His Ala Ser Ala Glu
                130                 135                 140

Leu Gln Ala Arg Tyr Leu Pro Gly Ile Val Ser Gly Ala Thr Leu Pro
145                 150                 155                 160

Thr Met Cys Leu Thr Glu Pro Gln Ala Gly Ser Asp Leu Ser Leu Leu
                165                 170                 175

Arg Cys Arg Ala Val Pro Leu Gly Asp Gly Asp Gly Gly Tyr Ala
                180                 185                 190

Val Ser Gly Asn Lys Leu Phe Ile Ser Gly Gly Glu His Asp Leu Thr
                195                 200                 205

Arg Asp Ile Leu His Leu Val Leu Ala Arg Leu Pro Asp Ala Pro Pro
                210                 215                 220

Gly Asn Arg Gly Leu Ser Leu Leu Val Pro Lys Trp Leu Glu Asp
225                 230                 235                 240

Gly Gln Arg Asn Thr Leu Tyr Cys Asp Gly Leu Glu His Lys Leu Gly
                245                 250                 255

Ile Arg Gly Ser Ala Thr Cys Ala Leu Arg Leu Glu Gly Ala Arg Gly
                260                 265                 270

Trp Leu Ile Gly Gln Pro His Gly Gly Leu Ala Ala Met Phe Val Met
                275                 280                 285

Met Asn Ser Ala Arg Leu His Val Gly Leu Gln Gly Leu Gly His Ala
290                 295                 300

Glu Ala Ala Trp Gln Gln Ala Arg Asp Tyr Ala Leu Glu Arg Arg Gln
305                 310                 315                 320

Met Ser Ala Pro Gly Arg Ala Lys Gly Gly Ala Gln Gly Ala Asp Pro
                325                 330                 335

Ile His Leu His Pro Ala Met Arg Arg Val Leu Leu Glu Leu Arg Val
                340                 345                 350

Arg Thr Glu Gly Met Arg Ala Leu Ala Tyr Trp Thr Ala Gln Trp Leu
                355                 360                 365

Asp Ile Ala Asp Ala Ala Val Glu Pro Ala Gln Arg Ala Lys Ala Ala
                370                 375                 380

Thr Leu Ala Ala Leu Leu Thr Pro Ile Val Lys Ala Ala Phe Thr Glu
385                 390                 395                 400

Gln Gly Phe Ser Leu Ala Ser Lys Ala Leu Gln Val Leu Gly Gly Tyr
                405                 410                 415

Gly Tyr Thr Gln Glu Phe Ala Ile Glu Gln Thr Leu Arg Asp Ser Arg
                420                 425                 430

Ile Ala Met Ile Tyr Glu Gly Thr Asn Glu Ile Gln Ala Asn Asp Leu
                435                 440                 445

Met Leu Arg Lys Val Leu Gly Asp Gly Gly Glu Gly Phe Ala Leu Leu
450                 455                 460

Leu Ser Glu Leu Arg Thr Glu Ala Ala Ala Asp Ala Gly Ala Ala Ala
465                 470                 475                 480
```

```
Ala Ala Leu Gly Ser Ala Cys Asp Thr Leu Glu Ala Ala Leu Ala Lys
            485                 490                 495

Val Leu Ser Met Thr Ala Gly Asp Pro Glu Phe Pro Tyr Arg Ala Ala
            500                 505                 510

Gly Asp Phe Leu Gln Leu Cys Ala Thr Val Leu Gln Ala Phe Ala Trp
            515                 520                 525

Ala Arg Ser Ala Arg Cys Ile Gln Ala Leu Pro Val Gly Ala Ala Gln
            530                 535                 540

Arg Arg Glu Lys Gln Glu Ser Val Gly Phe Phe Leu Gly Tyr Leu Leu
545                 550                 555                 560

Pro Asp Leu Asp Arg Gln Val Ala Ala Ile Asp Ala Ala Ala Thr Pro
            565                 570                 575

Leu Pro Phe Ile Ala Glu Ser Phe
            580
```